United States Patent
Chaltin et al.

(10) Patent No.: US 9,132,129 B2
(45) Date of Patent: Sep. 15, 2015

(54) ANTIVIRAL COMPOUNDS

(75) Inventors: Patrick Chaltin, Zetrud-Lumay (BE); Frauke Christ, Heverlee (BE); Zeger Debyser, Heverlee (BE); Marc De Maeyer, Vaalbeek (BE); Arnaud Marchand, Korbeek-Lo (BE); Damien Marchand, Kessel-Lo (BE); Arnout Voet, Zwevegem (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 74 days.

(21) Appl. No.: 13/885,526

(22) PCT Filed: Nov. 15, 2011

(86) PCT No.: PCT/EP2011/070089
§ 371 (c)(1),
(2), (4) Date: May 15, 2013

(87) PCT Pub. No.: WO2012/065963
PCT Pub. Date: May 24, 2012

(65) Prior Publication Data
US 2013/0245049 A1 Sep. 19, 2013

(30) Foreign Application Priority Data

Nov. 15, 2010 (EP) .................................... 10191246

(51) Int. Cl.
| | | |
|---|---|---|
| A61K 31/519 | (2006.01) | |
| C07D 487/00 | (2006.01) | |
| C07D 487/14 | (2006.01) | |
| C07D 491/16 | (2006.01) | |
| C07D 221/06 | (2006.01) | |
| C07D 221/08 | (2006.01) | |
| C07D 221/10 | (2006.01) | |
| C07D 401/04 | (2006.01) | |
| C07D 417/04 | (2006.01) | |
| C07D 471/04 | (2006.01) | |
| C07D 471/14 | (2006.01) | |
| C07D 487/04 | (2006.01) | |
| C07D 491/048 | (2006.01) | |
| C07D 491/06 | (2006.01) | |
| C07D 495/04 | (2006.01) | |
| C07D 495/14 | (2006.01) | |
| C07D 519/00 | (2006.01) | |

(Continued)

(52) U.S. Cl.
CPC ............. *A61K 31/519* (2013.01); *A61K 31/437* (2013.01); *A61K 31/473* (2013.01); *A61K 45/06* (2013.01); *C07D 221/06* (2013.01); *C07D 221/08* (2013.01); *C07D 221/10* (2013.01); *C07D 221/16* (2013.01); *C07D 401/04* (2013.01); *C07D 417/04* (2013.01); *C07D 471/04* (2013.01); *C07D 471/14* (2013.01); *C07D 487/04* (2013.01); *C07D 487/14* (2013.01); *C07D 491/048* (2013.01); *C07D 491/06* (2013.01); *C07D 491/16* (2013.01); *C07D 495/04* (2013.01); *C07D 495/14* (2013.01); *C07D 519/00* (2013.01)

(58) Field of Classification Search
CPC ............... C07D 221/06; C07D 487/04; C07D 495/041; C07D 491/06; C07D 471/04; A61K 31/519
USPC .............. 514/290, 291, 292, 293, 294, 259.3; 546/80–85; 544/281
See application file for complete search history.

(56) References Cited

U.S. PATENT DOCUMENTS

| | | | |
|---|---|---|---|
| 3,502,673 A | 3/1970 | Hepworth et al. | |
| 5,336,677 A | 8/1994 | Sarantakis et al. | |

(Continued)

FOREIGN PATENT DOCUMENTS

| | | |
|---|---|---|
| DE | 10-2007-061766 | 6/2009 |
| EP | 237963 | 9/1987 |

(Continued)

OTHER PUBLICATIONS

Chan et al. "The synthesis and some reactions of 2,3-substituted-1-phenylbenzo[f]quinoline," Journal of Heterocyclic Chemistry, 1968, vol. 5, No. 3, pp. 313-318.*

(Continued)

*Primary Examiner* — Shengjun Wang
(74) *Attorney, Agent, or Firm* — Ropes & Gray LLP; Melissa S. Rones; Ryan D. Murphey

(57) ABSTRACT

The present invention relates to compounds of formula (A), as further defined herein, having antiviral activity, more specifically HIV (Human Immunodeficiency Virus) replication inhibiting properties. The invention also relates to pharmaceutical compositions comprising an effective amount of such compounds as active ingredients. The invention further relates to the use of such compounds, optionally combined with one or more other drugs having antiviral activity, for the treatment of animals suffering from viral infections, in particular HIV infection.

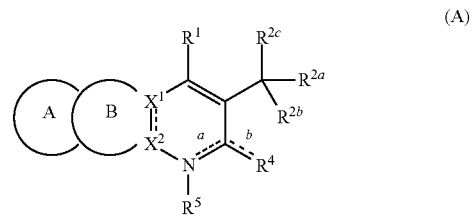

13 Claims, No Drawings

(51) Int. Cl.
A61K 31/437 (2006.01)
A61K 31/473 (2006.01)
A61K 45/06 (2006.01)
C07D 221/16 (2006.01)

(56) References Cited

U.S. PATENT DOCUMENTS

| | | | |
|---|---|---|---|
| 5,474,996 | A | 12/1995 | Caille et al. |
| 5,688,949 | A | 11/1997 | Inoue et al. |
| 7,816,365 | B2 | 10/2010 | Schiemann et al. |
| 8,785,638 | B2 * | 7/2014 | Bardiot et al. ............. 546/80 |
| 8,906,906 | B2 | 12/2014 | Chaltin et al. |
| 2004/0147547 | A1 | 7/2004 | Hu et al. |
| 2006/0040984 | A1 | 2/2006 | Luckhurst et al. |

FOREIGN PATENT DOCUMENTS

| | | |
|---|---|---|
| EP | 169712 | 12/1990 |
| EP | 0591528 | 4/1994 |
| EP | 0795555 | 9/1997 |
| EP | 0941994 | 9/1999 |
| EP | 1015444 | 5/2003 |
| EP | 1505068 | 2/2005 |
| EP | 1471057 | 1/2006 |
| EP | 1375486 | 10/2008 |
| EP | 2006288 | 12/2008 |
| WO | WO96/02519 | 2/1996 |
| WO | WO96/32383 | 10/1996 |
| WO | WO97/25324 | 7/1997 |
| WO | WO98/07705 | 2/1998 |
| WO | WO00/43387 | 7/2000 |
| WO | WO01/14371 | 3/2001 |
| WO | WO01/98301 | 12/2001 |
| WO | WO02/102313 | 12/2002 |
| WO | WO-2004002989 | 1/2004 |
| WO | WO2004/052315 | 6/2004 |
| WO | WO2004/069838 | 8/2004 |
| WO | WO2005/018645 | 3/2005 |
| WO | WO2005/042488 | 5/2005 |
| WO | WO2005/076861 | 8/2005 |
| WO | WO2006/033796 | 3/2006 |
| WO | WO2006/063732 | 6/2006 |
| WO | WO2006/089053 | 8/2006 |
| WO | WO2007/062677 | 6/2007 |
| WO | WO2007/131350 | 11/2007 |
| WO | WO2008/016522 | 2/2008 |
| WO | WO2008/058285 | 5/2008 |
| WO | WO2008/069609 | 6/2008 |
| WO | 2009/062289 A1 | 5/2009 |
| WO | WO2009/062285 | 5/2009 |
| WO | WO2009/062288 | 5/2009 |
| WO | WO2009/062308 | 5/2009 |
| WO | WO2010/089391 | 8/2010 |
| WO | WO2010/130842 | 11/2010 |
| WO | WO2011/076765 | 6/2011 |
| WO | WO-2011151370 | 12/2011 |
| WO | WO-2012066442 | 5/2012 |
| WO | WO-2012067965 | 5/2012 |

OTHER PUBLICATIONS

STN Registration file RN 18819-08-4, 1984.*
Patani et al. "Bioisosterism: A rational approach in drug design," Chem. Review, 1996, vol. 96, pp. 3147-3176.*
Aruyunyan et al., "Synthesis and antitumor properties of new 6-styrylpyrimidine derivatives," (2008) CAPLUS Abstract 150:398461.
Aurora Screening Library, Order No. kam-021378, ethyl (7-{[2-(4-benzyl-1-piperazinyl)ethyl]amino}-5-methyl[1,2,4]triazolo[1,5-a]pyrimidim-6-yl)acetate, CAS Reg. No. 924490-29-9, Publication Date Aug. 20, 2009 (see CHEMCATS Acc. No. 2090530387).
Aurora Screening Library, Order No. kam-017065, ethyl {5-methyl-7-[(1-phenylpropyl)amino][1,2,4]triazolo[1,5-a]pyridimidin-6-yl}acetate, CAS Reg. No. 923547-63-1, Publication Date Aug. 20, 2009 (see CHEMCATS Acc. No. 2090526611).
Bahekar et al., "Synthesis and anti-inflammatory activity of some [2-amino-6-(4-substituted aryl)-4-(4-substituted phenyl)-1,6-dihydropyrimidine-5-yl]-acetic acid derivatives," Acta. Pharma., 53(3):223-229 (2003).
Banker et al, Modern Pharmaceutics, 3ed., Marcel Dekker, New York, pp. 451 and 596 (1996).
Bosseray et al., "[What's new in vaccines against herpes simplex infections?]," Pathol Biol (Paris), 50(8):483-492 (2002) PubMed Abstract.
Chemical Abstracts Service US Database registry Nos. 117646-31-8 (1988) and 107250-17-9 (1986) (accession Nos. 109:230768 and 106:131331).
Chemical Abstracts RN 556020-24-7 5,6, 7 ,8-tetrahydro-2-(4-iodophenyl)-4-phenyl[Benzothieno[2,3-b]pyridine-3-acetic acid, Jul. 28, 2003.
Chemical Abstracts RN 1049765-36-7 5H-Cyclopenta[4,5]thieno[2,3-b]pyridine-3-acetic acid, 6,7-dihydro-4-(4-methylphenyl)-2-(2-thienyl)-, ethyl ester, hydrochloride, Sep. 17, 2008.
Douglas, Jr., "Introduction to viral diseases," Cecil Textbook of Medicine, 20th Ed., 2:1739-1747 (1996).
El-Essawy, "Synthesis of Novel Acyclonucleosides Analogs of Pyridothienopyrimidine as Antiviral Agents," Nucleosides Nucleotides Nucleic Acids, 24(8):1265-1276 (2005).
Goff, "Intracellular trafficking of retroviral genomes during the early phase of infection: viral exploitation of cellular pathways." J Gene Med, 3(6):517-528 (2001) PudMed Abstract.
Grimstrup et al., "Exploration of SAR features by modifications of thiazoleacetic acids as CRTH2 antagonists," Bioorganic & Medicinal Chemistry Letters, 20(5):1638-1641 (2010).
Henze et al., "The number of structurally isomeric alcohols of the methanol series," J. Amer. Chem. Soc., 3042-3046 (1931).
Itoh et al., "The synthesis of 5-substituted 1,2,3-triazines with ketene silyl acetals and ceric ammonium nitrate," Chem. Pharm. Bull., 43(5), 881-883 (1995).
Online "http:/ /web.archive.org/web/20070630171813/http:/ /www.enamine.net/index.php?option=com_content&task=view&id=22 &menuid=51 &PHPSESSID=64a4f248f69d671a413f487bb62c4d90" dated Jun. 30, 2007, accessed Nov. 9, 2011.
Online "http://web.archive.org/web/20030923140513/http:// ambinter.com/" accessed Sep. 3, 2013.
Razonable et al., "Herpesvirus infections in transplant recipients: current challenges in the clinical management of cytomegalovirus and Epstein-Barr virus infections," Herpes, 10(3):60-65 (2003) PubMed Abstract.
Ryabukhin et al., "Heterocyclic Ortho-Aminocarbonyl Compounds in the Friedländer Reaction Promoted by Chlorotrimethylsilane," Heterocycles, 71(11):2397-2411 (2007).
Wolff, "Burger's Medicinal Chemistry, 5ed, Part 1", John Wiley & Sons, pp. 975-977 (1995).
Yamanaka et al., "Reactivity of active oxygen species generated in the EuCl3 catalytic system for monooxygenation of hydrocarbons," J. Chem. Soc., Perkin Trans. 2, 2511-2515 (1996).
Zhou "Anti-AIDS agents 79. Design, synthesis, molecular modeling and structure-activity relationships of novel dicamphanoyl-20,20-dimethyldihydropyranochromone (DCP) analogs as potent anti-HIV agents," Bioorganic & Medicinal Chemistry 18:6678-6689 (2010).

* cited by examiner

ANTIVIRAL COMPOUNDS

CROSS-REFERENCE TO RELATED APPLICATIONS

This application is filed pursuant to 35 U.S.C. §371 as a United States National Phase Application of International Application No. PCT/EP2011/070089 filed Nov. 15, 2011 which claims priority from EP 10191246.7 filed Nov. 15, 2010.

FIELD OF THE INVENTION

The present invention relates to a series of novel compounds having antiviral activity, more specifically HIV (Human Immunodeficiency Virus) replication inhibiting properties. The invention also relates to pharmaceutical compositions comprising an effective amount of such compounds as active ingredients. This invention further relates to the compounds for use as a medicine, to the use of such compounds as medicines, or in the manufacture of a medicament useful for the treatment of animals (including mammals and humans) suffering from viral infections, in particular HIV infection. This invention further relates to methods for the treatment of viral infections in animals (including mammals and humans) by the administration of a therapeutically effective amount of such compounds, optionally combined with one or more other drugs having anti-viral activity.

BACKGROUND OF THE INVENTION

A retrovirus designated human immunodeficiency virus (HIV) is the etiological agent of the complex disease that includes progressive destruction of the immune system (acquired immune deficiency syndrome, hereinafter AIDS) and degeneration of the central and peripheral nervous system. There are two types of HIV, HIV-1 and HIV-2, the latter producing a less severe disease than the former. Being a retrovirus, its genetic material is in the form of RNA (ribonucleic acid) consisting of two single RNA strands. Coexisting with RNA are reverse transcriptase (having polymerase and ribonuclease activity), integrase, a protease and other proteins.

It is known in the art that some antiviral compounds which act as inhibitors of HIV replication are effective agents in the treatment of AIDS and similar diseases. Drugs that are known and approved for the treatment of HIV-infected patients belong to one of the following classes:
- nucleoside reverse transcriptase (RT) inhibitors such as, but not limited to, azidothymidine (AZT), and lamivudine (3TC),
- nucleotide reverse transcriptase inhibitors such as, but not limited to, tenofovir (R-PMPA),
- non-nucleoside reverse transcriptase inhibitors such as, but not limited to, nevirapine, efavirenz, etravirine and lersivirine,
- protease inhibitors such as, but not limited to, nelfinavir, saquinavir, ritonavir, atazanivir, darunavir and amprenavir,
- fusion inihitors such as enfuvirtide,
- CCR5 antagonists such as maraviroc, and
- integrase inhibitors such as raltegravir and elvitegravir.

Replication of HIV-1 can be drastically reduced in infected patients by combining potent antiviral drugs targeted at multiple viral targets, as reviewed by Vandamme et al. in *Antiviral Chem. Chemother.* (1998) 9:187-203.

Multiple-drug combination regimes can reduce viral load below the detection limit of the most sensitive tests. Nevertheless low level ongoing replication has been shown to occur, possibly in sanctuary sites, leading to the emergence of drug-resistant strains, according to Perelson et al. in *Nature* (1997) 387:123-124. Furthermore the selectivity of many antiviral agents is rather low, possibly making them responsible for side-effects and toxicity. Moreover, HIV can develop resistance to most, if not all, currently approved antiviral drugs, according to Schmit et al. in *J. Infect. Dis.* (1996) 174:962-968. It is well documented that the ability of HIV to rapidly evolve drug resistance, together with toxicity problems resulting from known drugs, requires the development of additional classes of antiviral drugs.

Thus, there is still a stringent need in the field for potent inhibitors of HIV. Therefore a goal of the present invention is to satisfy this urgent need by identifying efficient pharmaceutically active ingredients that are active against HIV, less toxic, more stable (i.e. chemically stable, metabolically stable), effective against viruses resistant to currently available drugs and/or which are more resistant to virus mutations than existing antiviral drugs and that can be useful, either alone or in combination with other active ingredients, for the treatment of retroviral infections, in particular lentiviral infections, and more particularly HIV infections, in mammals and more specifically in humans. It is also known to the skilled in the art that the physicochemical properties of known drugs as well as their ADME-Tox (administration, distribution, metabolism, excretion and toxicology) properties may limit or prohibit their use in the treatment of diseases. Therefore, a problem of existing drugs that can be overcome with the compounds of the invention can be selected from a poor or inadequate physicochemical or ADME-Tox properties such as solubility, LogP, CYP inhibition, hepatic stability, plasma stability, among others have been taken into account in the design and the synthesis of the compounds of the present invention. Furthermore, another goal of the present invention is to complement existing antiviral drugs in such a way that the resulting drug combination has improved activity or improved resistance to virus mutation than each of the individual compounds.

SUMMARY OF THE INVENTION

The present invention provides new anti-viral agents, especially anti-retroviral agents, and more particularly anti-HIV compounds. These compounds have been shown to possess anti-viral activity, more specifically against HIV. The present invention demonstrates that these compounds efficiently inhibit the replication of HIV. Therefore, they constitute a useful class of new potent anti-viral compounds that can be used in the treatment and/or prevention of viral infections in animals, mammals and humans, more specifically for the treatment and/or prevention of HIV in humans.

The present invention furthermore relates to the compounds for use as a medicine, to the use of such compounds as medicines, more specifically as anti-viral agents, and to their use for the manufacture of medicaments for treating and/or preventing viral infections, in particular retroviral infections such as, but not limited to, HIV in humans. The invention also relates to pharmaceutical compositions comprising them in an anti-viral effective amount. The present invention also relates to a method of treatment or prevention of viral infections, in particular retroviral infections such as, but not limited to HIV in humans by the administration of one or more such compounds, optionally in combination with one or more other anti-viral agents, to a patient in need thereof.

One aspect of the present invention is the provision of novel compounds, said compounds having a structure according to the formula (A):

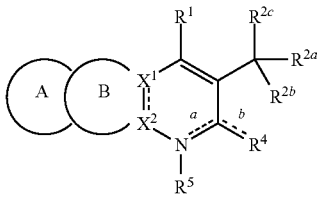

wherein, each dotted line represents an optional double bond, whereby if the dotted line "a" forms a double bond, the dotted line "b" does not form a double bond and whereby if the dotted line "b" forms a double bond, the dotted line "a" does not form a double bond;

$R^1$ is independently selected from alkyl; alkenyl; alkynyl; cycloalkyl; cycloalkenyl; cycloalkynyl; aryl; heterocycle; arylalkyl; arylalkenyl; arylalkynyl; heterocycle-alkyl; heterocycle-alkenyl; or heterocycle-alkynyl;

wherein in the cycloalkyl, cycloalkenyl, cycloalkynyl, alkyl, alkenyl or alkynyl moiety of said alkyl, alkenyl, alkynyl, cycloalkyl, cycloalkenyl, cycloalkynyl, arylalkyl, arylalkenyl, arylalkynyl, heterocycle-alkyl, heterocycle-alkenyl or heterocycle-alkynyl, one or more —$CH_3$, —$CH_2$—, —CH= and/or =CH is optionally replaced by one or more —$NH_2$, —NH—, —O—, —S—, —N= and/or =N;

and wherein said alkyl, alkenyl, alkynyl, cycloalkyl, cycloalkenyl, cycloalkynyl, aryl, heterocycle, arylalkyl, arylalkenyl, arylalkynyl, heterocycle-alkyl, heterocycle-alkenyl, or heterocycle-alkynyl, can be unsubstituted or substituted with one or more $Z^1$;

and wherein optionally a carbon atom or heteroatom of said alkyl, alkenyl, alkynyl, cycloalkyl, cycloalkenyl, cycloalkynyl, aryl, heterocycle, arylalkyl, arylalkenyl, arylalkynyl, heterocycle-alkyl, heterocycle-alkenyl, or heterocycle-alkynyl can be oxidized to form a C=O, C=S, N=O, N=S, S=O or $S(O)_2$;

each of $R^{2a}$ and $R^{2b}$ is independently selected from hydrogen; cyano; alkyl; alkenyl; alkynyl; arylalkyl; arylalkenyl; arylalkynyl; heterocycle-alkyl; heterocycle-alkenyl; or heterocycle-alkynyl; or $R^{2a}$ and $R^{2b}$ are taken together to form vinyl or vinylalkyl; provided that at least one of $R^{2a}$ and $R^{2b}$ is not hydrogen;

wherein in the alkyl, alkenyl or alkynyl moiety of said alkyl, alkenyl, alkynyl, arylalkyl, arylalkenyl, arylalkynyl, heterocycle-alkyl, heterocycle-alkenyl, heterocycle-alkynyl or vinylalkyl, one or more —$CH_3$, —$CH_2$—, —CH= and/or =CH is optionally replaced by one or more —$NH_2$, —NH—, —O—, —S—, —N= and/or =N;

and wherein said alkyl, alkenyl, alkynyl, arylalkyl, arylalkenyl, arylalkynyl, heterocycle-alkyl, heterocycle-alkenyl, heterocycle-alkynyl, vinyl or vinylalkyl, can be unsubstituted or substituted with one or more $Z^1$;

and wherein optionally a carbon atom or heteroatom of said alkyl, alkenyl, alkynyl, arylalkyl, arylalkenyl, arylalkynyl, heterocycle-alkyl, heterocycle-alkenyl, heterocycle-alkynyl, or vinylalkyl can be oxidized to form a C=O, C=S, N=O, N=S, S=O or $S(O)_2$;

$R^{2c}$ is independently selected from —CN; —$CONH_2$; —$COOR^3$; —C(O)NHCN; —C(O)NHOH; —$S(O)_2OH$; —$S(O)_2NHZ^4$; —$P(O)(OH)NH_2$; —P(O)(OH)O-alkyl; —$P(O)(O\text{-alkyl})_2$; —$P(O)OH_2$; —$NHC(O)NHS(O)_2$-aryl; —$NHC(O)NHS(O)_2$-heteroaryl; —$C(O)NHS(O)_2$-aryl; —$C(O)NHS(O)_2$-heteroaryl; —$S(O)_2NHS(O)_2$-aryl; —$S(O)_2NHS(O)_2$-heteroaryl; or from the following structures:

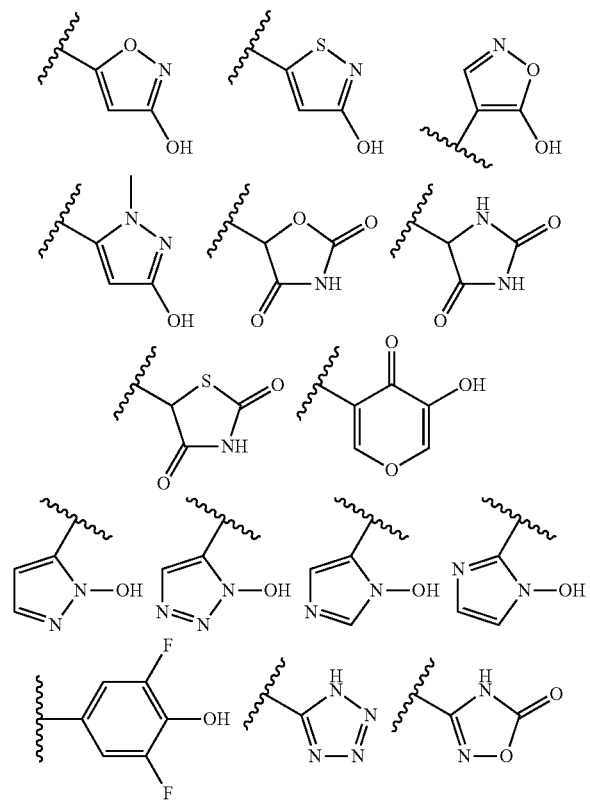

or $R^{2a}$ and $R^{2c}$ or $R^{2b}$ and $R^{2c}$ can be taken together to form a 4, 5, 6 or 7-membered lactone;

$R^3$ is selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl;

wherein in said alkyl, alkenyl, alkynyl, aryl, heterocycle, arylalkyl, arylalkenyl, arylalkynyl, heterocycle-alkyl, heterocycle-alkenyl or heterocycle-alkynyl, one or more —$CH_3$, —$CH_2$—, —CH= and/or =CH is optionally replaced by one or more —$NH_2$, —NH—, —O—, —S—, —N= and/or =N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be oxidized to form a C=O, C=S, N=O, N=S, S=O or $S(O)_2$;

when the dotted line "a" forms a double bond, $R^4$ is independently selected from hydrogen; halogen; cyano;

hydroxyl; alkyl; alkenyl, alkynyl; aryl; heterocycle; arylalkyl; arylalkenyl; arylalkynyl; heterocycle-alkyl; heterocycle-alkenyl; and heterocycle-alkynyl; and when the dotted line "b" forms a double bond, $R^4$ is independently selected from O and S;

wherein in the alkyl, alkenyl or alkynyl moiety of said alkyl, alkenyl, alkynyl, arylalkyl, arylalkenyl, arylalkynyl, heterocycle-alkyl, heterocycle-alkenyl, or heterocycle-alkynyl, one or more —$CH_3$, —$CH_2$—, —CH= and/or ≡CH is optionally replaced by one or more —$NH_2$, —NH—, —O—, —S—, —N= and/or ≡N;

and wherein said alkyl, alkenyl, alkynyl, aryl, heterocycle, arylalkyl, arylalkenyl, arylalkynyl, heterocycle-alkyl, heterocycle-alkenyl, or heterocycle-alkynyl can be unsubstituted or substituted with one or more $Z^1$;

and wherein optionally a carbon atom or heteroatom of said alkyl, alkenyl, alkynyl, arylalkyl, arylalkenyl, arylalkynyl, heterocycle-alkyl, heterocycle-alkenyl, or heterocycle-alkynyl can be oxidized to form a C=O, C=S, N=O, N=S, S=O or $S(O)_2$;

when the dotted line "a" forms a double bond, $R^5$ is not present and when the dotted line "b" forms a double bond, $R^5$ is independently selected from hydrogen; alkyl; alkenyl, alkynyl; aryl; heterocycle; arylalkyl; arylalkenyl; arylalkynyl; heterocycle-alkyl; heterocycle-alkenyl; or heterocycle-alkynyl;

wherein in the alkyl, alkenyl or alkynyl moiety of said alkyl, alkenyl, alkynyl, arylalkyl, arylalkenyl, arylalkynyl, heterocycle-alkyl, heterocycle-alkenyl, or heterocycle-alkynyl, one or more —$CH_3$, —$CH_2$—, —CH= and/or ≡CH is optionally replaced by one or more —$NH_2$, —NH—, —O—, —S—, —N= and/or ≡N;

and wherein said alkyl, alkenyl, alkynyl, aryl, heterocycle, arylalkyl, arylalkenyl, arylalkynyl, heterocycle-alkyl, heterocycle-alkenyl, or heterocycle-alkynyl can be unsubstituted or substituted with one or more $Z^1$;

and wherein optionally a carbon atom or heteroatom of said alkyl, alkenyl, alkynyl, arylalkyl, arylalkenyl, arylalkynyl, heterocycle-alkyl, heterocycle-alkenyl, or heterocycle-alkynyl can be oxidized to form a C=O, C=S, N=O, N=S, S=O or $S(O)_2$;

each of $X^1$ and $X^2$ is independently selected from C or N;

cycle B forms together with $X^1$ and $X^2$ a 5, 6, 7, or 8-membered unsaturated monocyclic cycloalkyl moiety; a 5, 6, 7, or 8-membered monocyclic aryl moiety; or a 5, 6, 7, or 8-membered monocyclic unsaturated or aromatic O, S and/or N containing heterocycle;

wherein said 5, 6, 7, or 8-membered monocyclic unsaturated cycloalkyl moiety, 5, 6, 7, or 8-membered monocyclic aryl moiety, or 5, 6, 7, or 8-membered monocyclic mono-unsaturated, multi-unsaturated or aromatic O, S and/or N containing heterocycle can be unsubstituted or substituted with one or more $R^7$;

and wherein a carbon atom or heteroatom of the 5, 6, 7, or 8-membered monocyclic unsaturated cycloalkyl moiety, 5, 6, 7, or 8-membered monocyclic aryl moiety, or 5, 6, 7, or 8-membered monocyclic mono-unsaturated, multi-unsaturated or aromatic O, S and/or N containing heterocycle can be oxidized to form a C=O, C=S, N=O, N=S, S=O or $S(O)_2$;

cycle A is fused to cycle B and represents a 4, 5, 6, 7, or 8-membered unsaturated monocyclic cycloalkyl moiety; a 4, 5, 6, 7, or 8-membered monocyclic aryl moiety; or a 4, 5, 6, 7, or 8-membered monocyclic saturated, mono-unsaturated, multi-unsaturated or aromatic O, S and/or N containing heterocycle together with the carbon or nitrogen atoms to which they are attached;

wherein said 4, 5, 6, 7, or 8-membered monocyclic unsaturated cycloalkyl moiety, 4, 5, 6, 7, or 8-membered monocyclic aryl moiety, or 4, 5, 6, 7, or 8-membered monocyclic mono-unsaturated, multi-unsaturated or aromatic O, S and/or N containing heterocycle can be unsubstituted or substituted with one or more $R^6$;

and wherein a carbon atom or heteroatom of the 4, 5, 6, 7, or 8-membered monocyclic unsaturated cycloalkyl moiety, 4, 5, 6, 7, or 8-membered monocyclic aryl moiety, or 4, 5, 6, 7, or 8-membered monocyclic mono-unsaturated, multi-unsaturated or aromatic O, S and/or N containing heterocycle can be oxidized to form a C=O, C=S, N=O, N=S, S=O or $S(O)_2$;

$R^6$ is independently selected from $R^{10}$; $R^{11}$; and $R^{12}$;

$R^7$ is independently selected from $R^{10}$; and $R^{12}$;

each of $R^{10}$, $R^{11}$ and $R^{12}$ are independently selected from the group consisting of halogen; —$OZ^2$; —$SZ^2$; —$S(O)Z^3$; —$S(O)_2Z^3$; —$SO_2NZ^4Z^6$; trifluoromethyl; nitro; —$NZ^4Z^5$; —$NZ^2S(O)_2Z^3$; cyano; —$COOZ^2$; —$C(O)NZ^4Z^6$; —$C(O)Z^3$; alkyl; alkenyl; alkynyl; aryl; heterocycle; arylalkyl; arylalkenyl; arylalkynyl; heterocycle-alkyl; heterocycle-alkenyl; or heterocycle-alkynyl;

and wherein said alkyl, alkenyl, alkynyl, aryl, arylalkyl, arylalkenyl, arylalkynyl, heterocycle-alkyl, heterocycle-alkenyl or heterocycle-alkynyl, optionally includes one or more heteroatoms, said heteroatoms being selected from the atoms O, S and N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$;

and wherein optionally a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be oxidized to form a C=O, C=S, N=O, N=S, S=O or $S(O)_2$;

$R^{10}$ and $R^{11}$ on the same carbon atom can be taken together to form a 5, 6 or 7-membered spiro-cycloalkyl, spiro-cycloalkenyl, spiro-cycloalkynyl or a saturated or unsaturated spiro-heterocycle together with the cycle A they are attached to; or an $R^{10}$ and another $R^{10}$, $R^{11}$ or $R^{12}$ on adjacent atoms can be taken together to form a 5, 6 or 7-membered cycloalkyl, cycloalkenyl, cycloalkynyl, aryl or heterocycle fused to the cycle A or cycle B they are attached to;

each $Z^1$ is independently selected from the group consisting of halogen; —$OZ^2$; —$SZ^2$; —$S(O)Z^3$; —$S(O)_2Z^3$; —$SO_2NZ^4Z^5$; trifluoromethyl; nitro; —$NZ^4Z^5$; —$NZ^2S(O)_2Z^3$; cyano; —$COOZ^2$; —$C(O)NZ^4Z^5$; —$C(O)Z^3$; alkyl; alkenyl; alkynyl; aryl; heterocycle; arylalkyl; arylalkenyl; arylalkynyl; heterocycle-alkyl; heterocycle-alkenyl; and heterocycle-alkynyl;

and wherein in the alkyl, alkenyl or alkynyl moiety of said alkyl, alkenyl, alkynyl, arylalkyl, arylalkenyl, arylalkynyl, heterocycle-alkyl, heterocycle-alkenyl or heterocycle-alkynyl, one or more —$CH_3$, —$CH_2$—, —CH= and/or ≡CH is optionally replaced by one or more —$NH_2$, —NH—, —O—, —S—, —N= and/or ≡N;

and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with one or more $Z^{11}$;

and wherein optionally a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be oxidized to form a C═O, C═S, N═O, N═S, S═O or S(O)$_2$; or two $Z^1$ on the same carbon atom can be taken together to form a 5, 6 or 7-membered spiro-cycloalkyl, spiro-cycloalkenyl, spiro-cycloalkynyl, or a saturated or unsaturated spiro-heterocycle together with the (4, 5, 6, 7 or 8-membered unsaturated) ring they are attached to; or two $Z^1$ on adjacent atoms can be taken together to form a 5, 6 or 7-membered cycloalkyl, cycloalkenyl, cycloalkynyl, aryl or heterocycle fused to the (4, 5, 6, 7, or 8-membered unsaturated) ring they are attached to;

each $Z^{11}$ is independently selected from the group consisting of halogen; —$OZ^{12}$; —$SZ^{12}$; —$S(O)Z^{13}$; —$S(O)_2Z^{13}$; —$SO_2NZ^{14}Z^{15}$; trifluoromethyl; nitro; —$NZ^{14}Z^{15}$; —$NZ^{12}S(O)_2Z^{13}$; cyano; —$COOZ^{12}$; —$C(O)NZ^{14}Z^{15}$; —$C(O)Z^{13}$; alkyl; alkenyl; alkynyl; aryl; heterocycle; arylalkyl; arylalkenyl; arylalkynyl; heterocycle-alkyl; heterocycle-alkenyl; and heterocycle-alkynyl;

each $Z^2$ and $Z^{12}$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein in said alkyl, alkenyl, alkynyl, aryl, heterocycle, arylalkyl, arylalkenyl, arylalkynyl, heterocycle-alkyl, heterocycle-alkenyl or heterocycle-alkynyl, one or more —$CH_3$, —$CH_2$—, —CH═ and/or ═CH is optionally replaced by one or more —$NH_2$, —NH—, —O—, —S—, —N═ and/or ═N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be oxidized to form a C═O, C═S, N═O, N═S, S═O or S(O)$_2$;

each $Z^3$ and $Z^{13}$ is independently selected from hydroxyl; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein in said alkyl, alkenyl, alkynyl, aryl, heterocycle, arylalkyl, arylalkenyl, arylalkynyl, heterocycle-alkyl, heterocycle-alkenyl or heterocycle-alkynyl, one or more —$CH_3$, —$CH_2$—, —CH═ and/or ═CH is optionally replaced by one or more —$NH_2$, —NH—, —O—, —S—, —N═ and/or ═N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be oxidized to form a C═O, C═S, N═O, N═S, S═O or S(O)$_2$;

each $Z^4$, $Z^5$, $Z^{14}$ and $Z^{15}$ is independently selected from hydrogen; alkyl; alkenyl; alkynyl; aryl; heterocycle; arylalkyl; arylalkenyl; arylalkynyl; heterocycle-alkyl; heterocycle-alkenyl or heterocycle-alkynyl; and wherein in said alkyl, alkenyl, alkynyl, aryl, heterocycle, arylalkyl, arylalkenyl, arylalkynyl, heterocycle-alkyl, heterocycle-alkenyl or heterocycle-alkynyl, one or more —$CH_3$, —$CH_2$—, —CH═ and/or ═CH is optionally replaced by one or more —$NH_2$, —NH—, —O—, —S—, —N═ and/or ═N; and wherein said alkyl, alkenyl, alkynyl, aryl, heterocycle, arylalkyl, arylalkenyl, arylalkynyl, heterocycle-alkyl, heterocycle-alkenyl or heterocycle-alkynyl can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$; and wherein optionally a carbon atom or heteroatom of said alkyl, alkenyl, alkynyl, aryl, heterocycle, arylalkyl, arylalkenyl, arylalkynyl, heterocycle-alkyl, heterocycle-alkenyl or heterocycle-alkynyl can be oxidized to form a C═O, C═S, N═O, N═S, S═O or S(O)$_2$; and wherein $Z^4$ and $Z^5$, and $Z^{14}$ and $Z^{15}$ respectively can be taken together in order to form a (5-, 6-, or 7-membered) heterocycle which can be unsubstituted or substituted with alkyl, alkenyl, alkynyl, hydroxyl, halogen, —SH, trifluoromethyl, —O-alkyl, —$OCF_3$, cyano, nitro, —COOH or $NH_2$;

and pharmaceutically acceptable salts thereof, provided that the compounds do not have a structure according to formula (N)

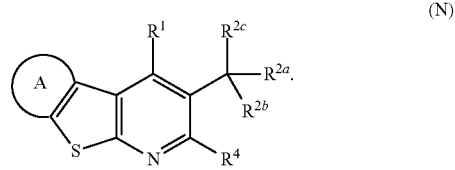

In a particular embodiment of this aspect of the invention the compounds have a structure according to formula (A1),

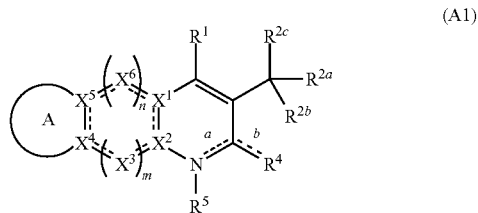

wherein, each of $R^1$, $R^{2a}$, $R^{2b}$, $R^{2c}$, $R^3$, $R^4$, $R^5$, $R^6$, $R^7$, $R^{10}$, $R^{11}$, $R^{12}$, $X^1$, $X^2$, cycle A, $Z^1$, $Z^{11}$, $Z^2$, $Z^{12}$, $Z^3$, $Z^{13}$, $Z^4$, $Z^5$, $Z^{14}$ and $Z^{15}$ are as in formula (A);

each dotted line represents an optional double bond whereby maximally five non-adjacent dotted lines can form a double bond;

each of $X^3$ and $X^6$ are independently selected from CH; $CR^{10}$; N; $NR^{12}$; O and S;

each of $X^4$ and $X^5$ are independently selected from C; and N; n is selected from 0; 1; 2; 3; and 4;

m is selected from 0; 1; 2; 3 and 4; and whereby m+n is at least 1 and maximally 4;

provided that the compounds do not have a structure according to formula (N)

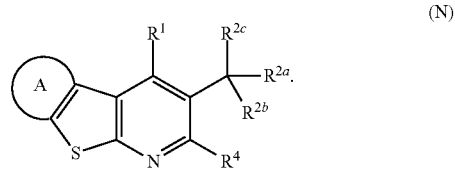

In another particular embodiment of this aspect of the invention the compounds have a structure according to formula (A2), (A2)

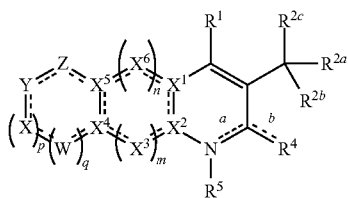

wherein,
each of $R^1$, $R^{2a}$, $R^{2b}$, $R^{2c}$, $R^3$, $R^4$, $R^5$, $R^6$, $R^7$, $R^{10}$, $R^{11}$, $R^{12}$, $X^1$, $X^2$, $Z^1$, $Z^{11}$, $Z^2$, $Z^{12}$, $Z^3$, $Z^{13}$, $Z^4$, $Z^5$, $Z^{14}$, $Z^{15}$, $X^3$, $X^6$, $X^4$, $X^5$, m and n are as in formula (A1);

each dotted line represents an optional double bond whereby maximally nine non-adjacent dotted lines can form a double bond;

W, X, Y, and Z are independently selected from $CR^{10}$; $CR^{10}R^{11}$; N; $NR^{12}$; O and S depending on whether they are adjacent to a double or a single bond;

p is selected from 0; 1; 2; and 3; and q is selected from 0; and 1;

provided that the compounds do not have a structure according to formula (N)

(N)

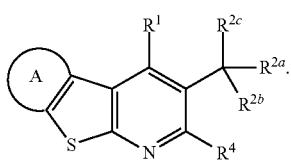

In a particular embodiment of the present aspect, the invention provides compounds with a structure according to formulae (B), (B1) or (B2), (B)

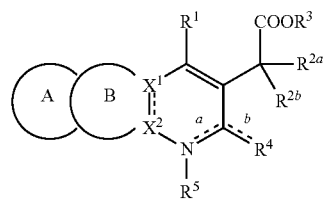

(B1)

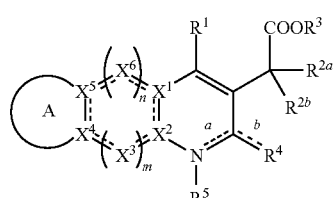

(B2)

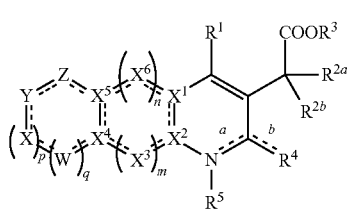

wherein
each of $R^1$, $R^{2a}$, $R^{2b}$, $R^{2c}$, $R^3$, $R^4$, $R^5$, $R^6$, $R^7$, $R^{10}$, $R^{11}$, $R^{12}$, $X^1$, $X^2$, $Z^1$, $Z^{11}$, $Z^2$, $Z^{12}$, $Z^3$, $Z^{13}$, $Z^4$, $Z^5$, $Z^{14}$, $Z^{15}$, $X^3$, $X^6$, $X^4$, $X^5$, m, n, the dotted lines, W, X, Y, Z, p and q are as in formulae (A), (A1) and (A2) respectively;

provided that the compounds do not have a structure according to formula (N)

(N)

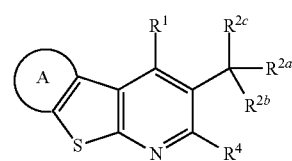

wherein $R^{2c}$ is $COOR^3$.

In another particular embodiment of the present aspect, the invention provides compounds with a structure according to formulae (C1), (C2), (C3), (C4), (C5), (C6), (C7), (C8), (C9) or (C10)

(C1)

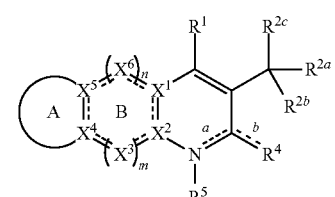

(C2)

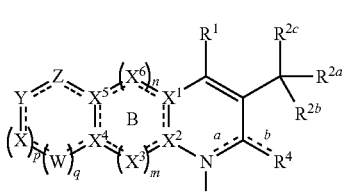

(C3)

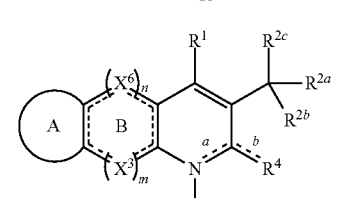

(C4)

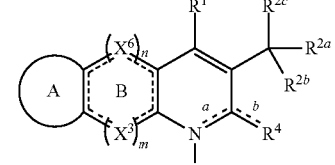

(C5)

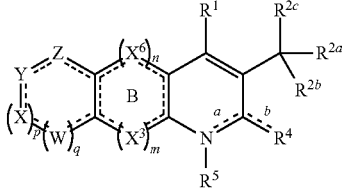

-continued

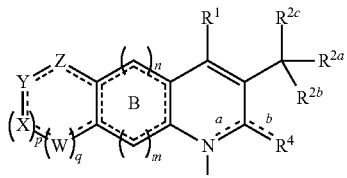
(C6)

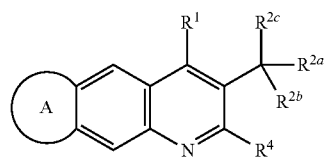
(C5a)

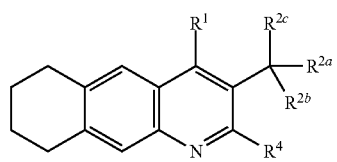
(C6a)

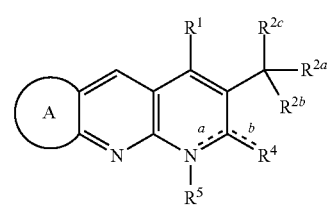
(C7)

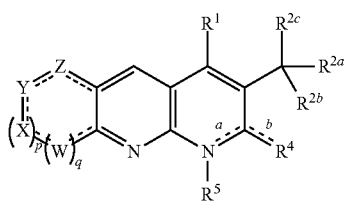
(C8)

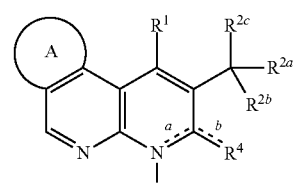
(C9)

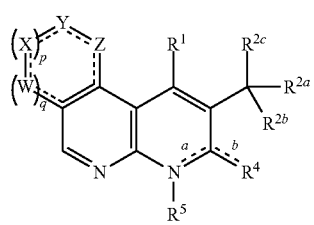
(C10)

wherein,
each of $R^1$, $R^{2a}$, $R^{2b}$, $R^{2c}$, $R^3$, $R^4$, $R^5$, $R^6$, $R^7$, $R^{10}$, $R^{11}$, $R^{12}$, $X^1$, $X^2$, $Z^1$, $Z^{11}$, $Z^2$, $Z^{12}$, $Z^3$, $Z^{13}$, $Z^4$, $Z^5$, $Z^{14}$, $Z^{15}$, $X^3$, $X^6$, $X^4$, $X^5$, the dotted lines, W, X, Y, Z, p and q are as in formulae (A1) for (C1), (C3), (C5), (C5a) (C7) and (C9) and as in formula (A2) for (C2), (C4), (C6), (C6a), (C8) and (C10);
cycle B is aromatic;
m is selected from 0; 1; and 2; and
n is selected from 0; 1 and 2; whereby m+n is 2.

In another particular embodiment of the present aspect, the invention provides compounds with a structure according to formulae (D1), or (D2),

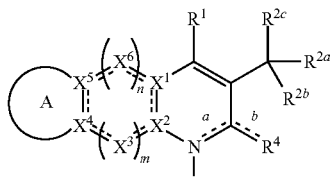
(D1)

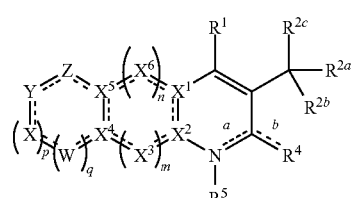
(D2)

wherein,
each of $R^1$, $R^{2a}$, $R^{2b}$, $R^{2c}$, $R^3$, $R^4$, $R^5$, $R^6$, $R^7$, $R^{10}$, $R^{11}$, $R^{12}$, $X^1$, $X^2$, $Z^1$, $Z^{11}$, $Z^2$, $Z^{12}$, $Z^3$, $Z^{13}$, $Z^4$, $Z^5$, $Z^{14}$, $Z^{15}$, $X^3$, $X^6$, $X^4$, $X^5$, the dotted lines, W, X, Y, Z, p and q are as in formulae (A1) for (D1) and as in formula (A2) for (D2);
m is selected from 0; and 1; and
n is selected from 0; and 1; whereby m+n is 1
provided that the compounds do not have a structure according to formula (N)

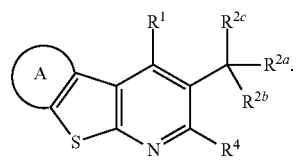
(N)

In another particular embodiment of the present aspect, the invention provides compounds with a structure according to formulae (E1), or (E2),

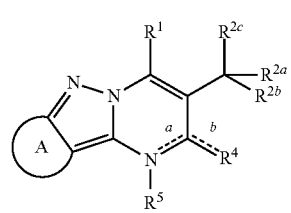
(E1)

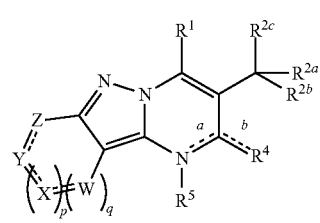
(E2)

wherein, each of $R^1$, $R^{2a}$, $R^{2b}$, $R^{2c}$, $R^3$, $R^4$, $R^5$, $R^6$, $R^{10}$, $R^{11}$, $R^{12}$, $Z^1$, $Z^{11}$, $Z^2$, $Z^{12}$, $Z^3$, $Z^{13}$, $Z^4$, $Z^5$, $Z^{14}$, $Z^{15}$, the dotted lines, W, X, Y, Z, p and q are as in formulae (A1) for (E1) and as in formula (A2) for (E2).

In another particular embodiment of the present aspect, the invention provides compounds with a structure according to formulae (F1), (F2), (F3), or (F4),

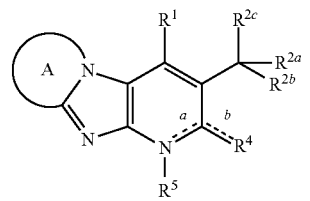
(F1)

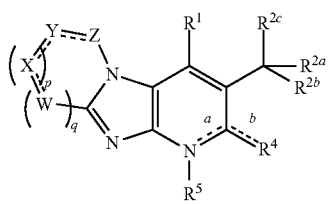
(F2)

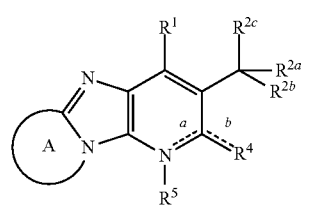
(F3)

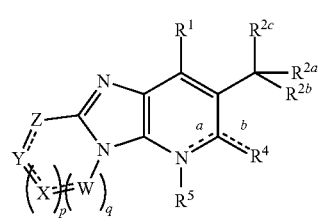
(F4)

wherein, each of $R^1$, $R^{2a}$, $R^{2b}$, $R^{2c}$, $R^3$, $R^4$, $R^5$, $R^6$, $R^{10}$, $R^{11}$, $R^{12}$, $Z^1$, $Z^{11}$, $Z^2$, $Z^{12}$, $Z^3$, $Z^{13}$, $Z^4$, $Z^5$, $Z^{14}$, $Z^{15}$, the dotted lines, W, X, Y, Z, p and q are as in formulae (A1) for (F1) and (F3) and as in formula (A2) for (F2) and (F4).

In another particular embodiment of the present aspect, the invention provides compounds with a structure according to formulae (G1), or (G2),

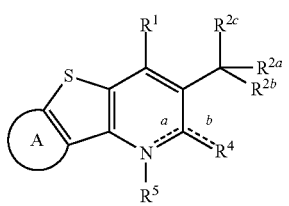
(G1)

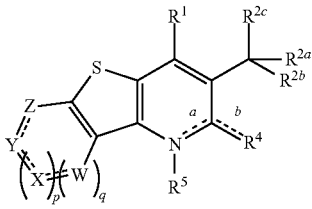
(G2)

wherein, each of $R^1$, $R^{2a}$, $R^{2b}$, $R^{2c}$, $R^3$, $R^4$, $R^5$, $R^6$, $R^{10}$, $R^{11}$, $R^{12}$, $Z^1$, $Z^{11}$, $Z^2$, $Z^{12}$, $Z^3$, $Z^{13}$, $Z^4$, $Z^5$, $Z^{14}$, $Z^{15}$, the dotted lines, W, X, Y, Z, p and q are as in formulae (A1) for (G1) and as in formula (A2) for (G2).

In another particular embodiment of the present aspect, the invention provides compounds with a structure according to formulae (H1), or (H2),

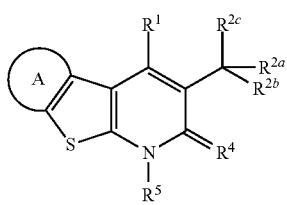
(H1)

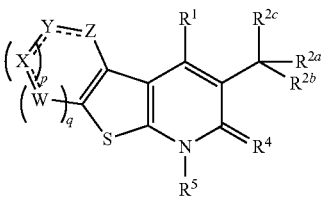
(H2)

wherein, each of $R^1$, $R^{2a}$, $R^{2b}$, $R^{2c}$, $R^3$, $R^4$, $R^5$, $R^6$, $R^{10}$, $R^{11}$, $R^{12}$, $Z^1$, $Z^{11}$, $Z^2$, $Z^{12}$, $Z^3$, $Z^{13}$, $Z^4$, $Z^5$, $Z^{14}$, $Z^{15}$, the dotted lines, W, X, Y, Z, p and q are as in formulae (A1) for (H1) and as in formula (A2) for (H2).

In another particular embodiment of the present aspect, the invention provides compounds with a structure according to formulae (I1), or (I2),

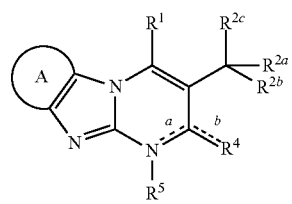
(I1)

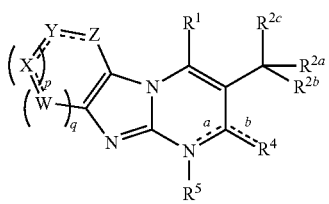
(I2)

wherein,
each of $R^1$, $R^{2a}$, $R^{2b}$, $R^{2c}$, $R^3$, $R^4$, $R^5$, $R^6$, $R^{10}$, $R^{11}$, $R^{12}$, $Z^1$, $Z^{11}$, $Z^2$, $Z^{12}$, $Z^3$, $Z^{13}$, $Z^4$, $Z^5$, $Z^{14}$, $Z^{15}$, the dotted lines, W, X, Y, Z, p and q are as in formulae (A1) for (I1) and as in formula (A2) for (I2).

In another particular embodiment of the present aspect, the invention provides compounds with a structure according to formulae (J1), (J2), (J3) or (J4)

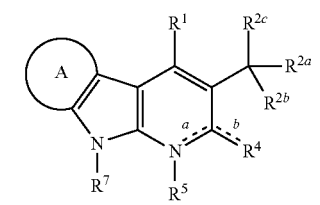
(J1)

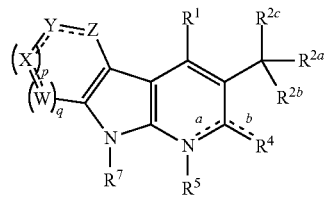
(J2)

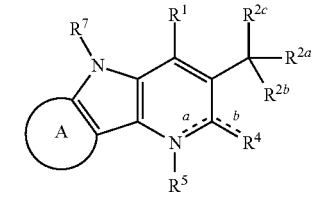
(J3)

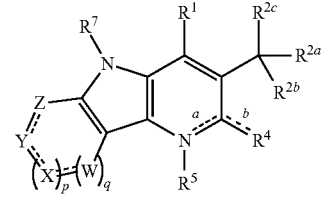
(J4)

wherein,
each of $R^1$, $R^{2a}$, $R^{2b}$, $R^{2c}$, $R^3$, $R^4$, $R^5$, $R^6$, $R^7$, $R^{10}$, $R^{11}$, $R^{12}$, $Z^1$, $Z^{11}$, $Z^2$, $Z^{12}$, $Z^3$, $Z^{13}$, $Z^4$, $Z^5$, $Z^{14}$, $Z^{15}$, the dotted lines, W, X, Y, Z, p and q are as in formulae (A1) for (J1) and (J3) and as in formula (A2) for (J2) and (J4).

In a particular embodiment, and in each of the embodiments (A), (A1), (A2), (B), (B1), (B2), (C1), (C2), (C3), (C4), (C5), (C5a), (C6), (C6a), (C7), (C8), (C9), (C10), (D1), (D2), (E1), (E2), (F1), (F2), (F3), (F4), (G1), (G2), (H1), (H2), (I1), (I2), (J1), (J2), (J3) and (J4), $R^1$ is selected from substituted or unsubstituted aryl, heteroaryl, $C_1$-$C_6$ alkyl, —O-aryl, —S-aryl, —NH-aryl, —O-heterocycle, —S-heterocycle, and —NH-heterocycle, (preferably from aryl or heteroaryl), and yet in a more particular embodiment is selected from phenyl, —O-phenyl, —S-phenyl, —NH-phenyl, pyridinyl, furanyl, thiophenyl, indolyl, benzofuranyl, t-butyl, and benzo[d][1,3] dioxolyl (preferably benzo[d][1,3]dioxol-5-yl), preferably $R^1$ is selected from phenyl, wherein said aryl, heteroaryl, $C_1$-$C_6$ alkyl, —O-aryl, —S-aryl, —NH-aryl, —O-heterocycle, —S-heterocycle, and —NH-heterocycle (preferably from aryl or heteroaryl), or more particularly phenyl, —O-phenyl, —S-phenyl, —NH-phenyl, pyridinyl, furanyl, thiophenyl, indolyl, benzofuranyl, t-butyl, and benzo[d][1,3] dioxolyl (preferably benzo[d][1,3]dioxol-5-yl), preferably phenyl, can be unsubstituted or substituted, in a particular embodiment substituted with one or more $Z^1$. Preferably, $R^1$ is selected from phenyl, tolyl, chlorophenyl, dichlorophenyl, fluorophenyl, trifluoromethylphenyl, ethylphenyl, methoxyphenyl, dimethoxyphenyl, trifluoromethoxyphenyl, pyridinyl, furanyl, thiophenyl, indolyl, benzofuranyl, t-butyl, benzo[d]dioxolyl (preferably benzo[d][1,3]dioxol-5-yl), 2,3-dihydropyrano[4,3,2-de]quinolinyl, chromanyl, 3,4-dihydro-2H-benzo[b][1,4]oxazinyl, 1,2,3,4-tetrahydroquinolinyl, and 2,3-dihydrobenzofuranyl. In another particular embodiment, $R^1$ is substituted phenyl, in a particular embodiment substituted with one or more $Z^1$. Preferably $R^1$ is phenyl substituted with one or more groups selected from methyl, ethyl, chloro, fluoro, trifluoromethyl, hydroxyl, and methoxy. More preferably, $R^1$ is p-tolyl, unsubstituted or substituted with one or more $Z^1$. More particularly, $R^1$ is o-hydroxy-p-tolyl.

In another particular embodiment, and in each of the embodiments (A), (A1), (A2), (B), (B1), (B2), (C1), (C2), (C3), (C4), (C5), (C5a), (C6), (C6a), (C7), (C8), (C9), (C10), (D1), (D2), (E1), (E2), (F1), (F2), (F3), (F4), (G1), (G2), (H1), (H2), (I1), (I2), (J1), (J2), (J3) and (J4), one of $R^{2a}$ and $R^{2b}$ is hydrogen and the other one is selected from the group consisting of $C_1$-$C_6$ alkyl and $C_1$-$C_6$-alkoxy, more preferably selected from the group consisting of $C_1$-$C_4$ alkyl and $C_1$-$C_4$-alkoxy, preferably n-propyl and butoxy, or one of $R^{2a}$ and $R^{2b}$ is hydrogen and the other one is taken together with $R^3$ to form a gamma-lactone radical, preferably a dihydrofuran-2(3H)-one radical.

In yet another particular embodiment, and in each of the embodiments (A), (A1), (A2), (C1), (C2), (C3), (C4), (C5), (C5a), (C6), (C6a), (C7), (C8), (C9), (C10), (D1), (D2), (E1), (E2), (F1), (F2), (F3), (F4), (G1), (G2), (H1), (H2), (I1), (I2), (J1), (J2), (J3) and (J4), $R^{2c}$ is selected from —COOH, COOalkyl (preferably —COOMe or —COOEt, more preferably —COOMe), —CN, —C(O)NH$_2$, —C(O)NH(CN), —P(O)OH$_2$;

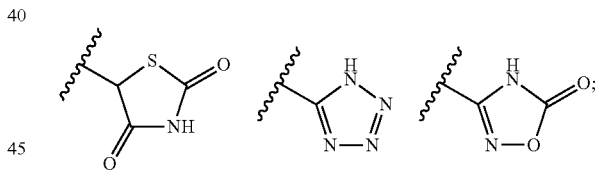

preferably $R^{2c}$ is —COOH or —COOalkyl (preferably —COOMe or —COOEt, more preferably —COOMe), more preferably $R^{20}$ is —COOH.

In yet another particular embodiment, and in each of the embodiments (A), (A1), (A2), (B), (B1), (B2), (C1), (C2), (C3), (C4), (C5), (C5a), (C6), (C6a), (C7), (C8), (C9), (C10), (D1), (D2), (E1), (E2), (F1), (F2), (F3), (F4), (G1), (G2), (I1), (I2), (J1), (J2), (J3) and (J4), the dotted line a forms a double bond, the dotted line b does not form a double bond, $R^5$ is not present and $R^4$ is selected from hydrogen, hydroxyl, alkyl or aryl, wherein said alkyl and aryl can be unsubstituted or substituted, in a particular embodiment substituted with one or more $Z^1$. Preferably, $R^4$ is selected from hydrogen, alkyl or aryl, wherein said alkyl and aryl can be unsubstituted or substituted, in a particular embodiment substituted with one or more $Z^1$. More preferably, $R^4$ is selected from $C_1$-$C_4$ alkyl, even more preferably $R^4$ is methyl.

In yet another particular embodiment, and in each of the embodiments (A), (A1), (A2), (B), (B1), (B2), (C1), (C2), (C3), (C4), (C5), (C6), (C7), (C8), (C9), (C10), (D1), (D2), (E1), (E2), (F1), (F2), (F3), (F4), (G1), (G2), (H1), (H2), (I1), (I2), (J1), (J2), (J3) and (J4), the dotted line a does not form a double bond, the dotted line b forms a double bond, $R^4$ is selected from oxygen, and $R^5$ is selected from hydrogen, alkyl, aryl, and arylalkyl, wherein said alkyl and aryl can be unsubstituted or substituted, in a particular embodiment substituted with one or more $Z^1$. Preferably, $R^5$ is selected from hydrogen, alkyl or aryl, wherein said alkyl and aryl can be unsubstituted or substituted, in a particular embodiment substituted with one or more $Z^1$. More preferably, $R^5$ is selected from hydrogen and $C_1$-$C_4$ alkyl.

In another particular embodiment of the invention, and in each of the embodiments (A), (A1), (B), (B1), (C1), (C3), (C5), (C5a), (C7), (C9), (D1), (E1), (F1), (F3), (G1), (H1), (I1), (J1), and (J3), cycle A is selected from a 4, 5, 6, 7, or 8-membered unsaturated monocyclic cycloalkyl moiety; and a 4, 5, 6, 7, or 8-membered monocyclic aryl moiety. In yet another particular embodiment, cycle A is selected from a 5 or 6-membered unsaturated monocyclic cycloalkyl moiety; and a 6-membered monocyclic aryl moiety. In yet another particular embodiment, cycle A is selected from cyclopentenyl, cyclohexenyl, and phenyl.

In another particular embodiment, and in each of the embodiments (A2), (B2), (C2), (C4), (C6), (C8), (C10), (D2), (E2), (F2), (F4), (G2), (H2), (I2), (J2), and (J4), q is 1 and p is selected from 0 and 1.

In yet another particular embodiment of the invention, and in each of the embodiments (A2), (B2), (C2), (C4), (C6), (C8), (C10), (D2), (E2), (F2), (F4), (G2), (H2), (I2), (J2), and (J4), each of W, X, Y and Z is selected from $CR^{10}$ and $CR^{10}R^{11}$ depending on whether they are adjacent to a double or a single bond. In a particular embodiment, each of W, X, Y and Z is selected from $CR^{10}$ and $CR^{10}R^{11}$ depending on whether they are adjacent to a double or a single bond, wherein $R^{10}$ and $R^{11}$ are independently selected from the group consisting of hydrogen and alkyl. In yet another particular embodiment of the invention, each of W, X, Y and Z is selected from CH and $CH_2$ depending on whether they are adjacent to a double or a single bond.

In still a more particular embodiment, the compounds are selected from:
2-(2-methyl-4-p-tolyl-6,7,8,9-tetrahydrobenzo[g]quinolin-3-yl)pentanoic acid
2-tert-butoxy-2-(2-methyl-4-p-tolyl-6,7,8,9-tetrahydrobenzo[g]quinolin-3-yl)acetic acid
2-(3-methyl-1-p-tolyl-7,8,9,10-tetrahydrobenzo[f]quinolin-2-yl)pentanoic acid
2-tert-butoxy-2-(2-methyl-4-p-tolyl-7,8-dihydro-6H-cyclopenta[g]quinolin-3-yl)acetic acid
2-tert-butoxy-2-(3-methyl-1-p-tolyl-8,9-dihydro-7H-cyclopenta[f]quinolin-2-yl)acetic acid
2-(1-methyl-2-oxo-4-p-tolyl-2,6,7,8-tetrahydro-1H-cyclopenta[g]quinolin-3-yl)pentanoic acid
2-(4-methyl-3-oxo-1-p-tolyl-4,7,8,9-tetrahydro-3H-cyclopenta[f]quinolin-2-yl)pentanoic acid
2-(1-(benzo[d]thiazol-6-yl)-3-methyl-8,9-dihydro-7H-cyclopenta[f]quinolin-2-yl)pentanoic acid
2-(2-methyl-4-(phenylamino)-6,7,8,9-tetrahydrobenzo[g]quinolin-3-yl)pentanoic acid
2-(2-methyl-4-(phenylthio)-7,8-dihydro-6H-cyclopenta[g]quinolin-3-yl)pentanoic acid
2-(3-methyl-1-phenoxy-8,9-dihydro-7H-cyclopenta[f]quinolin-2-yl)pentanoic acid
2-(2-methyl-4-p-tolyl-7,8-dihydro-6H-cyclopenta[g]quinolin-3-yl)pentanoic acid
2-(2-hydroxy-4-p-tolyl-6,7,8,9-tetrahydrobenzo[g]quinolin-3-yl)pentanoic acid
2-(3-hydroxy-1-p-tolyl-7,8,9,10-tetrahydrobenzo[f]quinolin-2-yl)pentanoic acid
2-(3-ethyl-1-p-tolyl-7,8,9,10-tetrahydrobenzo[f]quinolin-2-yl)pentanoic acid
2-(2-ethyl-4-p-tolyl-7,8-dihydro-6H-cyclopenta[g]quinolin-3-yl)pentanoic acid
2-tert-butoxy-2-(2-methyl-4-(1-methyl-1H-pyrazol-4-yl)-6,7,8,9-tetrahydrobenzo[g]quinolin-3-yl)acetic acid
2-(4-(4-chloro-2-fluorophenyl)-2-methyl-7,8-dihydro-6H-cyclopenta[g]quinolin-3-yl)-6,6,6-trifluorohexanoic acid
6,6,6-trifluoro-2-(3-methyl-1-p-tolyl-8,9-dihydro-7H-cyclopenta[f]quinolin-2-yl)hexanoic acid
2-(1-(benzo[d]thiazol-6-yl)-3-methyl-7,8,9,10-tetrahydrobenzo[f]quinolin-2-yl)-4-methoxybutanoic acid
2-(1-(2,3-dihydropyrano[4,3,2-de]quinolin-7-yl)-3-methyl-8,9-dihydro-7H-cyclopenta[f]quinolin-2-yl)pentanoic acid
3-cyclopropyl-2-(2-methyl-4-p-tolyl-6,7,8,9-tetrahydrobenzo[g]quinolin-3-yl)propanoic acid
2-(3-methyl-1-p-tolyl-8,9-dihydro-7H-cyclopenta[f]quinolin-2-yl)pentanoic acid
2-(3-methyl-1-p-tolyl-7,8,9,10-tetrahydrobenzo[f]quinolin-2-yl)-3-phenylpropanoic acid
2-(2-methyl-4-p-tolyl-7,8-dihydro-6H-cyclopenta[g]quinolin-3-yl)-3-phenylpropanoic acid
2-(2-oxo-1-propyl-4-p-tolyl-2,6,7,8-tetrahydro-1H-cyclopenta[g]quinolin-3-yl)pentanoic acid
2-(3-oxo-4-propyl-1-p-tolyl-4,7,8,9-tetrahydro-3H-cyclopenta[f]quinolin-2-yl)pentanoic acid
4-methoxy-2-(2-methyl-4-(6-methylpyridin-3-yl)-7,8-dihydro-6H-cyclopenta[g]quinolin-3-yl)butanoic acid
2-tert-butoxy-2-[4-(4-chloro-2-fluorophenyl)-2-methyl-6,8-dihydrofuro[3,4-g]quinolin-3-yl]acetic acid
2-(4-(2-hydroxy-4-methylphenyl)-2-methyl-7,8-dihydro-6H-cyclopenta[g]quinolin-3-yl)pentanoic acid
2-(2-methyl-4-(6-methylpyridin-3-yl)-7,8-dihydro-6H-cyclopenta[g]quinolin-3-yl)pentanoic acid
2-(4-(2,3-dihydropyrano[4,3,2-de]quinolin-7-yl)-2-methyl-7,8-dihydro-6H-cyclopenta[g]quinolin-3-yl)pentanoic acid
2-(4-(benzo[d]thiazol-6-yl)-2-methyl-7,8-dihydro-6H-cyclopenta[g]quinolin-3-yl)pentanoic acid
2-(2-hydroxy-4-p-tolylpyrimido[1,2-b]indazol-3-yl)pentanoic acid
2-(4-(8-fluoro-5-methylchroman-6-yl)-2-methylpyrimido[1,2-b]indazol-3-yl)pentanoic acid
2-(2-methyl-4-(1-methyl-1H-pyrazol-4-yl)pyrimido[1,2-b]indazol-3-yl)pentanoic acid
2-(4-(2-hydroxy-4-methylphenyl)-2-methylpyrimido[1,2-b]indazol-3-yl)pentanoic acid
2-(2-methyl-4-(piperidin-1-yl)pyrimido[1,2-b]indazol-3-yl)pentanoic acid
2-(2-phenyl-4-p-tolylpyrimido[1,2-b]indazol-3-yl)pentanoic acid
2-(1-benzyl-2-oxo-4-p-tolyl-1,2-dihydropyrimido[1,2-b]indazol-3-yl)pentanoic acid
2-tert-butoxy-2-(2-methyl-4-p-tolylpyrimido[1,2-b]indazol-3-yl)acetic acid
2-(2-oxo-1-propyl-4-p-tolyl-1,2-dihydropyrimido[1,2-b]indazol-3-yl)pentanoic acid
2-(4-(benzo[d]thiazol-6-yl)-2-methylpyrimido[1,2-b]indazol-3-yl)pentanoic acid
2-(2-methyl-4-p-tolyl-7,8,9,10-tetrahydropyrimido[1,2-b]indazol-3-yl)pentanoic acid
2-(2-methyl-4-(phenylamino)pyrimido[1,2-b]indazol-3-yl)pentanoic acid 6,6,6-trifluoro-2-(2-methyl-4-(phenylthio)pyrimido[1,2-b]indazol-3-yl)hexanoic acid 2-(2-methyl-4-p-tolylpyrimido[1,2-b]indazol-3-yl)pentanoic acid 2-(4-(4-chloro-2-fluorophenyl)-2-ethylpyrimido[1,2-b]indazol-3-yl)pentanoic acid 2-(1-methyl-2-oxo-4-p-tolyl-1,2-dihydropyrimido[1,2-b]indazol-3-yl)pentanoic acid 2-tert-butoxy-2-(4-(2,3-dihydropyrano[4,3,2-de]quinolin-7-yl)-2-methylpyrimido[1,2-b]indazol-3-yl)acetic acid 2-(7-fluoro-2-methyl-4-p-tolylpyrimido[1,2-b]indazol-3-yl)pentanoic acid 2-(2-methyl-4-phenoxypyrimido[1,2-b]indazol-3-yl)pentanoic acid 3-cyclopropyl-2-(9-methoxy-2-methyl-4-(1-methyl-1H-pyrazol-4-yl)pyrimido[1,2-b]indazol-3-yl)propanoic acid 2-(2-methyl-4-p-tolylpyrimido[1,2-b]indazol-3-yl)-3-phenylpropanoic acid 2-tert-butoxy-2-(2-methyl-4-p-tolyl-5,6,7,8-tetrahydropyridino[1,2-b]imidazo[4,5-b]pyridin-3-yl)acetic acid 2-(4-(benzo[d]thiazol-6-yl)-2-methyl-5,6,7,8-tetrahydropyridino[1,2-b]imidazo[4,5-b]pyridin-3-yl)pentanoic acid 2-(2-methyl-4-phenoxy-5,6,7,8-tetrahydropyridino[1,2-b]imidazo[4,5-b]pyridin-3-yl)pentanoic acid 2-(2-methyl-4-p-tolyl-pyrrolidino[1,2-b]imidazo[4,5-b]pyridin-3-yl)-3-phenylpropanoic acid 2-(2-methyl-4-(piperidin-1-yl)-pyrrolidino[1,2-b]imidazo[4,5-b]pyridin-3-yl)pentanoic acid 2-(1-benzyl-2-oxo-4-p-tolyl-5,6,7,8-tetrahydropyridino[1,2-b]imidazo[4,5-b]pyridin-3-yl)pentanoic acid 2-(2-methyl-4-phenylamino-pyrrolidino[1,2-b]imidazo[4,5-b]pyridin-3-yl)pentanoic acid 2-(1-methyl-2-oxo-4-p-tolyl-pyrrolidino[1,2-b]imidazo[4,5-b]pyridin-3-yl)pentanoic acid 2-(2-methyl-4-phenoxy-pyrrolidino[1,2-b]imidazo[4,5-b]pyridin-3-yl)pentanoic acid 2-(2-oxo-1-propyl-4-p-tolyl-5,6,7,8-tetrahydropyridino[1,2-b]imidazo[4,5-b]pyridin-3-yl)pentanoic acid 2-(4-(4-chloro-2-fluorophenyl)-2-methyl-5,6,7,8-tetrahydropyridino[1,2-b]imidazo[4,5-b]pyridin-3-yl)pentanoic acid 2-(1-benzyl-2-oxo-4-p-tolyl-pyrrolidino[1,2-b]imidazo[4,5-b]pyridin-3-yl)pentanoic acid 2-(4-(2-hydroxy-4-methylphenyl)-2-methyl-5,6,7,8-tetrahydropyridino[1,2-b]imidazo[4,5-b]pyridin-3-yl)pentanoic acid 2-(2-methyl-4-(2-methylpyridin-5-yl)-5,6,7,8-tetrahydropyridino[1,2-b]imidazo[4,5-b]pyridin-3-yl)pentanoic acid 2-(2-methyl-4-p-tolyl-5,6,7,8-tetrahydropyridino[1,2-b]imidazo[4,5-b]pyridin-3-yl)pentanoic acid 2-(4-(8-fluoro-5-methylchroman-6-yl)-2-methyl-5,6,7,8-tetrahydropyridino[1,2-b]imidazo[4,5-b]pyridin-3-yl)pentanoic acid 2-(2-hydroxy-4-p-tolyl-pyrrolidino[1,2-b]imidazo[4,5-b]pyridin-3-yl)pentanoic acid 2-(2-methyl-4-p-tolyl-pyrrolidino[1,2-b]imidazo[4,5-b]pyridin-3-yl)pentanoic acid 2-(4-p-tolyl-2-trifluoromethyl-pyrrolidino[1,2-b]imidazo[4,5-b]pyridin-3-yl)pentanoic acid 2-(4-(8-fluoro-5-methylchroman-6-yl)-2-methyl-pyrrolidino[1,2-b]imidazo[4,5-b]pyridin-3-yl)pentanoic acid 2-(2-methyl-4-(piperidin-1-yl)-5,6,7,8-tetrahydropyridino[1,2-b]imidazo[4,5-b]pyridin-3-yl)pentanoic acid 2-(2-methyl-4-phenylamino-5,6,7,8-tetrahydropyridino[1,2-b]imidazo[4,5-b]pyridin-3-yl)pentanoic acid 2-(2-methyl-4-(1-methyl-1H-pyrazol-4-yl)-pyrrolidino[1,2-b]imidazo[4,5-b]pyridin-3-yl)pentanoic acid 2-(2-methyl-4-phenylthio-pyrrolidino[1,2-b]imidazo[4,5-b]pyridin-3-yl)pentanoic acid 2-((3,4-dimethylphenyl)-2-methyl-pyrrolidino[1,2-b]imidazo[4,5-b]pyridin-3-yl)pentanoic acid 2-(4-(2,3-dihydropyrano[4,3,2-de]quinolin-7-yl)-2-methyl-pyrrolidino[1,2-b]imidazo[4,5-b]pyridin-3-yl)pentanoic acid 2-(2-phenyl-4-p-tolyl-pyrrolidino[1,2-b]imidazo[4,5-b]pyridin-3-yl)pentanoic acid 5,5,5-trifluoro-[4-(benzo[d]thiazol-6-yl)-2oxo-1-propyl-5,6,7,8-tetrahydro[1]benzothieno[2,3-b]pyridin-3-yl]pentanoic acid

[1-propyl-2-oxo-4-(2-methylpyridin-5-yl)-5,6,7,8-tetrahydro[1]benzothieno[2,3-b]pyridin-3-yl]-4-methoxybutanoic acid

[1-methyl-2-oxo-4-p-tolyl-5,6,7,8-tetrahydro[1]benzothieno[2,3-b]pyridin-3-yl]pentanoic acid

[4-(2,3-dihydropyrano[4,3,2-de]quinolin-7-yl)-1-methyl-2-oxo-5,6,7,8-tetrahydro[1]benzothieno[2,3-b]pyridin-3-yl]pentanoic acid

[2-oxo-1-propyl-4-p-tolyl-5,6,7,8-tetrahydro[1]benzothieno[2,3-b]pyridin-3-yl]pentanoic acid 2-tert-butoxy-[1-benzyl-2-oxo-4-p-tolyl-5,6,7,8-tetrahydro[1]benzothieno[2,3-b]pyridin-3-yl]pentanoic acid

[1-benzyl-4-(1-methyl-1H-pyrazol-4-yl)-2-oxo-5,6,7,8-tetrahydro[1]benzothieno[2,3-b]pyridin-3-yl]pentanoic acid

[1-ethyl-4-(2-hydroxy-4-methylphenyl)-2-oxo-5,6,7,8-tetrahydro[1]benzothieno[2,3-b]pyridin-3-yl]butanoic acid 2-tert-butoxy-[2-oxo-1-propyl-4-p-tolyl-5,6,7,8-tetrahydro[1]benzothieno[2,3-b]pyridin-3-yl]acetic acid

[1-benzyl-2-oxo-4-p-tolyl-5,6,7,8-tetrahydro[1]benzothieno[2,3-b]pyridin-3-yl]pentanoic acid

[4-(benzofuran-2-yl)-1-methyl-2-oxo-5,6,7,8-tetrahydro[1]benzothieno[2,3-b]pyridin-3-yl]pentanoic acid 2-ethoxy-[1-methyl-2-oxo-4-p-tolyl-5,6,7,8-tetrahydro[1]benzothieno[2,3-b]pyridin-3-yl]pentanoic acid 2-[2-oxo-1-propyl-4-p-tolyl-6,7-dihydro-5H-cyclopenta[4,5]thieno[2,3-b]pyridin-3-yl]pentanoic acid 2-[1-methyl-2-oxo-4-(p-tolyl)-5,8-dihydro-6H-7-oxa-9-thia-1-aza-fluoren-3-yl]pent-4,5-enoic acid 4-methoxy-2-[1-methyl-2-oxo-4-(2-methylpyridin-5-yl)benzo[4,5]thieno[2,3-b]pyridin-3-yl]butanoic acid 2-(4-(2-fluoro-4-methylphenyl)-2-oxo-1-propyl-1,2,6,7,8,9-hexahydrobenzo[b][1,8]naphthyridin-3-yl)pentanoic acid 6,6,6-trifluoro-2-(2-methyl-4-(6-methylpyridin-3-yl)-6,7,8,9-tetrahydrobenzo[b][1,8]naphthyridin-3-yl)hexanoic acid 2-(1-benzyl-2-oxo-4-p-tolyl-1,2,6,7,8,9-hexahydrobenzo[b][1,8]naphthyridin-3-yl)pentanoic acid 2-(7-fluoro-2-oxo-1-propyl-4-p-tolyl-1,2-dihydrobenzo[b][1,8]naphthyridin-3-yl)pentanoic acid 6,6,6-trifluoro-2-(2-methyl-4-(6-methylpyridin-3-yl)benzo[b][1,8]naphthyridin-3-yl)hexanoic acid 2-(2-hydroxy-4-p-tolyl-6,7,8,9-tetrahydrobenzo[b][1,8]naphthyridin-3-yl)pentanoic acid 2-(1-methyl-2-oxo-4-p-tolyl-1,2,6,7,8,9-hexahydrobenzo[b][1,8]naphthyridin-3-yl)pentanoic acid 2-tert-butoxy-2-(4-(8-fluoro-5-methylchroman-6-yl)-2-methyl-6,7,8,9-tetrahydrobenzo[b][1,8]naphthyridin-3-yl)acetic acid 2-tert-butoxy-2-(7,8-dimethoxy-2-methyl-4-p-tolylbenzo[b][1,8]naphthyridin-3-yl)acetic acid 2-(1-methyl-2-oxo-4-p-tolyl-1,2-dihydrobenzo[b][1,8]naphthyridin-3-yl)pentanoic acid 2-(2-ethyl-4-p-tolylbenzo[b][1,8]naphthyridin-3-yl)pentanoic acid 4-methoxy-2-(2-methyl-4-p-tolylbenzo[b][1,8]naphthyridin-3-yl)butanoic acid
4-methoxy-2-(2-methyl-4-p-tolyl-6,7,8,9-tetrahydrobenzo[b][1,8]naphthyridin-3-yl)butanoic acid
2-(2-hydroxy-4-p-tolylbenzo[b][1,8]naphthyridin-3-yl)pentanoic acid
2-(4-(benzo[d]thiazol-6-yl)-2-methylbenzo[b][1,8]naphthyridin-3-yl)-2-tert-butoxyacetic acid
[2-oxo-1-propyl-4-p-tolyl-5,6,7,8-tetrahydro[1]benzothieno[3,2-b]pyridin-3-yl]pentanoic acid
[1-benzyl-2-oxo-4-p-tolyl-5,6,7,8-tetrahydro[1]benzothieno[3,2-b]pyridin-3-yl]pentanoic acid
[2-methyl-4-(2-methylpyridin-5-yl)-5,6,7,8-tetrahydro[1]benzothieno[3,2-b]pyridin-3-yl]pentanoic acid
[2-hydroxy-4-p-tolyl-5,6,7,8-tetrahydro[1]benzothieno[3,2-b]pyridin-3-yl]pentanoic acid
6,6,6-trifluoro-[4-(4-chlorophenyl)-2-methyl-5,6,7,8-tetrahydro[1]benzothieno[3,2-b]pyridin-3-yl]hexanoic acid
[2-ethyl-4-(1-methyl-1H-pyrazol-4-yl)-5,6,7,8-tetrahydro[1]benzothieno[3,2-b]pyridin-3-yl]pentanoic acid
[4-(2,3-dihydropyrano[4,3,2-de]quinolin-7-yl)-2-methyl-5,6,7,8-tetrahydro[1]benzothieno[3,2-b]pyridin-3-yl]pentanoic acid
[2-methyl-4-phenylthio-5,6,7,8-tetrahydro[1]benzothieno[3,2-b]pyridin-3-yl]pentanoic acid
[2-methyl-4-phenoxy-5,6,7,8-tetrahydro[1]benzothieno[3,2-b]pyridin-3-yl]pentanoic acid
4-methoxy-2-[1-(3,4-dimethylphenyl)-3-methyl-5,8-dihydro-7H-9-thia-4,6-diaza-fluoren-2-yl]butanoic acid
[2-methyl-4-(1-piperidinyl)-tolyl-5,6,7,8-tetrahydro[1]benzothieno[3,2-b]pyridin-3-yl]pentanoic acid
[1-methyl-2-oxo-4-p-tolyl-5,6,7,8-tetrahydro[1]benzothieno[3,2-b]pyridin-3-yl]pentanoic acid
[4-(benzo[d]thiazol-6-yl)-2-methyl-5,6,7,8-tetrahydro[1]benzothieno[3,2-b]pyridin-3-yl]pentanoic acid
[4-(2-fluoro-4-methylphenyl)-2-methyl-5,6,7,8-tetrahydro[1]benzothieno[3,2-b]pyridin-3-yl]pentanoic acid
2-ter-butoxy-[4-(8-fluoro-5-methylchroman-6-yl)-2-methyl-5,6,7,8-tetrahydro[1]benzothieno[3,2-b]pyridin-3-yl]acetic acid
2-tert-butoxy-2-[2-methyl-4-p-tolyl-6,7-dihydro-5H-cyclopenta[4,5]thieno[3,2-b]pyridin-3-yl]pentanoic acid
2-[2-methyl-4-(2-fluoro-4-methylphenyl)benzo[4,5]thieno[3,2-b]pyridin-3-yl]pentanoic acid
2-[3-methyl-1-p-tolyl-5,8-dihydro-7H-9-thia-6-oxa-4-aza-fluoren-2-yl]pent-4,5-enoic acid
2-tert-butoxy-[2-methyl-4-p-tolyl-benzimidazo[3,2-b]pyrimidin-3-yl]acetic acid
[7-methoxy-1-methyl-2-oxo-4-p-tolyl-benzimidazo[3,2-b]pyrimidin-3-yl]pentanoic acid
2-tert-butoxy-[4-(benzo[d]thiazol-6-yl)-2-methyl-benzimidazo[3,2-b]pyrimidin-3-yl]acetic acid
[4-(2-fluoro-4-methylphenyl)-2-methyl-benzimidazo[3,2-b]pyrimidin-3-yl]pentanoic acid
[2-methyl-4-phenylamino-benzimidazo[3,2-b]pyrimidin-3-yl]pentanoic acid
4-methoxy-[2-methyl-4-(2-methyl-pyridin-5-yl)-benzimidazo[3,2-b]pyrimidin-3-yl]butanoic acid
[2-hydroxy-4-p-tolyl-7-trifluoromethyl-benzimidazo[3,2-b]pyrimidin-3-yl]pentanoic acid
[2-ethyl-4-p-tolyl-5,6,7,8-tetrahydro[1]benzimidazo[3,2-b]pyrimidin-3-yl]pentanoic acid
[4-(2,3-dihydropyrano[4,3,2-de]quinolin-7-yl)-2-methyl-benzimidazo[3,2-b]pyrimidin-3-yl]pentanoic acid
[2-methyl-4-phenoxy-benzimidazo[3,2-b]pyrimidin-3-yl]pentanoic acid
[2-phenyl-4-p-tolyl-benzimidazo[3,2-b]pyrimidin-3-yl]pentanoic acid
[4-(8-fluoro-5-methylchroman-6-yl)-2-methyl-benzimidazo[3,2-b]pyrimidin-3-yl]pentanoic acid
[2-hydroxy-1-propyl-4-p-tolyl-benzimidazo[3,2-b]pyrimidin-3-yl]pentanoic acid
[4-(2-hydroxy-4-methylphenyl)-2,6,7-trimethyl-benzimidazo[3,2-b]pyrimidin-3-yl]pentanoic acid
6,6,6-trifluoro-[2-methyl-4-p-tolyl-5,6,7,8-tetrahydro[1]benzimidazo[3,2-b]pyrimidin-3-yl]hexanoic acid
[4-p-tolyl-2-trifluoromethyl-benzimidazo[3,2-b]pyrimidin-3-yl]pentanoic acid
[2-methyl-4-(piperidin-1yl)-benzimidazo[3,2-b]pyrimidin-3-yl]pentanoic acid
[2-methyl-4-phenylthio-benzimidazo[3,2-b]pyrimidin-3-yl]pentanoic acid
2-(2-oxo-1-propyl-4-p-tolyl-2,5,6,7,8,9-hexahydro-1H-pyrido[2,3-b]indol-3-yl)pentanoic acid
2-(2-methyl-4-(1-methyl-1H-pyrazol-4-yl)-9-phenyl-6,7,8,9-tetrahydro-5H-pyrido[2,3-b]indol-3-yl)pentanoic acid
4-methoxy-2-(2-methyl-4-p-tolyl-6,7,8,9-tetrahydro-5H-pyrido[2,3-b]indol-3-yl)butanoic acid
2-(1,9-dimethyl-2-oxo-4-p-tolyl-2,5,6,7,8,9-hexahydro-1H-pyrido[2,3-b]indol-3-yl)pentanoic acid
2-(2-phenyl-4-p-tolyl-6,7,8,9-tetrahydro-5H-pyrido[2,3-b]indol-3-yl)pentanoic acid
2-tert-butoxy-2-(2-methyl-4-(6-methylpyridin-3-yl)-6,7,8,9-tetrahydro-5H-pyrido[2,3-b]indol-3-yl)acetic acid
2-(2-hydroxy-4-p-tolyl-6,7,8,9-tetrahydro-5H-pyrido[2,3-b]indol-3-yl)pentanoic acid
2-(2-ethyl-4-p-tolyl-6,7,8,9-tetrahydro-5H-pyrido[2,3-b]indol-3-yl)pentanoic acid
2-tert-butoxy-(2-methyl-4-p-tolyl-6,7,8,9-tetrahydro-benzo[b][1,8]naphthyridin-3-yl)-acetic acid
2-tert-butoxy-(2-methyl-4-p-tolyl-benzo[b][1,8]naphthyridin-3-yl)-acetic acid
2-(2-methyl-4-p-tolyl-6,7,8,9-tetrahydro-dipyrido[1,2-a;3',2'-d]imidazol-3-yl)-pentanoic acid, and
2-(2-methyl-4-p-tolyl-6,7,8,9-tetrahydro-benzo[4,5]imidazo[1,2-a]pyrimidin-3-yl)-pentanoic acid
and the pharmaceutically acceptable salts thereof.

According to a second aspect, the invention relates to the compounds as described herein for use as a medicament or a medicine, more in particular for use as an antiviral medicament and for the use in the prevention or treatment of a viral infection in a subject (animal, mammal or human). The present invention also relates to the use of compounds of the formulae and embodiments described herein (including but not limited to formula (A), (A1), (A2), (B), (B1), (B2), (C1), (C2), (C3), (C4), (C5), (C6), (C7), (C8), (C9), (C10), (D1), (D2), (E1), (E2), (F1), (F2), (F3), (F4), (G1), (G2), (H1), (H2), (I1), (I2), (J1), (J2), (J3), and (J4) and claims herein as antiviral compounds, more particularly as compounds active against retroviruses, yet more in particular against HIV. The invention also relates to the use of the compounds of the invention for the manufacture of a medicament or as a pharmaceutically active ingredient, especially as a virus replication inhibitor, for instance for the manufacture of a medicament or pharmaceutical composition having antiviral activity for the prevention and/or treatment of viral infections in humans, mammals and animals in general. The present invention further relates to a method of prevention or treatment of a viral infection, preferably a retroviral infection in an animal, including mammals, including a human, comprising administering to the animal in need of such treatment a therapeutically effective amount of a compound of the invention as an active ingredient, preferably in admixture with at least a pharmaceutically acceptable carrier.

Yet another aspect of the present invention relates to pharmaceutical compositions comprising the compounds of the invention according to formulae and claims herein in admixture with at least a pharmaceutically acceptable carrier and to the use of these compositions for the treatment of subjects (being animals, mammals or humans) suffering from a viral infection, in particular a retroviral infection, especially HIV infection.

The invention further relates to (a) one or more compounds of the invention (of formulae, embodiments and claims herein), and (b) one or more additional viral inhibitors in the form of a combined preparation for simultaneous, separate or sequential use in viral infection therapy. Within the framework of this embodiment of the invention, the viral inhibitors used as a therapeutically active ingredients (b) may belong to categories already known in the art. In a particular embodiment, the compounds of the present invention can be combined with one or more of the following compounds:
- nucleoside reverse transcriptase (RT) inhibitors such as, but not limited to, azidothymidine (AZT), and lamivudine (3TC);
- nucleotide reverse transcriptase inhibitors such as, but not limited to, tenofovir (R-PMPA);
- non-nucleoside reverse transcriptase inhibitors such as, but not limited to, nevirapine, efavirenz, and lersivirine;
- protease inhibitors such as, but not limited to, nelfinavir, saquinavir, ritonavir and amprenavir;
- fusion inhibitors such as, but not limited to, enfuvirtide; or integrase inhibitors such as, but not limited to, raltegravir or elvitegravir.

More generally, the invention relates to the compounds of formulae, embodiments and claims herein being useful as agents having biological activity or as diagnostic agents. Any of the uses mentioned with respect to the present invention may be restricted to a non-medical use, a non-therapeutic use, a non-diagnostic use, or exclusively an in vitro use, or a use related to cells remote from an animal.

The invention further relates to the use of the compounds of the invention as chemical tools for virology and biochemistry. In particular, they can be used as research tools to investigate HIV biology.

DETAILED DESCRIPTION OF THE INVENTION

The terminology "one or more —$CH_3$, —$CH_2$—, —CH= and/or =CH is optionally replaced by one or more —$NH_2$, —NH—, —O—, —S—, —N= and/or =N" as used herein, means that —$CH_3$ can be replaced by $NH_2$; —$CH_2$— by —NH—, —O— or —S—; —CH= by —N=; and CH by N. This term therefore comprises, depending on the group to which is referred, as an example alkoxy, alkenyloxy, alkynyloxy, alkyl-O-alkylene, alkenyl-O-alkylene, arylalkoxy, benzyloxy, heterocycle-heteroalkyl, heterocycle-alkoxy, among others. The terminology therefore refers to heteroalkyl, meaning an alkyl which comprises one or more heteroatoms in the hydrocarbon chain, whereas the heteroatoms may be positioned at the beginning of the hydrocarbon chain, in the hydrocarbon chain or at the end of the hydrocarbon chain.

Examples of heteroalkyl include methoxy, methylthio, ethoxy, propoxy, $CH_3$—O—$CH_2$—, $CH_3$—S—$CH_2$—, $CH_3$—$CH_2$—O—$CH_2$—, $CH_3$—NH—, $(CH_3)_2$—N—, $(CH_3)_2$—$CH_2$—NH—$CH_2$—$CH_2$—, among many other examples. As an example, the terminology "arylalkyl wherein one or more —$CH_3$, —$CH_2$—, —CH= and/or =CH is optionally replaced by one or more —$NH_2$, —NH—, —O—, —S—, —N= and/or =N" therefore refers to arylheteroalkyl, meaning an arylalkyl which comprises one or more heteroatoms in the hydrocarbon chain, whereas the heteroatoms may be positioned at the beginning of the hydrocarbon chain, in the hydrocarbon chain or at the end of the hydrocarbon chain. "Arylheteroalkyl" thus includes aryloxy, arylalkoxy, aryl-alkyl-NH— and the like and examples are phenyloxy, benzyloxy, aryl-$CH_2$—S—$CH_2$—, aryl-$CH_2$—O—$CH_2$—, aryl-NH—$CH_2$-among many other examples. The same counts for "heteroalkenyl", "heteroalkynyl", and other terms used herein when referred to "wherein one or more —$CH_3$, —$CH_2$—, —CH= and/or =CH is optionally replaced by one or more —$NH_2$, —NH—, —O—, —S—, —N= and/or =N". As used herein and unless otherwise stated, the expression "wherein said 5, 6 or 7-membered unsaturated ring optionally includes one or more heteroatoms, said heteroatoms being selected from the atoms O, S and N" means any 5, 6 or 7-membered unsaturated cycloalkyl moiety, any 5, 6 or 7-membered aryl moiety, and any 5, 6 or 7-membered mono-unsaturated, multi-unsaturated or aromatic O, S and/or N containing heterocycle.

The terminology regarding a chemical group "wherein optionally a carbon atom or heteroatom can be oxidized to form a C=O, C=S, N=O, N=S, S=O or $S(O)_2$" as used herein, refers to a group wherein a carbon atom or heteroatom of said group can be oxidized to form a C=O, C=S, N=O, N=S, S=O or $S(O)_2$. As an example, the terminology when referring to alkyl includes $CH_3$—C(O)—$CH_2$—, $CH_3$—C(O)—, $CH_3$—C(S)—$CH_2$— and $(CH_3)_2$—$CH_2$—C(O)—$CH_2$—$CH_2$—.

The combination for a group wherein "one or more —$CH_3$, —$CH_2$—, —CH= and/or =CH is optionally replaced by one or more —$NH_2$, —NH—, —O—, —S—, —N= and/or =N" and "wherein optionally a carbon atom or heteroatom can be oxidized to form a C=O, C=S, N=O, N=S, S=O or $S(O)_2$" can combine the two aspects described herein above and includes, if the group referred to is alkyl, among other examples $CH_3$—COO—, $CH_3$—COO—$CH_2$—, $CH_3$—NH—CO—, $CH_3$—NH—CO—$CH_2$—, $CH_3$—NH—CS—$CH_2$—, $CH_3$—NH—CS—NH—$CH_2$—, $CH_3$—NH—$S(O)_2$— and $CH_3$—NH—$S(O)_2$—NH—$CH_2$—.

The term "leaving group" (LG) as used herein means a chemical group which is susceptible to be displaced by a nucleophile or cleaved off or hydrolysed in basic or acidic conditions. In a particular embodiment, a leaving group is selected from a halogen atom (e.g., Cl, Br, I) or a sulfonate (e.g., mesylate, tosylate, triflate).

The term "alkyl" as used herein means $C_1$-$C_{18}$ normal, secondary, or tertiary, linear or cyclic, branched or straight hydrocarbon with no site of unsaturation. Examples are methyl, ethyl, 1-propyl, 2-propyl, 1-butyl, 2-methyl-1-propyl (i-Bu), 2-butyl (s-Bu), 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl. In a particular embodiment, the term alkyl refers to $C_{1-12}$ hydrocarbons, yet more in particular to $C_{1-6}$ hydrocarbons as further defined herein above.

The term "linear alkyl" as used herein means $C_1$-$C_{18}$ normal, secondary, or tertiary, linear, branched or straight, hydrocarbon with no site of unsaturation. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl.

As used herein and unless otherwise stated, the term "cycloalkyl" means a monocyclic saturated hydrocarbon monovalent radical having from 3 to 10 carbon atoms, such as for instance cyclopropyl, cyclobutyl, cyclopentyl, cyclohexyl, cycloheptyl, cyclooctyl and the like, or a $C_{7-10}$ polycyclic saturated hydrocarbon monovalent radical having from 7 to 10 carbon atoms such as, for instance, norbornyl, fenchyl, trimethyltricycloheptyl or adamantyl.

The term "alkenyl" as used herein is $C_2$-$C_{18}$ normal, secondary or tertiary, linear or cyclic, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$), cyclopentenyl (—C$_5$H$_7$), cyclohexenyl (—C$_6$H$_9$) and 5-hexenyl (—CH$_2$CH$_2$CH$_2$CH$_2$CH=CH$_2$). The double bond may be in the cis or trans configuration. In a particular embodiment, the term alkenyl refers to $C_{1-12}$ hydrocarbons, yet more in particular to $C_{1-6}$ hydrocarbons as further defined herein above.

The term "linear alkenyl" as used herein refers to $C_2$-$C_{18}$ normal, secondary or tertiary, linear, branched or straight hydrocarbon with at least one site (usually 1 to 3, preferably 1) of unsaturation, namely a carbon-carbon, sp2 double bond. Examples include, but are not limited to: ethylene or vinyl (—CH=CH$_2$), allyl (—CH$_2$CH=CH$_2$) and 5-hexenyl (—CH$_2$CH$_2$CH$_2$CH$_2$CH=CH$_2$). The double bond may be in the cis or trans configuration.

The term "cycloalkenyl" as used herein refers to $C_4$-$C_{18}$ normal, secondary or tertiary, cyclic hydrocarbon with at least one site (usually 1 to 3, preferably 1) of unsaturation, namely a carbon-carbon, sp2 double bond. Examples include, but are not limited to: cyclopentenyl (—C$_5$H$_7$) and cyclohexenyl (—C$_6$H$_9$). The double bond may be in the cis or trans configuration.

The term "alkynyl" as used herein refers to $C_2$-$C_{18}$ normal, secondary, tertiary, linear or cyclic, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—CH$_2$C≡CH). In a particular embodiment, the term alkenyl refers to $C_{1-12}$ hydrocarbons, yet more in particular to $C_{1-6}$ hydrocarbons as further defined herein above.

The term "linear alkynyl" as used herein refers to $C_2$-$C_{18}$ normal, secondary, tertiary, linear, branched or straight hydrocarbon with at least one site (usually 1 to 3, preferably 1) of unsaturation, namely a carbon-carbon, sp triple bond. Examples include, but are not limited to: acetylenic (—C≡CH) and propargyl (—CH$_2$C≡CH).

The term "cycloalkynyl" as used herein refers to $C_5$-$C_{18}$ normal, secondary, tertiary, cyclic hydrocarbon with at least one site (usually 1 to 3, preferably 1) of unsaturation, namely a carbon-carbon, sp triple bond. Examples include, but are not limited to: cyclohex-1-yne and ethylene-cyclohex-1-yne.

The terms "alkylene" as used herein each refer to a saturated, branched or straight chain hydrocarbon radical of 1-18 carbon atoms (more in particular 1-12 or 1-6 carbon atoms), and having two monovalent radical centers derived by the removal of two hydrogen atoms from the same or two different carbon atoms of a parent alkane. Typical alkylene radicals include, but are not limited to: methylene (—CH$_2$—) 1,2-ethyl (—CH$_2$CH$_2$—), 1,3-propyl (—CH$_2$CH$_2$CH$_2$—), 1,4-butyl (—CH$_2$CH$_2$CH$_2$CH$_2$—), and the like.

The term "aryl" as used herein means an aromatic hydrocarbon radical of 6-20 carbon atoms derived by the removal of hydrogen from a carbon atom of a parent aromatic ring system. Typical aryl groups include, but are not limited to 1 ring, or 2 or 3 rings fused together, radicals derived from benzene, naphthalene, anthracene, biphenyl, and the like. In a particular embodiment, the term "parent aromatic ring system" means a monocyclic aromatic ring system or a bi- or tricyclic ring system of which at least one ring is aromatic. Therefore, in this embodiment, typical aryl groups include, but are not limited to 1 ring, or 2 or 3 rings fused together, radicals derived from benzene, naphthalene, anthracene, biphenyl, 2,3-dihydro-1H-indenyl, 5,6,7,8-tetrahydronaphthalenyl, 1,2,6,7,8,8a-hexahydroacenaphthylenyl, 1,2-dihydroacenaphthylenyl, and the like. Particular aryl groups are phenyl and naphthyl, especially phenyl.

"Arylalkyl" as used herein refers to an alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety of the arylalkyl group is 1 to 6 carbon atoms and the aryl moiety is 5 to 14 carbon atoms.

"Arylalkenyl" as used herein refers to an alkenyl radical in which one of the hydrogen atoms bonded to a carbon atom, is replaced with an aryl radical. The arylalkenyl group comprises 6 to 20 carbon atoms, e.g. the alkenyl moiety of the arylalkenyl group is 1 to 6 carbon atoms and the aryl moiety is 5 to 14 carbon atoms.

"Arylalkynyl" as used herein refers to an alkynyl radical in which one of the hydrogen atoms bonded to a carbon atom, is replaced with an aryl radical. The arylalkynyl group comprises 6 to 20 carbon atoms, e.g. the alkynyl moiety of the arylalkynyl group is 1 to 6 carbon atoms and the aryl moiety is 5 to 14 carbon atoms.

The term "heterocycle" as used herein means a saturated, unsaturated or aromatic ring system including at least one N, O, S, or P. Heterocycle thus includes heteroaryl groups. Heterocycle as used herein includes by way of example and not limitation those heterocycles described in Paquette, Leo A. "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; Katritzky, Alan R., Rees, C. W. and Scriven, E. "Comprehensive Heterocyclic Chemistry" (Pergamon Press, 1996); and J. Am. Chem. Soc. (1960) 82:5566. In a particular embodiment, the term means pyridyl, dihydroypyridyl, tetrahydropyridyl (piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl, isatinoyl, 2,3-dihydropyrano[4,3,2-de]quinolinyl, chromanyl, 3,4-dihydro-2H-benzo[b][1,4]oxazinyl, 1,2,3,4-tetrahydroquinolinyl and 2,3-dihydrobenzofuranyl, preferably it means pyridyl, dihydroypyridyl, tetrahydropyridyl(piperidyl), thiazolyl, tetrahydrothiophenyl, sulfur oxidized tetrahydrothiophenyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, benzothienyl, benzothiazolyl, or isatinoyl.

"Heterocycle-alkyl" as used herein refers to an alkyl radical in which one of the hydrogen atoms bonded to a carbon atom, typically a terminal or sp3 carbon atom, is replaced with a heterocyle radical. An example of a heterocycle-alkyl group is 2-pyridyl-methylene. The heterocycle-alkyl group comprises 6 to 20 carbon atoms, e.g. the alkyl moiety of the heterocycle-alkyl group is 1 to 6 carbon atoms and the heterocycle moiety is 5 to 14 carbon atoms.

"Heterocycle-alkenyl" as used herein refers to an alkenyl radical in which one of the hydrogen atoms bonded to a carbon atom, is replaced with an heterocycle radical. The heterocycle-alkenyl group comprises 6 to 20 carbon atoms, e.g. the alkenyl moiety of the heterocycle-alkenyl group is 1 to 6 carbon atoms and the heterocycle moiety is 5 to 14 carbon atoms.

"Heterocycle-alkynyl" as used herein refers to an alkynyl radical in which one of the hydrogen atoms bonded to a carbon atom, is replaced with a heterocycle radical. The heterocycle-alkynyl group comprises 6 to 20 carbon atoms, e.g. the alkynyl moiety of the heterocycle-alkynyl group is 1 to 6 carbon atoms and the heterocycle moiety is 5 to 14 carbon atoms.

"Heteroaryl" means an aromatic ring system including at least one N, O, S, or P. Examples of heteroaryl include but are not limited to pyridyl, dihydropyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, and pyrrolyl.

"Heteroaryl-alkyl" as used herein refers to an alkyl radical in which one of the hydrogen atoms bonded to a carbon atom, typically a terminal or sp3 carbon atom, is replaced with a heterocyle radical. An example of a heteroaryl-alkyl group is 2-pyridyl-methylene. The heteroaryl-alkyl group comprises 6 to 20 carbon atoms, e.g. the alkyl moiety of the heteroaryl-alkyl group is 1 to 6 carbon atoms and the heteroaryl moiety is 5 to 14 carbon atoms.

"Heteroaryl-alkenyl" as used herein refers to an alkenyl radical in which one of the hydrogen atoms bonded to a carbon atom, is replaced with an heteroaryl radical. The heteroaryl-alkenyl group comprises 6 to 20 carbon atoms, e.g. the alkenyl moiety of the heteroaryl-alkenyl group is 1 to 6 carbon atoms and the heteroaryl moiety is 5 to 14 carbon atoms.

"Heteroaryl-alkynyl" as used herein refers to an alkynyl radical in which one of the hydrogen atoms bonded to a carbon atom, is replaced with a heteroaryl radical. The heteroaryl-alkynyl group comprises 6 to 20 carbon atoms, e.g. the alkynyl moiety of the heteroaryl-alkynyl group is 1 to 6 carbon atoms and the heteroaryl moiety is 5 to 14 carbon atoms.

By way of example, carbon bonded heterocyclic rings are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example, nitrogen bonded heterocyclic rings are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

As used herein and unless otherwise stated, the terms "alkoxy", "cycloalkoxy", "aryloxy", "arylalkyloxy", "oxyheterocycle ring", "thio-alkyl", "thio-cycloalkyl", "arylthio", "arylalkylthio" and "thioheterocyce" refer to substituents wherein an alkyl radical, respectively a cycloalkyl, aryl, arylalkyl or heterocycle radical (each of them such as defined herein), are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like. The same definitions will apply for alkenyl and alkynyl radicals in stead of alkyl.

As used herein and unless otherwise stated, the term halogen means any atom selected from the group consisting of fluorine, chlorine, bromine and iodine.

Any substituent designation that is found in more than one site in a compound of this invention shall be independently selected.

Substituents optionally are designated with or without bonds. Regardless of bond indications, if a substituent is polyvalent (based on its position in the structure referred to), then any and all possible orientations of the substituent are intended.

The compounds of the invention are employed for the treatment or prophylaxis of viral infections, more particularly retroviral infections, in particular HIV infections. When using one or more compounds of the invention and of the formulae as defined herein:

the compound(s) may be administered to the animal or mammal (including a human) to be treated by any means well known in the art, i.e. orally, intranasally, subcutaneously, intramuscularly, intradermally, intravenously, intra-arterially, parenterally or by catheterization.

the therapeutically effective amount of the preparation of the compound(s), especially for the treatment of viral infections in humans and other mammals, preferably is a retroviral replication inhibiting amount of the formulae as defined herein and corresponds to an amount which ensures a plasma level of between 1 μg/ml and 100 mg/ml, optionally of 10 mg/ml.

The present invention further relates to a method for preventing or treating a viral infections in a subject or patient by administering to the patient in need thereof a therapeutically effective amount of the compounds of the present invention. The therapeutically effective amount of the compound(s), especially for the treatment of viral infections in humans and other mammals, preferably is a retroviral replication inhibiting amount. The suitable dosage is usually in the range of 0.001 mg to 60 mg, optionally 0.01 mg to 10 mg, optionally 0.1 mg to 1 mg per day per kg bodyweight for humans. Depending upon the pathologic condition to be treated and the patient's condition, the said effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as subsynergistic, and when it is lower than 0.5, the combination is by defined as synergistic. When the minimum FIC index is between 1.0 and 2.0, the combination is defined as subantagonistic and, when it is higher than 2.0, the combination is defined as antagonistic.

This principle may be applied to a combination of different antiviral drugs of the invention or to a combination of the antiviral drugs of the invention with other drugs that exhibit anti-HIV activity.

The invention thus relates to a pharmaceutical composition or combined preparation having synergistic effects against a viral infection and containing:
Either:
A)
(a) a combination of two or more of the compounds of the present invention, and
(b) optionally one or more pharmaceutical excipients or pharmaceutically acceptable carriers,
for simultaneous, separate or sequential use in the treatment or prevention of a retroviral infection
or
B)
(c) one or more anti-viral agents, and
(d) at least one of the compounds of the present invention, and
(e) optionally one or more pharmaceutical excipients or pharmaceutically acceptable carriers,
for simultaneous, separate or sequential use in the treatment or prevention of a retroviral infection.

The agents that may be used in combination with the compounds of the present invention include, but are not limited to, those useful as HIV protease inhibitors, HIV reverse transcriptase inhibitors, non-nucleoside HIV reverse transcriptase inhibitors, HIV integrase inhibitors, CCR5 inhibitors, HIV fusion inhibitors or other inhibitors of HIV entry, maturation inhibitors, agents that act to perturb HIV capsid multimerisation or viral core stability, compounds targeting host proteins required for viral replication or immune evasion (such as but not limited to PSIP1), compounds useful as immunomodulators, compounds that inhibit the HIV virus by an unknown mechanism, compounds useful for the treatment of herpes viruses, compounds useful as anti-infectives, and others as described below.

Compounds useful as HIV protease inhibitors that may be used in combination with the compound of the present invention include, but are not limited to, 141 W94 (amprenavir), CGP-73547, CGP-61755, DMP-450 (mozenavir), nelfinavir, ritonavir, saquinavir (invirase), lopinavir, TMC-126, atazanavir, palinavir, GS-3333, KN I-413, KNI-272, LG-71350, CGP-61755, PD 173606, PD 177298, PD 178390, PD 178392, U-140690, ABT-378, DMP-450, AG-1776, MK-944, VX-478, indinavir, tipranavir, TMC-114 (darunavir), DPC-681, DPC-684, fosamprenavir calcium (Lexiva), benzenesulfonamide derivatives disclosed in WO 03053435, R-944, Ro-03-34649, VX-385 (brecanavir), GS-224338, OPT-TL3, PL-100, SM-309515, AG-148, DG-35-VIII, DMP-850, GW-5950x, KNI-1039, L-756423, LB-71262, LP-130, RS-344, SE-063, UIC-94-003, Vb-19038, A-77003, BMS-182193, BMS-186318, SM-309515, JE-2147, GS-9005, telinavir (SC-52151), BILA-2185 BS, DG-17, PPL-100, A-80987, GS-8374, DMP-323, U-103017, CGP-57813, and CGP-53437.

Compounds useful as inhibitors of the HIV reverse transcriptase enzyme that may be used in combination with the compound of the present invention include, but are not limited to, abacavir, emtricitabine (FTC), GS-840 (adefovir), lamivudine, adefovir dipivoxil, beta-fluoro-ddA, zalcitabine, didanosine, stavudine, zidovudine, tenofovir, tenofovir disoproxil fumarate, amdoxovir, SPD-754 (apricitabine), SPD-756, racivir, reverset (DPC-817), MIV-210 (FLG), beta-L-Fd4C (ACH-126443, elvucitabine), MIV-310 (alovudine, FLT), dOTC, DAPD, entecavir, GS-7340, stampidine, D-d$_4$FC (dexelvucitabine), phospahzide, fozivudine tidoxil, and fosalvudine tidoxil.

Compounds useful as non-nucleoside inhibitors of the HIV reverse transcriptase enzyme that may be used in combination with the compound of the present invention include, but are not limited to, efavirenz, HBY-097, nevirapine, dapivirine (TMC-120), TMC-125, etravirine, delavirdine, DPC-083, DPC-961, TMC-120, capravirine, GW-678248, GW-695634, calanolide, rilpivirine (TMC-278), loviride, emivirine (MKC-442), DPC-963, MIV-150, BILR 355 BS, VRX-840773, lersivirine (UK-453061), RDEA806, and tricyclic pyrimidinone derivatives as disclosed in WO 03062238.

Compounds useful as CCR5 inhibitors that may be used in combination with the compound of the present invention include, but are not limited to, TAK-779, SC-351125, SCH-D, UK-427857 (maraviroc), PRO-140, and GW-873140 (aplaviroc, Ono-4128, AK-602), SCH-417690 (viciviroc, SCH-D), INCB-9471, INCB-15050, TBR-220 (TAK-220), CCR5 mAb004. Other compounds useful as CCR5 inhibitors that may be used in combination with the compound of the present invention include, but are not limited to, (N-{(1S)-3-[3-isopropyl-5-methyl-4H-1,2,4-triazole-4-yl]-exo-8-azabicyclo[3.2.1]oct-8-yl}-1-phenylpropyl)-4,4-difluorocyclohexanecarboxamide), methyl 1-endo-{8-[(3S)-3-(acetylamino)-3-(3-fluorophenyl)propyl]-8-azabicyclo[3.2.1]oct-3-yl}-2-methyl-4,5,6,7-tetrahydro-1H-imidazo[4,5-c]pyridine-5-carboxylate, and N-{(1S)-3-[3-endo-(5-lsobutyryl-2-methyl-4,5,6,7-tetrahydro-1H-imidazo[4,5-c]pyridin-1-yl)-8-azabicyclo[3.2.1]oct-8-yl]-1-(3-fluorophenyl)propyl}acetamide).

Compounds useful as inhibitors of HIV integrase enzyme that may be used in combination with the compound of the present invention include, but are not limited to, raltegravir, elvitegravir (GS-9137, JTK-303), GSK-364735, MK-2048, BMS-707035, S-1360 (GW-810781), L-870810, L-870812, AR-177, BA-011, 1,5-naphthyridine-3-carboxamide derivatives disclosed in WO 03062204, compounds disclosed in WO 03047564, compounds disclosed in WO 03049690, 5-hydroxypyrimidine-4-carboxamide derivatives disclosed in WO 03035076, and L-000810810.

Fusion inhibitors for the treatment of HIV that may be used in combination with the compound of the present invention include, but are not limited to enfuvirtide (T-20), T-1249, AMD-3100, sifuvirtide, FB-006M, TRI-1144, PRO-2000 and fused tricyclic compounds disclosed in JP 2003171381.

Maturation inhibitors for the treatment of HIV that may be used in combination with the compound of the present invention include, but are not limited to bevirimat and vivecon.

HIV fixed drug combinations for the treatment of HIV that may be used in combination with the compound of the present invention include, but are not limited to, combivir, atripla, trizivir, truvada, kaletra and epzicom.

CXCR4 inhibitors for the treatment of HIV that may be used in combination with the compound of the present invention include, but are not limited to, AMD-070.

Entry inhibitors for the treatment of HIV that may be used in combination with the compound of the present invention include, but are not limited to, SP-01A.

Gp 120 inhibitors for the treatment of HIV that may be used in combination with the compound of the present invention include, but are not limited to, BMS-488043 and BMS-378806.

G6PD and NADH-oxidase inhibitors for the treatment of HIV that may be used in combination with the compound of the present invention include, but are not limited to, immunitin.

Other compounds that are useful inhibitors of HIV that may be used in combination with the compound of the present invention include, but are not limited to, Soluble CD4, PRO-542, ibalizumab (TNX-355), and compounds disclosed in JP 2003119137.

Compounds useful in the treatment or management of infection from viruses other than HIV that may be used in combination with the compound of the present invention include, but are not limited to, acyclovir, fomivirsen, penciclovir, HPMPC, oxetanocin G, AL-721, cidofovir, cytomegalovirus immune globin, cytovene, fomivganciclovir, famciclovir, foscarnet sodium, Isis 2922, KNI-272, valacyclovir, virazole ribavirin, valganciclovir, ME-609, PCL-016, DES6, ODN-93, ODN-112, VGV-1, ampligen, HRG-214, cytolin, VGX-410, KD-247, AMZ-0026, CYT-99007A-221, DEBIO-025, BAY 50-4798, MDX-010 (ipilimumab), PBS-119, ALG-889, PA-1050040 (PA-040) and filibuvir (PF-00868554).

Compounds that act as immunomodulators and may be used in combination with the compound of the present invention include, but are not limited to, AD-439, AD-519, Alpha Interferon, AS-101, bropirimine, acemannan, CL246,738, EL10, FP-21399, gamma interferon, granulocyte macrophage colony stimulating factor, IL-2, immune globulin intravenous, IMREG-1, IMREG-2, imuthiol diethyl dithio carbamate, alpha-2 interferon, methionine-enkephalin, MTP-PE, granulocyte colony stimulating sactor, remune, rCD4, recombinant soluble human CD4, interferon alfa-2, SK&F106528, soluble T4 yhymopentin, tumor necrosis factor (TNF), tucaresol, recombinant human interferon beta, and interferon alfa n–3.

Anti-infectives that may be used in combination with the compound of the present invention include, but are not limited to, atovaquone, azithromycin, clarithromycin, trimethoprim, trovafloxacin, pyrimethamine, daunorubicin, clindamycin with primaquine, pastill, ornidyl, eflornithine pentamidine, rifabutin, spiramycin, intraconazole-R51211, trimetrexate, daunorubicin, chloroquine, recombinant human erythropoietin, recombinant human growth hormone, megestrol acetate, testerone, and total enteral nutrition.

Antifungals that may be used in combination with the compound of the present invention include, but are not limited to, anidulafungin, C31G, caspofungin, DB-289, fluconazole, itraconazole, ketoconazole, micafungin, posaconazole, and voriconazole.

Other compounds that may be used in combination with the compound of the present invention include, but are not limited to, acemannan, ansamycin, LM 427, AR177, BMS-232623, BMS-234475, CI-1012, curdlan sulfate, dextran sulfate, STOCRINE ED 0, hypericin, lobucavir, novapren, peptide T octabpeptide sequence, trisodium phosphonoformate, probucol, and RBC-CD4.

In addition, the compound of the present invention may be used in combination with anti-proliferative agents for the treatment of conditions such as Kaposi's sarcoma. Such agents include, but are not limited to, inhibitors of metallomatrix proteases, A-007, bevacizumab, BMS-275291, halofuginone, interleukin-12, rituximab, paclitaxel, porfimer sodium, rebimastat, and COL-3.

According to a particular embodiment of the invention, the compounds of the invention may be employed in combination with other therapeutic agents for the treatment or prophylaxis of retroviral infections, more preferably HIV. The invention therefore relates to the use of a composition comprising:
(a) one or more compounds of the formulae herein, and
(b) one or more retroviral enzyme inhibitors as biologically active agents in respective proportions such as to provide a synergistic effect against a viral infection, particularly a retroviral infection in a mammal, for instance in the form of a combined preparation for simultaneous, separate or sequential use in viral infection therapy, such as of HIV.

More generally, the invention relates to the compounds of formula (A) being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

The term "pharmaceutically acceptable salts" as used herein means the therapeutically active non-toxic salt forms which the compounds of formulae herein are able to form. Therefore, the compounds of this invention optionally comprise salts of the compounds herein, especially pharmaceutically acceptable non-toxic salts containing, for example, $Na^+$, $Li^+$, $K^+$, $NH_4^+$, $Ca^{2+}$ and $Mg^{2+}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds of formulae herein as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived from a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and stereochemical forms (including atropisomers), which the compounds of formulae herein may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of formulae herein may have at least one chiral center and may exhibit atropisomerism) of the basic molecular structure, as well as the stereochemically pure or enriched compounds. More particularly, stereogenic centers may have either the R- or S-configuration, and multiple bonds may have either cis- or trans-configuration.

When the 4-substituent ($R^1$) is not symmetrical about the plane of the bond at the 4-position, atropisomerism may also arise. This is because rotation about the bond at the 4-position of the tricyclic core of the compounds of the present invention may be restricted. Such compounds may therefore exist as atropisomers. For example:

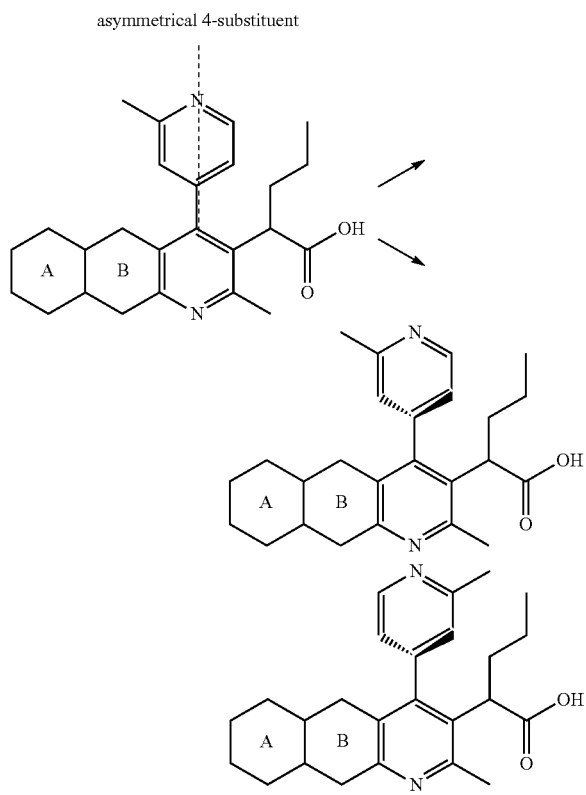

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms "cis" and "trans" are used herein in accordance with Chemical Abstracts nomenclature and include reference to the position of the substituents on a ring moiety. The absolute stereochemical configuration of the compounds of formula (I) may easily be determined by those skilled in the art while using well-known methods such as, for example, X-ray diffraction.

The compounds of the invention may be formulated with conventional carriers and excipients, which will be selected in accordance with standard practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable from coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw", 2 d ed. (Hanser Verlag, Vienna, 1981) and "Encyclopaedia of Surfactants, (Chemical Publishing Co., New York, 1981)

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone, it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulphatesulphate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Another embodiment of this invention relates to various precursor or "prodrug" forms of the compounds of the present invention. It may be desirable to formulate the compounds of the present invention in the form of a chemical species which itself is not significantly biologically-active, but which when delivered to the animal will undergo a chemical reaction catalyzed by the normal function of the body of the animal, inter alia, enzymes present in the stomach or in blood serum, said chemical reaction having the effect of releasing a compound as defined herein. The term "prodrug" thus relates to these species which are converted in vivo into the active pharmaceutical ingredient.

The prodrugs of the present invention can have any form suitable to the formulator, for example, esters are non-limiting common prodrug forms. In the present case, however, the pro-drug may necessarily exist in a form wherein a covalent bond is cleaved by the action of an enzyme present at the target locus. For example, a C—C covalent bond may be selectively cleaved by one or more enzymes at said target locus and, therefore, a prodrug in a form other than an easily hydrolysable precursor, inter alia an ester, an amide, and the like, may be used. The counterpart of the active pharmaceutical ingredient in the prodrug can have different structures such as an amino acid or peptide structure, alkyl chains, sugar moieties and others as known in the art.

For the purpose of the present invention the term "therapeutically suitable prodrug" is defined herein as "a compound modified in such a way as to be transformed in vivo to the therapeutically active form, whether by way of a single or by multiple biological transformations, when in contact with the tissues of the animal, mammal or human to which the prodrug has been administered, and without undue toxicity, irritation, or allergic response, and achieving the intended therapeutic outcome".

More specifically the term "prodrug", as used herein, relates to an inactive or significantly less active derivative of a compound such as represented by the structural formula (I), which undergoes spontaneous or enzymatic transformation within the body in order to release the pharmacologically active form of the compound. For a comprehensive review, reference is made to Rautio J. et al. ("Prodrugs: design and clinical applications" Nature Reviews Drug Discovery, 2008, doi: 10.1038/nrd2468).

The compounds with a structure according to the following formulae, among other compounds of the invention,

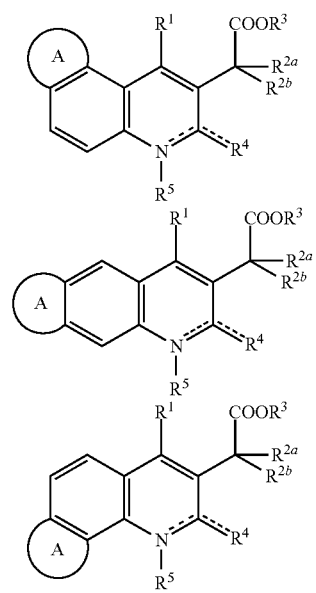

can be prepared according to the following general procedures depicted hereunder:

Scheme 1:

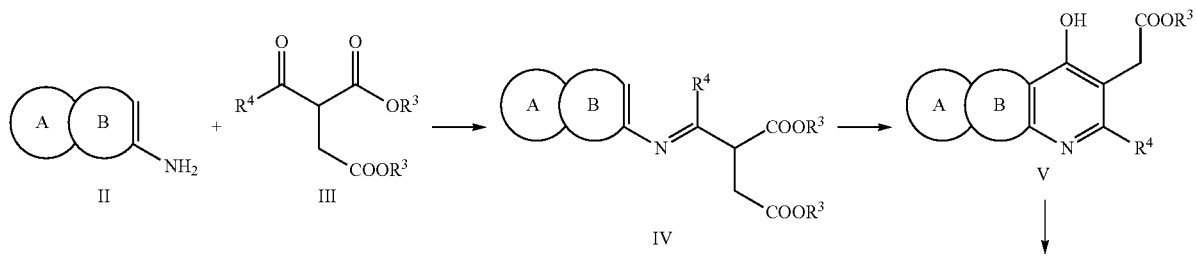

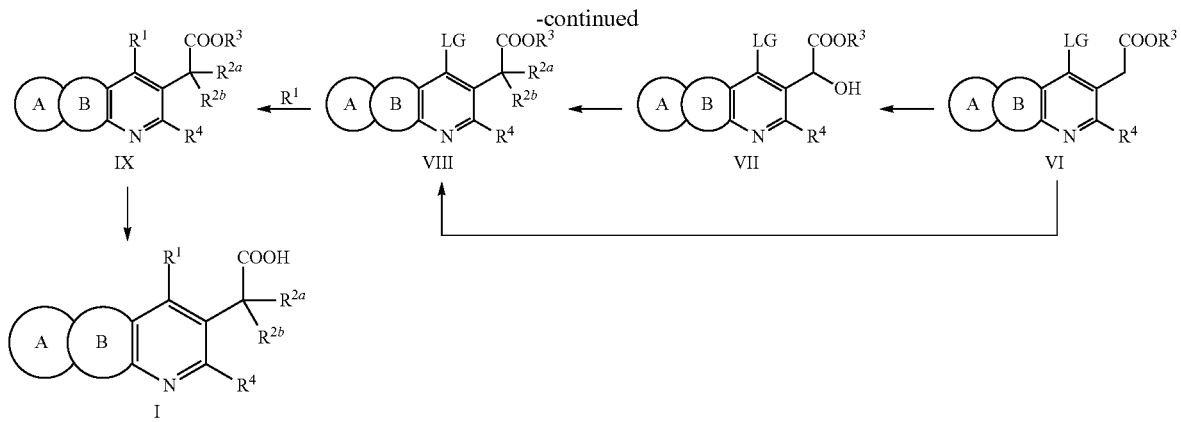

Scheme 1: all $R^1$, $R^{2a}$, $R^{2b}$, $R^3$, $R^4$, A, B and LG are as described for the compounds of the present invention and its embodiments and formulae.

Condensation of derivatives of general formula II (commercially available or synthesized by procedures known to the skilled in the art) with intermediates of formula III under dehydration conditions provides intermediates of formula IV which can be converted into intermediates of formula V by thermic cyclisation. The intermediates V are then converted to intermediates of formula VI wherein LG is a leaving group by procedures known to the skilled in the art or as set forth in the examples below. Alkylation of intermediates of formula VI, by procedures known to the skilled in the art or as set forth in the examples below, provides compounds of formula VIII. Coupling of intermediates VIII with a suitable $R^1$ precursor by procedures known to the skilled in the art (amination, Suzuki coupling, Negishi coupling, Stille coupling and the like) provides compounds of formula IX which can be converted in the desired compounds of formula I using standard hydrolysis conditions. Additionally, intermediates of general formula VI can be reacted with the Davis' reagent in basic conditions (e.g., KHMDS, n-BuLi, and the like) in a polar aprotic solvent (e.g., tetrahydrofuran, tert-butylmethylether and the like) to provide derivatives of formula VII. Intermediates of general formula VIII may be obtained by reacting intermediates of formula VII with suitable $R^{2a}X$ and or $R^{2b}X$, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, dichloromethane, DMF and the like) at a temperature raising from −78° C. to 80° C. (most preferably −78° C.). Alternatively, compounds of general formula VIII may also be obtained in acidic conditions by reacting intermediates of formula VII with an alkene (e.g., ethylene, prolylene, isoprene and the like) or an alkene precursor (e.g., isopropyl acetate, tert-butyl acetate, and the like). In another embodiment, the hydroxyl function of intermediates VII may also be converted into a leaving group selected from sulfonates (e.g., mesylate, tosylate and the like) or from halogen atom (e.g., chlorine, bromine, iodine) following procedures known to the skilled in the art or as set forth in the examples below. This leaving group can then undergo a nucleophilic substitution using suitable precursors of $R^{2a}$ and or $R^{2b}$ following reactions which are known to the skilled in the art to provide the desired intermediates of formula VIII. Alternatively, the hydroxyl function of intermediates VII may also be converted into a keto (C=O) function following standard oxidation reactions which are known to the skilled in the art. This keto function can then be subjected to reductive amination conditions using suitable precursors of $R^{2a}$ and or $R^{2b}$ to provide the desired intermediates of formula VIII.

Scheme 2:

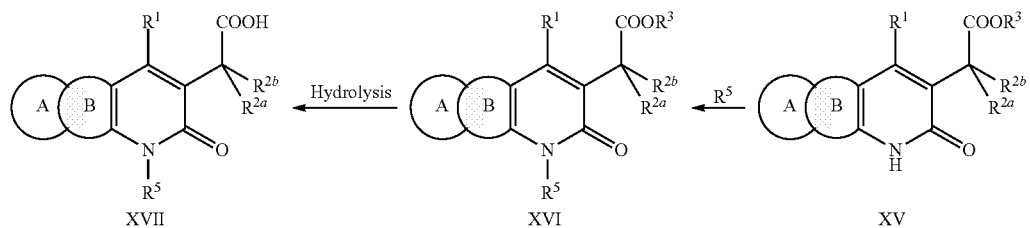

Scheme 2: all $R^1$, $R^{2a}$, $R^{2b}$, $R^3$, $R^5$, LG, A and B are as described for the compounds of the present invention and its embodiments and formulae.

Compounds of general formula XVII are prepared according to the reference WO2007/131350. Condensation of ketone of formula X (commercially available or synthesized by procedures known to the skilled in the art) with dimethylcarbonate in the presence of a base (e.g., NaH, $K_2CO_3$ and the like) in an apolar aprotic solvent (e.g., benzene, toluene, xylene and the like) at a temperature raising from 80 to 140° C. furnished intermediates of formula XI, which are reacted with derivatives of formula II (commercially available or synthesized by procedures known to the skilled in the art) to provide intermediates XII. Alkylation of intermediates of formula XII with intermediate XIII (commercially available or synthesized by procedures known to the skilled in the art) by procedures known to the skilled in the art, provides compounds of formula XIV. Compounds of formula XV are obtained by thermic cyclisation from intermediates XIV in acidic conditions (e.g., $H_2SO_4$, HCl and the like). Alkylation of intermediates of formula XV with suitable $R^5X$, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, dichloromethane, DMF and the like) provides compounds of formula XVI, which can be converted in compounds of formula XVII using standard hydrolysis conditions.

The compounds with a structure according to formula:

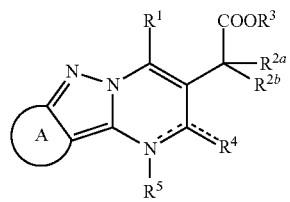

can be prepared according to the following general procedures depicted hereunder:

Scheme 3:

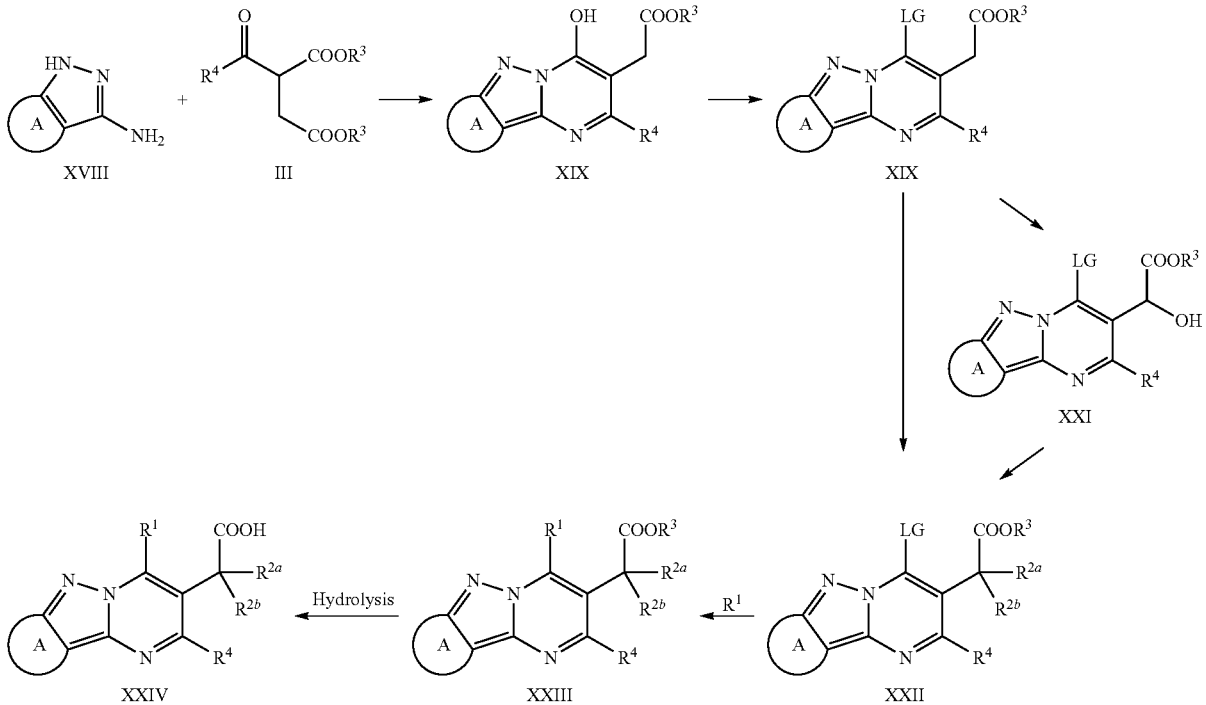

Scheme 3: all $R^1$, $R^{2a}$, $R^{2b}$, $R^3$, $R^4$, A and LG are as described for the compounds of the present invention and its embodiments and formulae.

Condensation of derivatives of general formula XVIII (commercially available or synthesized by procedures known to the skilled in the art) with intermediates of formula III (commercially available or synthesized by procedures known to the skilled in the art) in the presence of an apolar aprotic solvent (e.g., benzene, toluene, xylene and the like) or a polar protic solvent (e.g., ethanol, or acetic acid) at a temperature raising from 80 to 140° C., provides the desired intermediates of formula XIX. Intermediates XIX can then be converted in intermediates of formula XX by procedures known to the skilled in the art or as set forth in the examples below and wherein LG is a leaving group. Intermediates XXI to XXIII can be synthesized using the same protocols as shown for intermediates VII, VIII and IX in scheme 1. Compounds of formula XXIII can be converted in the desired compounds of formula XXIV using standard hydrolysis conditions.

The compounds with a structure according to formula:

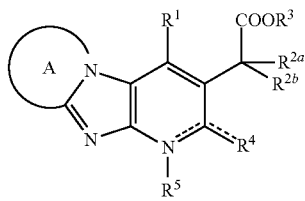

can be prepared according to the following general procedures depicted hereunder:

Condensation of intermediates of general formula XXV (commercially available or synthesized by procedures known to the skilled in the art or as set forth in the examples below) with intermediates of formula XXVI, in the presence of trimethylsilyl chloride provides intermediates of formula XXVII. Alkylation of intermediates of formula XXVII by procedures known to the skilled in the art or as set forth in the examples below, provides compounds of formula XXVIII which can be converted in the desired compounds of formula XXX using standard hydrolysis conditions. Alternatively, intermediates of general formula XXVIII can also be obtained from the condensation of intermediates of formula XXV with intermediates of formula XXIX (commercially available or synthesized by procedures known to the skilled in the art or as set forth in the examples below).

Scheme 4:

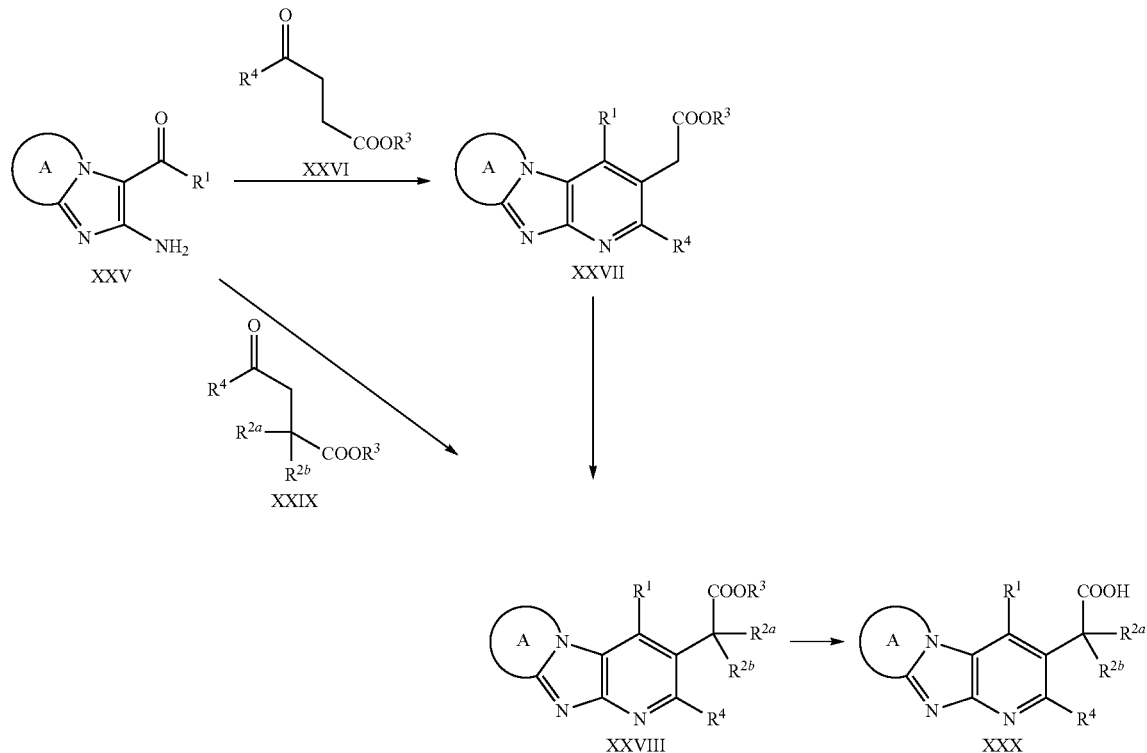

Scheme 4: all $R^1$, $R^{2a}$, $R^{2b}$, $R^3$, $R^4$ and A are as described for the compounds of the present invention and its embodiments and formulae.

Scheme 5:

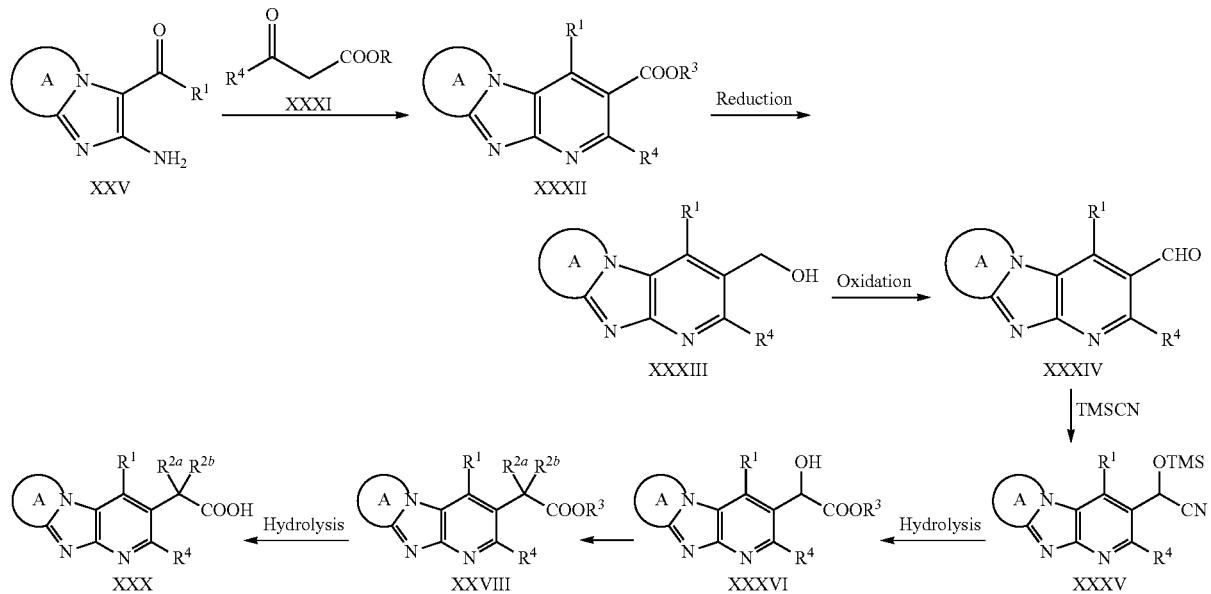

Scheme 5: all $R^1$, $R^2$, $R^3$, $R^4$ and A are as described for the compounds of the present invention and its embodiments and formulae.

Condensation of intermediates of general formula XXV (commercially available or synthesized by procedures known to the skilled in the art) with intermediates of formula XXXI in the presence of trimethylsilyl chloride provides intermediates of formula XXXII. Intermediates of formula XXXII can then be converted into intermediates of formula XXXIII by reduction of the ester functionality using standard reducing agents (LiAlH$_4$ and most preferably DIBAL) in polar aprotic solvents (e.g., THF, dichloromethane and the like) at a temperature ranging from −78° C. to 0° C. (most preferably −78° C.). Intermediates of formula XXXIII can then be oxidized in intermediates of formula XXXIV by procedures known to the skilled in the art. Addition of trimethylsilylcyanide on intermediates XXXIV in the presence of zinc iodide provides intermediates of formula XXXV, which are immediately hydrolyzed under acidic conditions to provide intermediates of formula XXXVI. Intermediates of general formula XXVIII may be obtained by reacting intermediates of formula XXXVI with suitable $R^{2a}$X and or $R^{2b}$X, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, dichloromethane, DMF and the like) at a temperature raising from −78° C. to 80° C. (most preferably −78° C.). Alternatively, compounds of general formula XXVIII may also be obtained in acidic conditions by reacting an alkene (e.g., ethylene, prolylene, isoprene and the like) or an alkene precursor (e.g., isopropyl acetate, tert-butyl acetate, and the like). In another embodiment, the hydroxyl function of intermediates XXXVI may also be converted into a leaving group selected from sulfonates (e.g., mesylate, tosylate and the like) or from halogen atom (e.g., chlorine, bromine, iodine) following procedures known to the skilled in the art or as set forth in the examples below. This leaving group can then undergo a nucleophilic substitution using suitable precursors of $R^{2a}$ and or $R^{2b}$ following reactions which are known to the skilled in the art to provide the desired intermediates of formula XXVIII. Alternatively, the hydroxyl function of intermediates XXXVI may also be converted into a keto (C=O) function following standard oxidation reactions which are known to the skilled in the art. This keto function can then be subjected to reductive amination conditions using suitable precursors of $R^{2a}$ and or $R^{2b}$ to provide the desired intermediates of formula XXVIII. Compounds of formula XXVIII can finaly be converted in the desired compounds of formula XXX using standard hydrolysis conditions.

Alternatively, compounds of general formula XXX can also be prepared as outlined in Scheme 6 below.

Scheme 6:
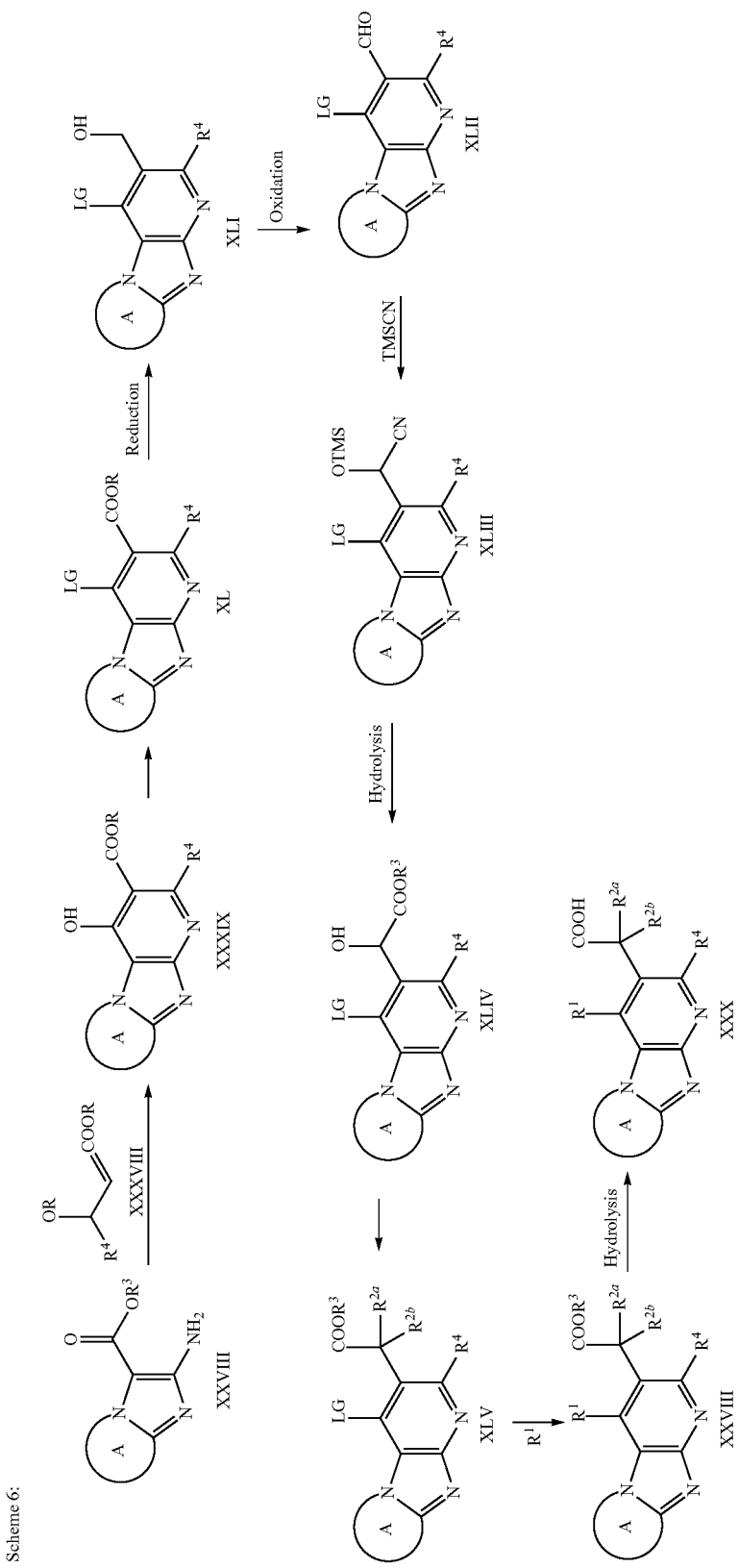
Scheme 6: all $R^1$, $R^{2a}$, $R^{2b}$, $R^3$, $R^4$, LG and A are as described for the compounds of the present invention and its embodiments and formulae.

Intermediates of formula XXXVII (commercially available or synthesized by procedures known to the skilled in the art) can be reacted with intermediates of formula XXXVIII (commercially available or synthesized by procedures known to the skilled in the art), wherein R is an alkyl group such as methyl or ethyl, in an apolar aprotic solvent (e.g., benzene, toluene, xylene and the like) at a temperature raising from 80 to 140° C. to provide enamine intermediates which are converted into intermediates of general formula XXXIX in the presence of a strong base (e.g., sodium hydride, sodium methoxide, sodium ethoxide) in a polar protic solvent (e.g., methanol, ethanol, tert-butanol and the like). Intermediates XXXIX are then converted in intermediates of formula XL by procedures known to the skilled in the art, and wherein LG is a leaving group only selected from halogen. It is known for the skilled in the art that when LG is a chlorine atom, this atom can be exchange for a more reactive halogen atom (bromine or iodine) using substitution reactions which are known to the skilled in the art. Intermediates of formula XL can then be converted into intermediates of formula XLI by reduction of the ester functionality using standard reducing agents (Li-AlH$_4$ and most preferably DIBAL) in polar aprotic solvents (e.g., THF, dichloromethane and the like) at a temperature ranging from −78° C. to 0° C. (most preferably −78° C.). Intermediates of formula XLI can then be oxidized in intermediates of formula XLII by procedures known to the skilled in the art. Addition of trimethylsilylcyanide on intermediates dichloromethane, DMF and the like) at a temperature raising from −78° C. to 80° C. (most preferably −78° C.). Alternatively, compounds of general formula XLV may also be obtained in acidic conditions by reacting an alkene (e.g., ethylene, prolypene, isoprene and the like) or an alkene precursor (e.g., isopropyl acetate, tert-butyl acetate, and the like). In another embodiment, the hydroxyl function of intermediates XLIV may also be converted into a leaving group selected from sulfonates (e.g., mesylate, tosylate and the like) or from halogen atom (e.g., chlorine, bromine, iodine) following procedures known to the skilled in the art or as set forth in the examples below. This leaving group can then undergo a nucleophilic substitution using suitable precursors of R$^{2a}$ and or R$^{2b}$ following reactions which are known to the skilled in the art to provide the desired intermediates of formula XLV. Alternatively, the hydroxyl function of intermediates XLIV may also be converted into a keto (C═O) function following standard oxidation reactions which are known to the skilled in the art. This keto function can then be subjected to reductive amination conditions using suitable precursors of R$^{2a}$ and or R$^{2b}$ to provide the desired intermediates of formula XLV. Coupling of intermediates XLV with a suitable R$^1$ precursor by procedures known to the skilled in the art (amination, Suzuki coupling, Negishi coupling, Stille coupling and the like) provides compounds of formula XXVIII, which can be converted in the desired compounds of formula XXX using standard hydrolysis conditions.

Scheme 7:

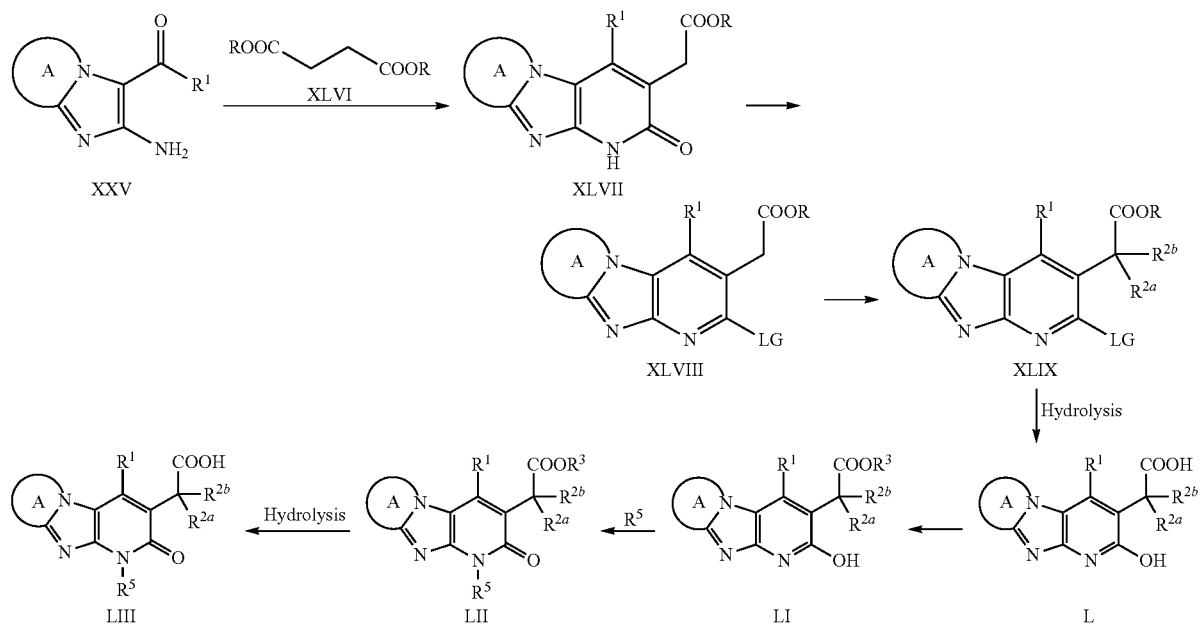

Scheme 7: all R$^1$, R$^{2a}$, R$^{2b}$, R$^3$, R$^5$, LG and A are as described for the compounds of the present invention and its embodiments and formulae.

XLII in the presence of zinc iodide provides intermediates of formula XLIII, which are immediately hydrolyzed under acidic conditions to provide intermediates of formula XLIV. Intermediates of general formula XLV may be obtained by reacting intermediates of formula XLIV with suitable R$^{2a}$X and or R$^{2b}$X, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, Intermediates of formula XXV (commercially available or synthesized by procedures known to the skilled in the art) can be reacted with intermediates of formula XLVI (commercially available or synthesized by procedures known to the skilled in the art) wherein R is an ester protecting group (e.g., methyl, ethyl and the like) in a polar protic solvent (e.g., methanol, ethanol, tert-butanol and the like) in the presence of a strong base (e.g., sodium hydride, potassium tert-butoxide, sodium ethoxide) at a temperature raising from 80 to 140° C.

to provide intermediates of general formula XLVII. Intermediates XLVII can then be converted in intermediates of formula XLVIII by procedures known to the skilled in the art, wherein LG is a leaving group only selected from halogen.

Intermediates of general formula XLIX may be obtained by reacting intermediates of formula XLVIII with suitable $R^{2a}X$ and or $R^{2b}X$, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, dichloromethane, DMF and the like) at a temperature raising from −78° C. to 80° C. (most preferably −78° C.). Intermediates of formula XLIX can then be converted in the desired compounds of formula L using standard hydrolysis conditions. Compounds of general formula LI can be obtained by standard esterification conditions. Compounds of general formula LII may be obtained by reacting intermediates of formula LI with suitable $R^5X$, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, dichloromethane, DMF and the like) at a temperature raising from −78° C. to 80° C. (most preferably −78° C.).

Compounds of formula LII can be converted in the desired compounds of formula LIII using standard hydrolysis conditions.

The compounds with a structure according to formula:

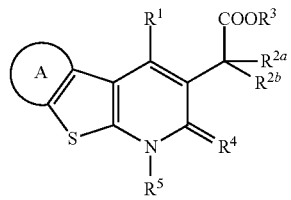

can be prepared according to the following general procedures depicted hereunder:

Scheme 8:
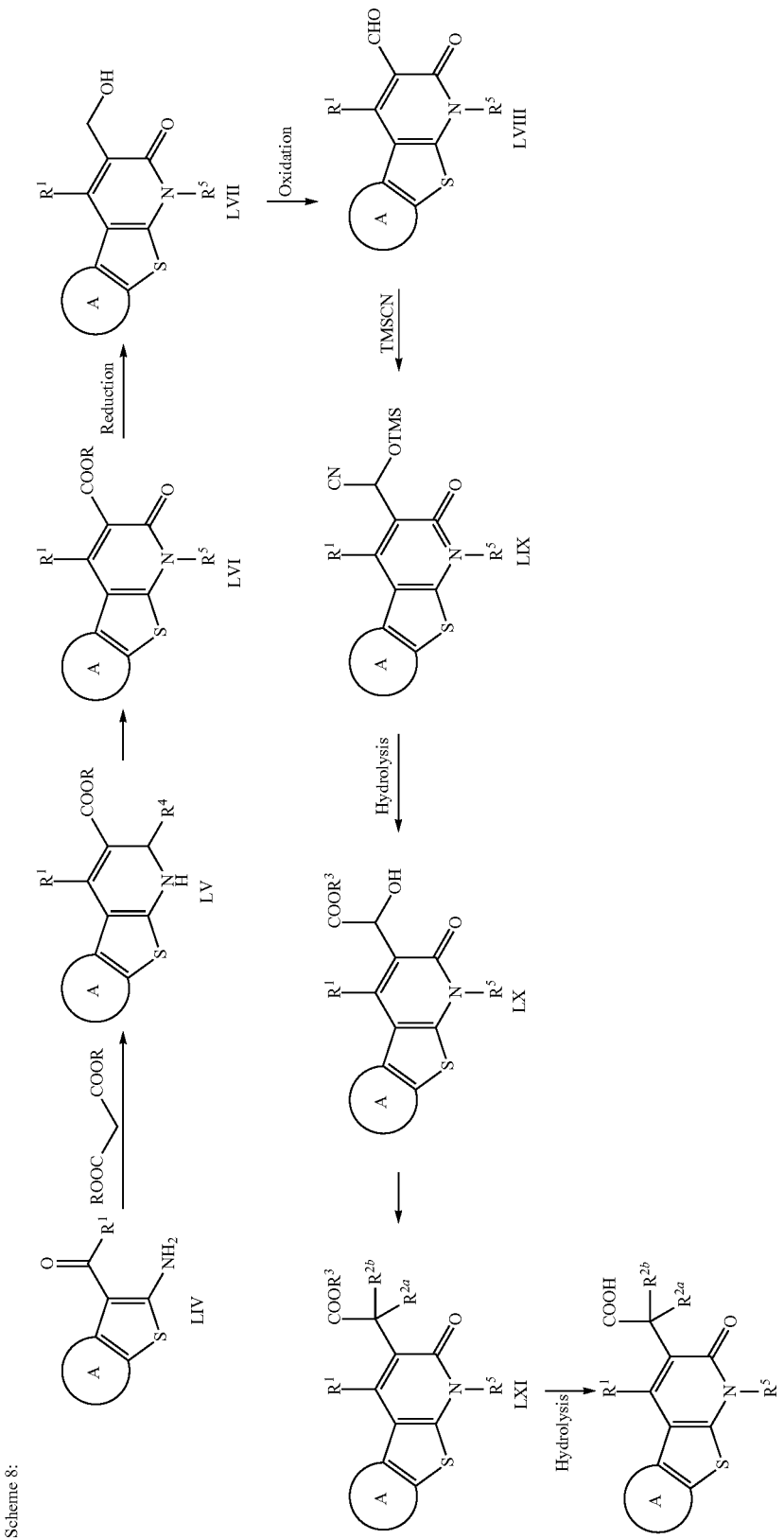
Scheme 8: all $R^1$, $R^{2a}$, $R^{2b}$, $R^3$, $R^5$, LG and A are as described for the compounds of the present invention and its embodiments and formulae.

Derivatives of formula LIV (commercially available or synthesized by procedures known to the skilled in the art) can be reacted with a dialkylmalonate, wherein R is an ester protecting group (e.g., methyl, ethyl and the like) in the presence of a strong base (e.g., piperidine, sodium hydride, sodium methoxide, sodium ethoxide) in a polar protic solvent (e.g., methanol, ethanol, tert-butanol and the like) at a temperature raising from 80 to 120° C. to provide intermediates of general formula LV. Intermediates of general formula LVI may be obtained by reacting intermediates of formula LV with suitable $R^5X$, wherein X is a leaving group such as a halogen atom (e.g., Cl, Br, I) or a sulfonate (e.g., mesylate, tosylate, triflate) in the presence of a strong base (e.g., NaH, LiHMDS, DBU and the like) in a polar aprotic solvent (e.g., THF, dichloromethane, DMF and the like) at a temperature raising from −78° C. to 80° C. (most preferably −78° C.). Intermediates LVII to LXI are synthesized using the same protocols as shown for intermediates XLI to XLV in scheme 6. Compounds of formula LXII can be converted in the desired compounds of formula LXI using standard hydrolysis conditions.

The compounds according to the invention can be synthesized in accordance with scheme 9. As an example, the compounds with a structure according to the following formulae can be prepared by using the general procedures depicted hereunder:

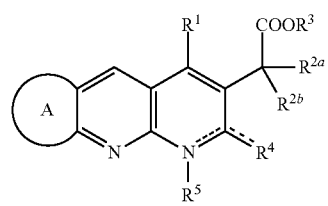

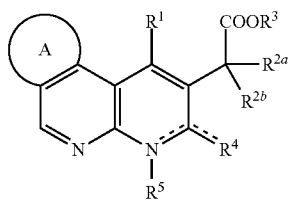

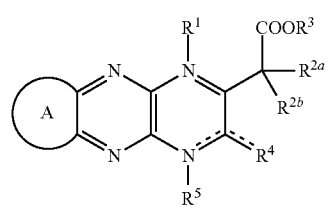

-continued

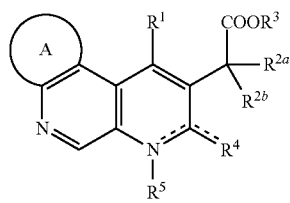

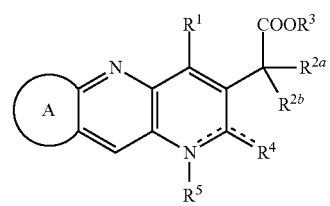

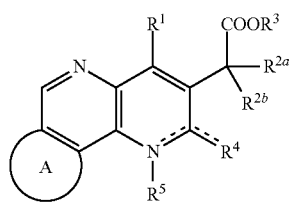

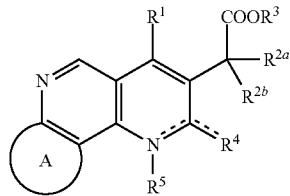

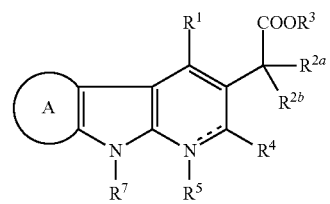

Scheme 9:

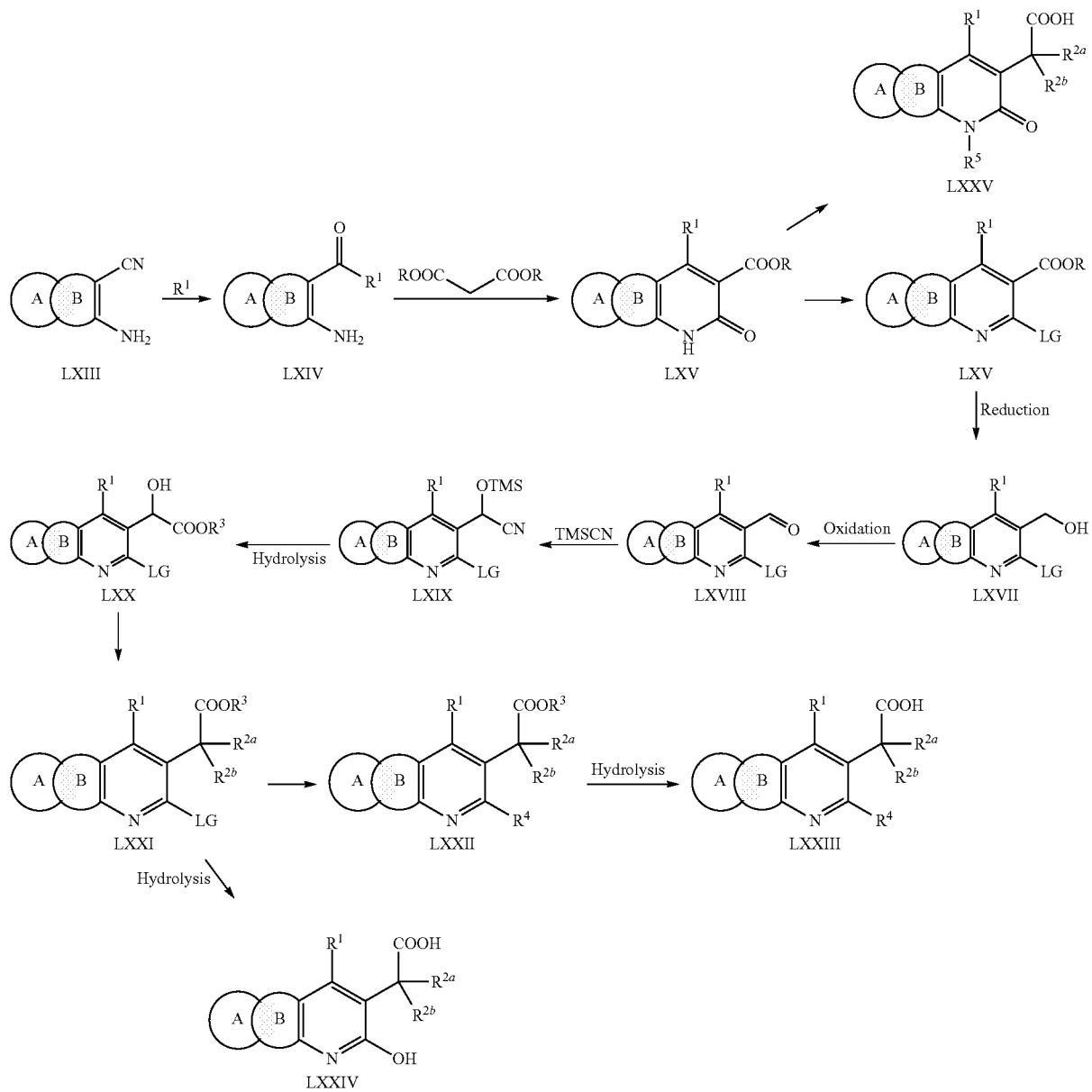

Scheme 9: all $R^1$, $R^{2a}$, $R^{2b}$, $R^3$, $R^4$, $R^5$, LG, A and B are as described for the compounds of the present invention and its embodiments and formulae.

Intermediates of formula LXIII (commercially available or synthesized by procedures known to the skilled in the art) can be reacted in a polar aprotic solvent (e.g., THF, $CH_2Cl_2$, dioxane) at a temperature raising from 20° C. to 120° C., with a Grignard's reagent general formula $R^1$—MgX (wherein X is selected from Cl, Br or I) to yield intermediates of formula LXIV. Intermediate of formula LXIV can be reacted with a dialkylmalonate, wherein R is an ester protecting group (e.g., methyl, ethyl and the like) in the presence of a strong base (e.g., piperidine, sodium hydride, sodium methoxide, sodium ethoxide) in a polar protic solvent (e.g., alcohol) at a temperature raising from 80 to 120° C. to provide intermediates of general formula LXV. Intermediates LXV are then converted in intermediates of formula LXVI by procedures known to the skilled in the art, and wherein LG is a leaving group only selected from halogen. It is known for the skilled in the art that when LG is a chlorine atom, this atom can be exchange for a more reactive halogen atom (bromine or iodine) using substitution reactions which are known to the skilled in the art. Intermediates LXVII to LXXXI are synthesized using the same protocols as shown for intermediates XLI to XLV in scheme 6. Coupling of intermediates LXXI with a suitable $R^4$ precursor by procedures known to the skilled in the art (amination, Suzuki coupling, Negishi coupling, Stille coupling and the like) provides compounds of formula LXXII, which can be converted in the desired compounds of formula LXXIII using standard hydrolysis conditions. Compounds of formula LXXI can be converted in the desired compounds of formula LXXIV using standard hydrolysis conditions. Compound of formula LXXV can be synthesized from intermediate LXV using the same protocols as shown for intermediates LVI to LXII in scheme 8.

The compounds with a structure according to formula:

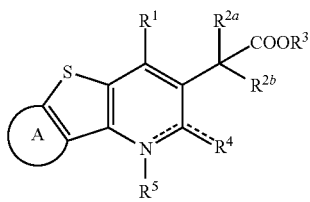

can be prepared according to the following general procedures depicted hereunder:

The compounds with a structure according to formula:

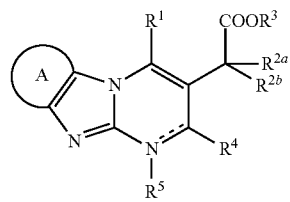

can be prepared according to the following general procedures depicted hereunder. The compounds XCII to XCVI can Scheme 10:

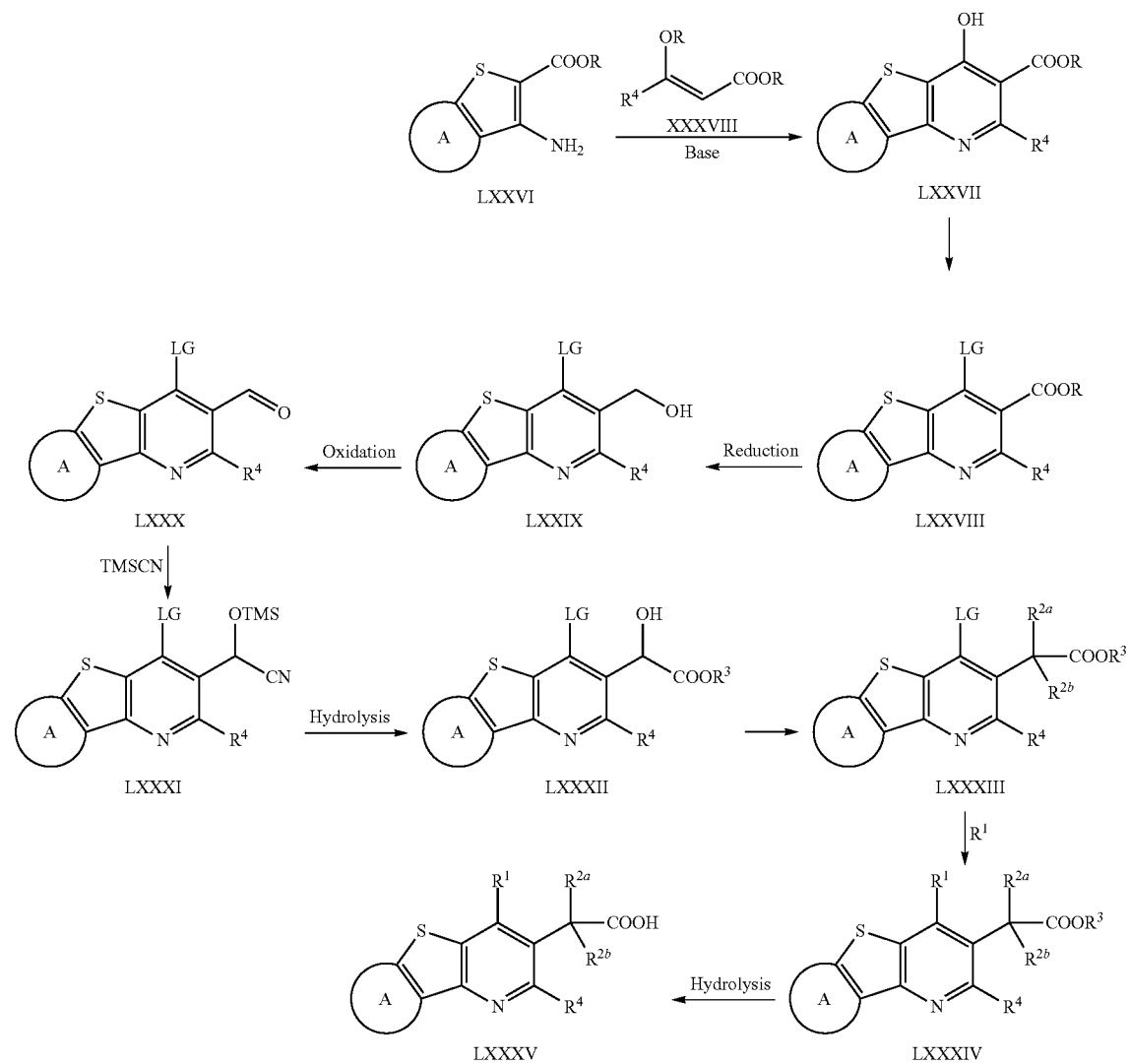

Scheme 10: all $R^1$, $R^{2a}$, $R^{2b}$, $R^4$, A and LG are as described for the compounds of the present invention and its embodiments and formulae.

In a first instance, derivatives of formula LXXVI can be prepared according to the procedure published in US2009/0075970. The compounds LXXVII to LXXXV can be synthesized using the synthetic procedures described in WO2009/062288.

be synthesized using the same protocols as shown in scheme 4. Intermediates of general formula III and XCI are commercially available or intermediates XCI synthesized by procedures known to the skilled in the art (see reference US2006/099379).

Scheme 11:
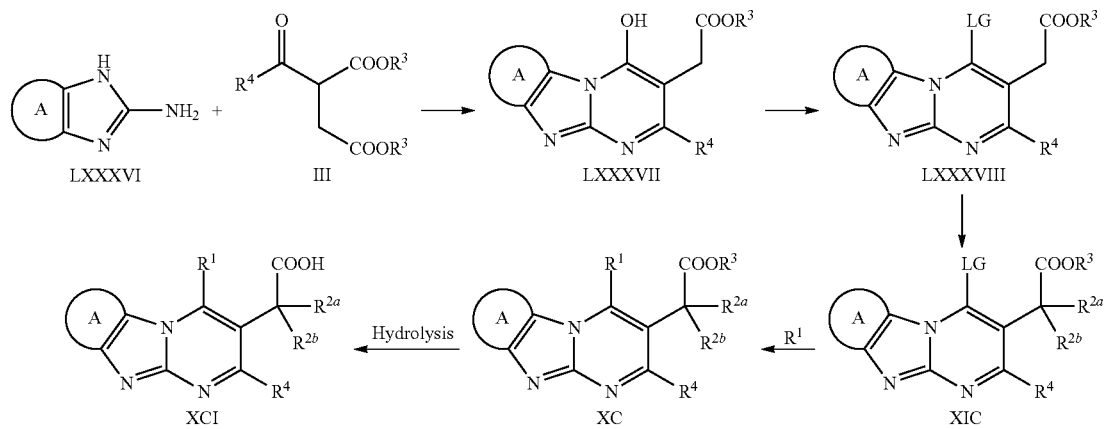
Scheme 11: all $R^1$, $R^{2a}$, $R^{2b}$, $R^3$, $R^4$, $R^6$ and LG are as described for the compounds of the present invention and its embodiments and formulae.
The compounds with a structure according to formula:
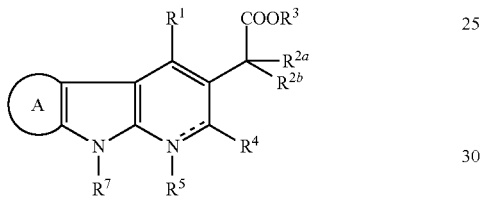
can be prepared according to the following general procedure depicted hereunder:

Scheme 12:
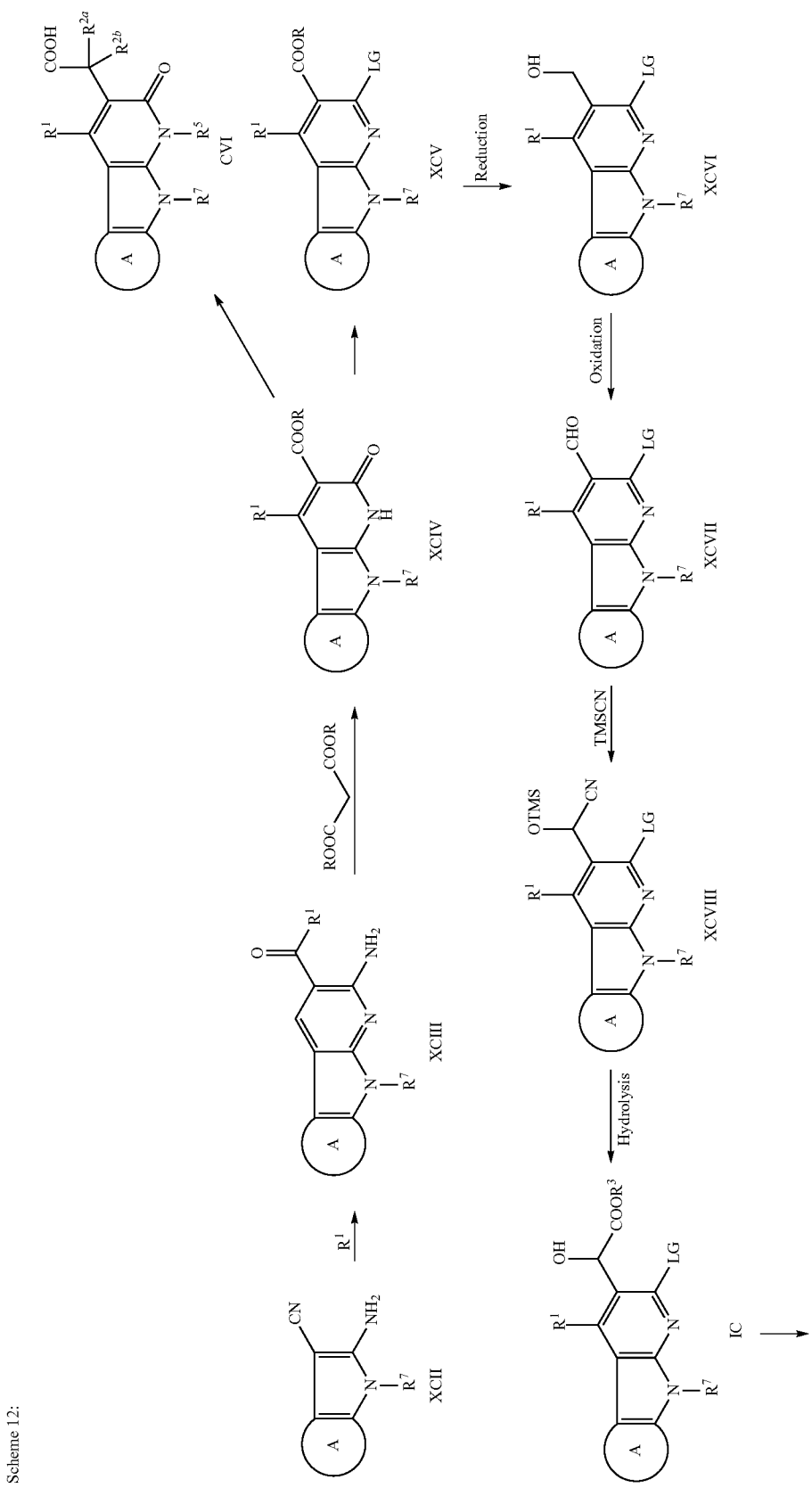

-continued
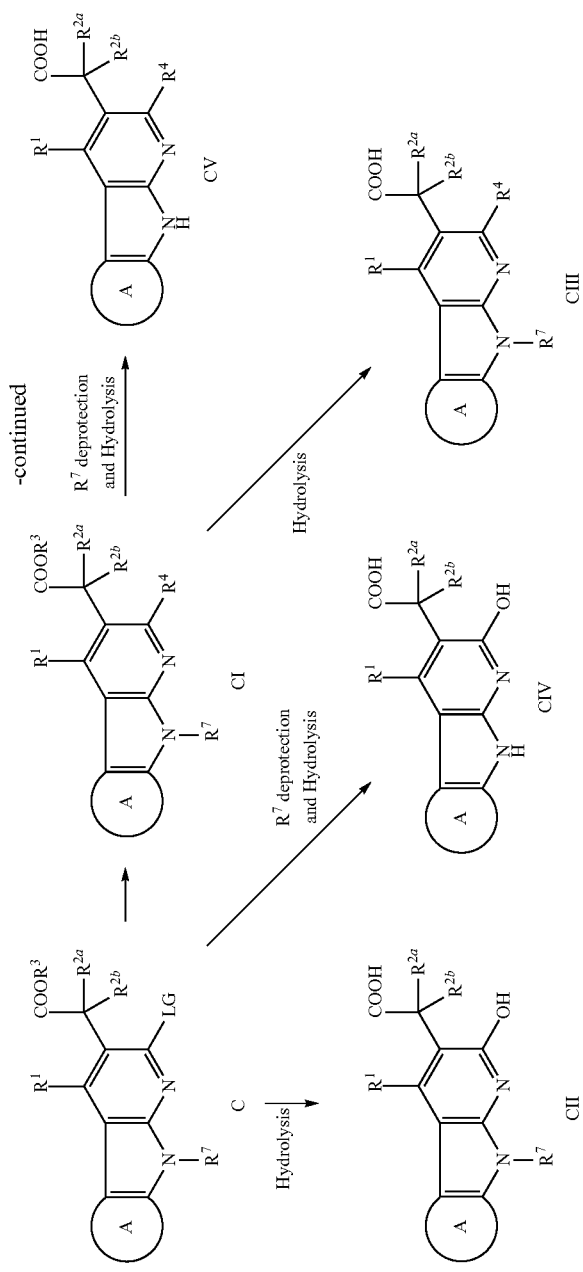
Scheme 12: all $R^1$, $R^{2a}$, $R^{2b}$, $R^3$, $R^4$, $R^5$, $R^7$, LG and A are as described for the compounds of the present invention and its embodiments and formulae.

Intermediates of formula XCII (commercially available or synthesized by procedures known to the skilled in the art) can be reacted in a polar aprotic solvent (e.g., THF, $CH_2Cl_2$, dioxane) at a temperature raising from 20° C. to 120° C., with a Grignard's reagent general formula $R^1$—MgX (wherein X is selected from Cl, Br or I) to yield intermediates of formula XCIII. Intermediate of formula XCIII can be reacted with a dialkylmalonate, wherein R is an ester protecting group (e.g., methyl, ethyl and the like) in the presence of a strong base (e.g., piperidine, sodium hydride, sodium methoxide, sodium ethoxide) in a polar protic solvent (e.g., alcohol) at a temperature raising from 80 to 120° C. to provide intermediates of general formula XCIV. Intermediates XCIV are then converted in intermediates of formula XCV by procedures known to the skilled in the art, and wherein LG is a leaving group only selected from halogen. It is known for the skilled in the art that when LG is a chlorine atom, this atom can be exchange for a more reactive halogen atom (bromine or iodine) using substitution reactions which are known to the skilled in the art. Intermediates XCVII to C can be synthesized using the same protocols as shown for intermediates XLI to XLV in scheme 6. Coupling of intermediates C with a suitable $R^4$ precursor by procedures known to the skilled in the art (amination, Suzuki coupling, Negishi coupling, Stille coupling and the like) provides compounds of formula C1, which can be converted in the desired compounds of formula CIII and CV using standard hydrolysis and deprotection conditions. Compounds of formula C can be converted in the desired compounds of formula CII using standard hydrolysis conditions. Compounds of formula C can be converted in the desired compounds of formula CIV using standard deprotection conditions followed by standard hydrolysis conditions. Compound of formula CV1 can be synthesized from intermediate XCIV using the same protocols as shown for intermediates LVI to LXII in scheme 8.

The compounds with a structure according to formula:

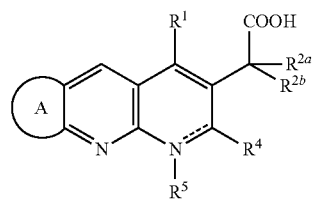

can be prepared according to the following general procedure depicted hereunder:

Scheme 13:

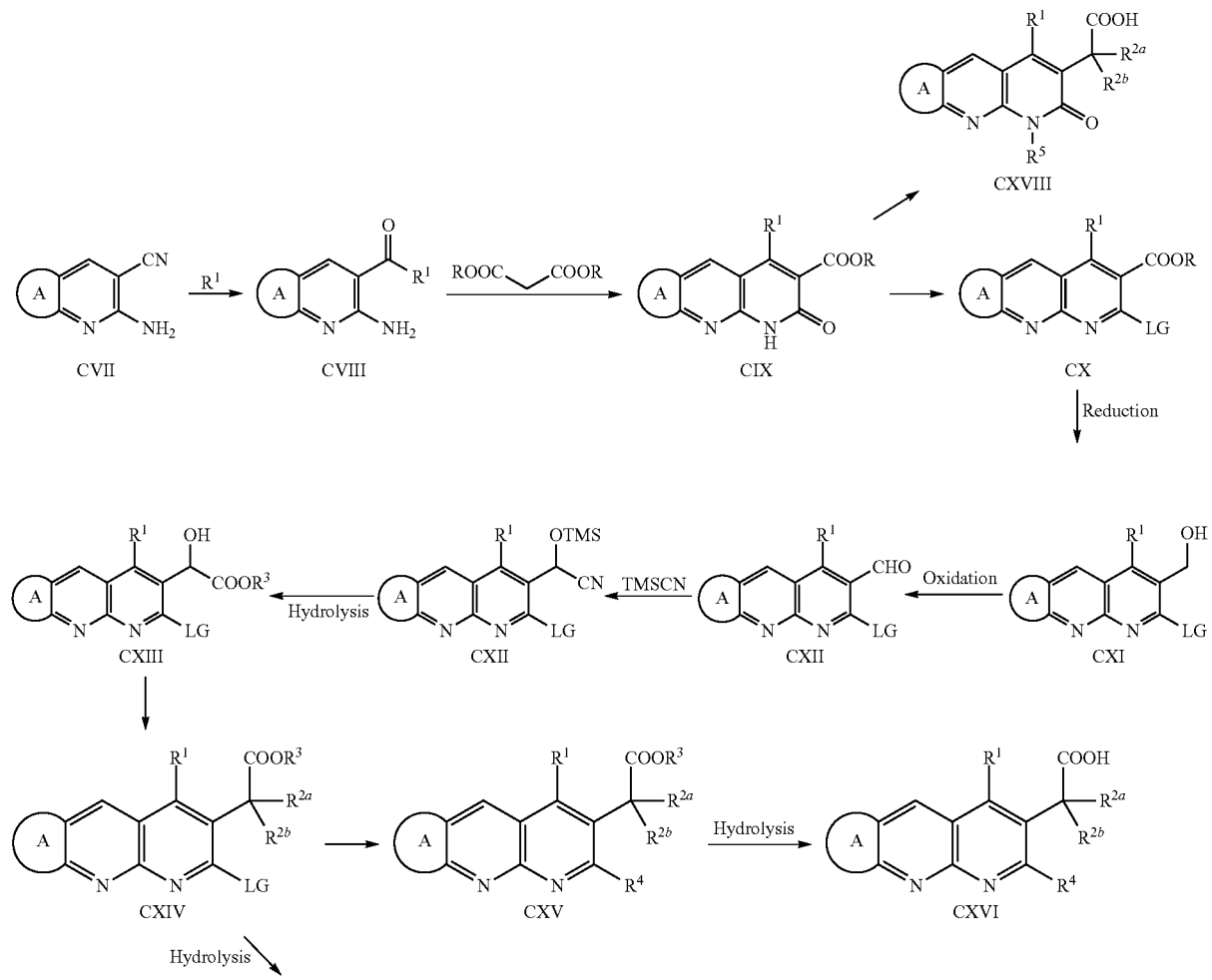

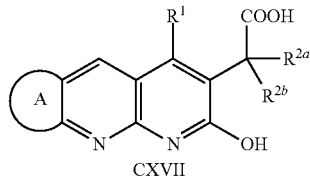
CXVII

Scheme 13: all $R^1$, $R^{2a}$, $R^{2b}$, $R^3$, $R^4$, $R^5$, LG and A are as described for the compounds of the present invention and its embodiments and formulae.

Intermediates of formula CVII (commercially available or synthesized by procedures known to the skilled in the art) can be reacted in a polar aprotic solvent (e.g., THF, $CH_2Cl_2$, dioxane) at a temperature raising from 20° C. to 120° C., with a Grignard's reagent general formula $R^1$—MgX (wherein X is selected from Cl, Br or I) to yield intermediates of formula CVIII. Intermediate of formula CVIII can be reacted with a dialkylmalonate, wherein R is an ester protecting group (e.g., methyl, ethyl and the like) in the presence of a strong base (e.g., piperidine, sodium hydride, sodium methoxide, sodium ethoxide) in a polar protic solvent (e.g., alcohol) at a temperature raising from 80 to 120° C. to provide intermediates of general formula CIX. Intermediates CIX are then converted in intermediates of formula CX by procedures known to the skilled in the art, and wherein LG is a leaving group only selected from halogen. It is known for the skilled in the art that when LG is a chlorine atom, this atom can be exchange for a more reactive halogen atom (bromine or iodine) using substitution reactions which are known to the skilled in the art. Intermediates CXI to CXIV are synthesized using the same protocols as shown for intermediates XLI to XLV in scheme 6. Coupling of intermediates CXIV with a suitable $R^4$ precursor by procedures known to the skilled in the art (amination, Suzuki coupling, Negishi coupling, Stille coupling and the like) provides compounds of formula CXV, which can be converted in the desired compounds of formula CXVI using standard hydrolysis conditions. Compounds of formula CXIV can be converted in the desired compounds of formula CXVII using standard hydrolysis conditions. Compound of formula CXVIII can be synthesized from intermediate CIX using the same protocols as shown for intermediates LVI to LXII in scheme 8.

The compounds with a structure according to formula:

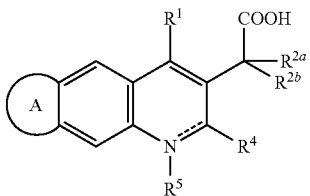

can be prepared according to the following general procedure depicted hereunder:

Scheme 14

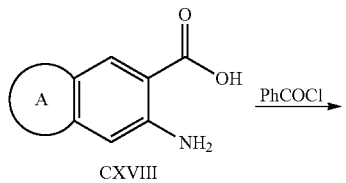
CXVIII

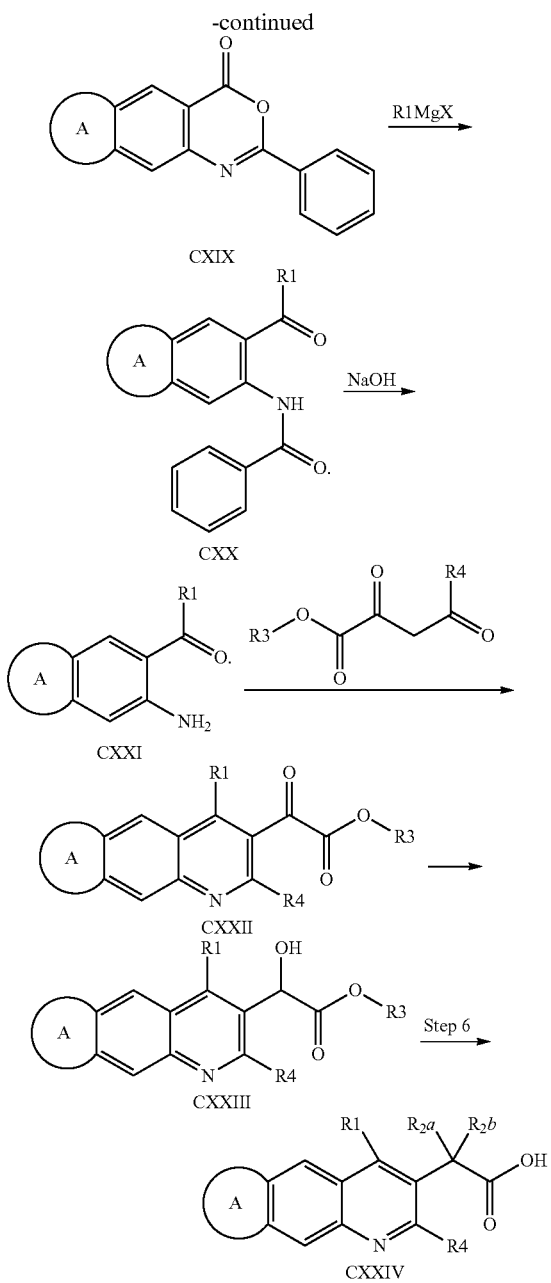

Intermediates of formula CXVIII (commercially available or synthesized by procedures known to the skilled in the art) can be reacted in a polar aprotic solvent (e.g., THF, $CH_2Cl_2$, dioxane) at a temperature raising from 20° C. to 70° C., with benzoyl chloride to yield intermediates of formula CXIX. Intermediates of formula CXIX can be reacted in a polar aprotic solvent (e.g., THF, CH$_2$Cl$_2$, dioxane) at a temperature raising from −70° C. to 30° C., with a Grignard's reagent general formula R$^1$—MgX (wherein X is selected from Cl, Br or I) to yield intermediates of formula CXX. Intermediate of formula CXX can be hydrolysed in the presence of a base e.g. sodium hydroxide in a polar solvent e.g. ethanol, which is miscible with water at a temperature from 20° C. to 130° C. to yield intermediates of formula CXXI. Intermediates of formula CXXI are then reacted with a 2,4-diketoalkanoate wherein R$^3$ is an ester protecting group (e.g., methyl, ethyl and the like) in the presence of an anhydrous acid e.g. TMSCl, HCl optionally generated by reaction of the solvent e.g. ethanol with an acylating reagent e.g. acetyl chloride, phosphorus trichloride at a temperature of 20° C. to 130° C. to provide intermediates of general formula CXXII. Intermediates CXXII are then converted to intermediates of formula CXXIII by a reduction method such as metal hydride reduction e.g. sodium borohydride or hydrogenation, optionally in the presence of a catalyst. Compounds of formula CXXIV can be synthesized from intermediate CXIII using the same protocols as shown for intermediates LX to LXII in scheme 8.

EXAMPLES

The following examples are provided for the purpose of illustrating the present invention and by no means should be interpreted to limit the scope of the present invention. Part A describes the preparation of the compounds (intermediates and final compounds) whereas Part B describes the antiviral activity of the compounds of the invention.

TABLE 1

Structures of example compounds of the invention and their respective codes.

| CPD CODE | STRUCTURE |
|---|---|
| Cpd001 | 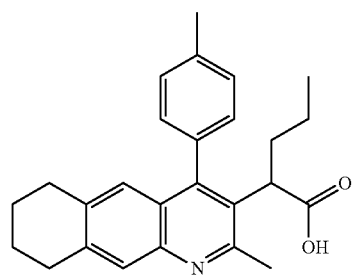 [SMILES: CCCC(C(=O)O)c1c(C)nc2cc3c(cc2c1-c1ccc(C)cc1)CCCC3] |
| Cpd002 | 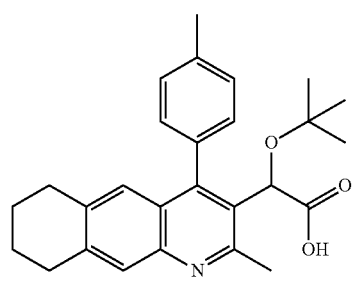 [SMILES: Cc1ccc(-c2c(C(OC(C)(C)C)C(=O)O)c(C)nc3cc4c(cc23)CCCC4)cc1] |

TABLE 1-continued

Structures of example compounds of the invention and their respective codes.

| CPD CODE | STRUCTURE |
|---|---|
| Cpd003 | 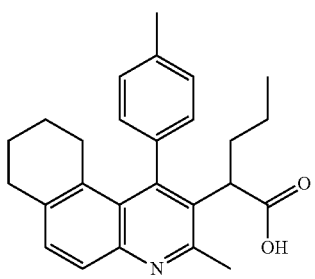 [SMILES: CCCC(C(=O)O)c1c(C)nc2ccc3c(c2c1-c1ccc(C)cc1)CCCC3] |
| Cpd004 | 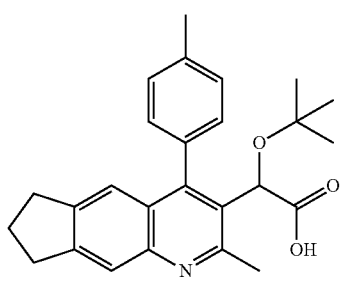 [SMILES: Cc1ccc(-c2c(C(OC(C)(C)C)C(=O)O)c(C)nc3cc4c(cc23)CCC4)cc1] |
| Cpd005 | 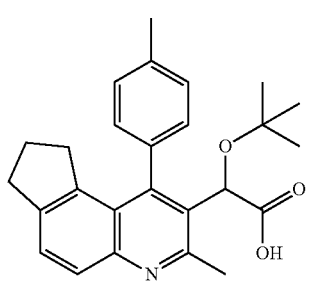 [SMILES: Cc1ccc(-c2c(C(OC(C)(C)C)C(=O)O)c(C)nc3ccc4c(c23)CCC4)cc1] |
| Cpd006 | 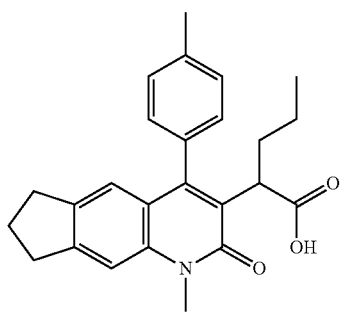 [SMILES: CCCC(C(=O)O)c1c(-c2ccc(C)cc2)c2cc3c(cc2n(C)c1=O)CCC3] |
| Cpd007 | 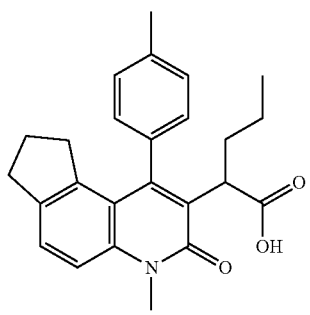 [SMILES: CCCC(C(=O)O)c1c(-c2ccc(C)cc2)c2c3c(ccc2n(C)c1=O)CCC3] |

TABLE 1-continued
Structures of example compounds of the invention and their respective codes.
CPD CODE   STRUCTURE
Cpd008
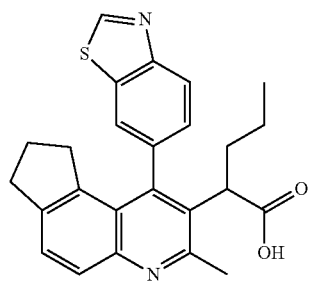 [SMILES: CCCC(C(=O)O)c1c(C)nc2ccc3c(c2c1-c1ccc2ncsc2c1)CCC3]
Cpd009
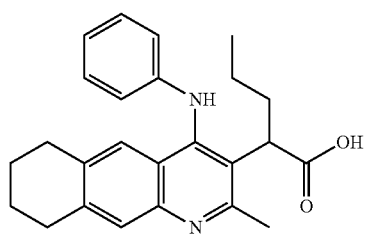 [SMILES: CCCC(C(=O)O)c1c(C)nc2cc3c(cc2c1Nc1ccccc1)CCCC3]
Cpd010
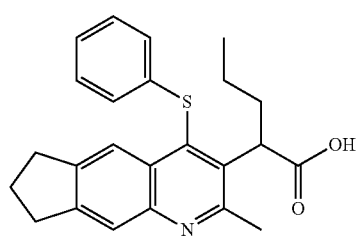 [SMILES: CCCC(C(=O)O)c1c(C)nc2cc3c(cc2c1Sc1ccccc1)CCC3]
Cpd011
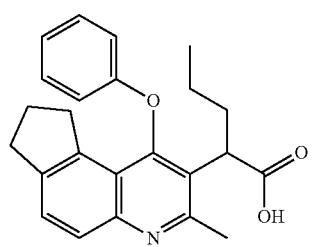 [SMILES: CCCC(C(=O)O)c1c(C)nc2ccc3c(c2c1Oc1ccccc1)CCC3]
Cpd012
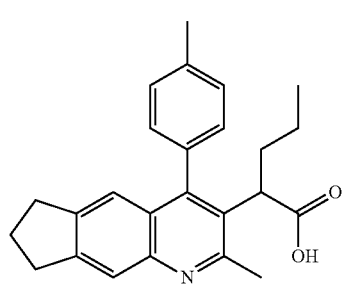
TABLE 1-continued
Structures of example compounds of the invention and their respective codes.
CPD CODE   STRUCTURE
Cpd013
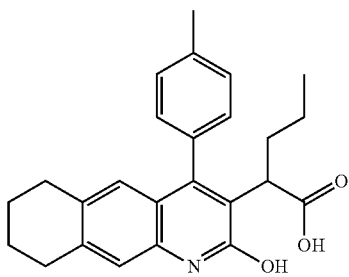
Cpd014
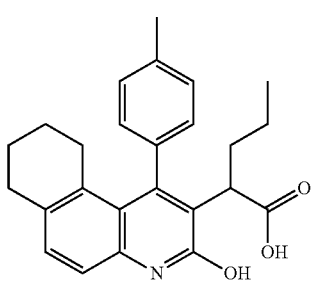 [SMILES: CCCC(C(=O)O)c1c(O)nc2ccc3c(c2c1-c1ccc(C)cc1)CCCC3]
Cpd015
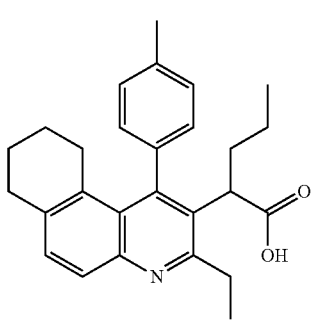 [SMILES: CCCC(C(=O)O)c1c(CC)nc2ccc3c(c2c1-c1ccc(C)cc1)CCCC3]
Cpd016
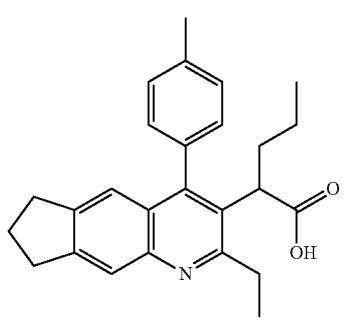 [SMILES: CCCC(C(=O)O)c1c(CC)nc2cc3c(cc2c1-c1ccc(C)cc1)CCC3]
Cpd017
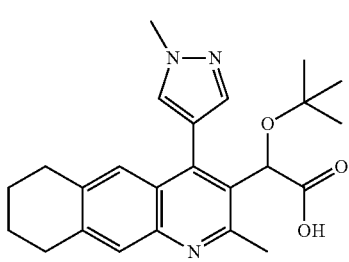 [SMILES: Cc1nc2cc3c(cc2c(-c2cnn(C)c2)c1C(OC(C)(C)C)C(=O)O)CCCC3]

TABLE 1-continued
Structures of example compounds of the invention and their respective codes.
CPD CODE  STRUCTURE
Cpd018
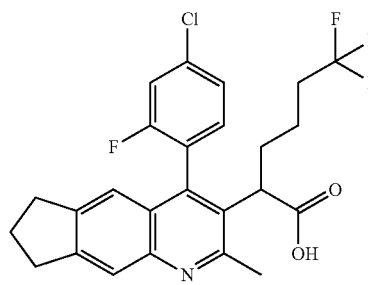
Cpd019
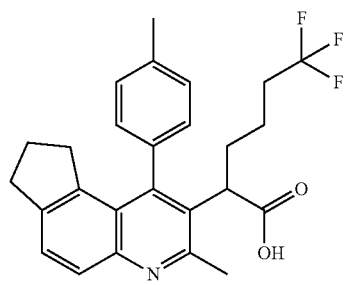 [SMILES: Cc1ccc(-c2c(C(CCCC(F)(F)F)C(=O)O)c(C)nc3ccc4c(c23)CCC4)cc1]
Cpd020
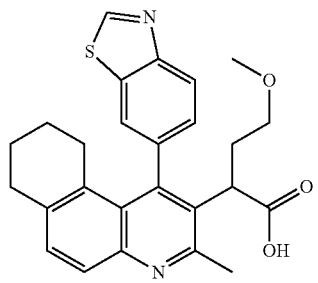 [SMILES: COCCC(C(=O)O)c1c(C)nc2ccc3c(c2c1-c1ccc2ncsc2c1)CCCC3]
Cpd021
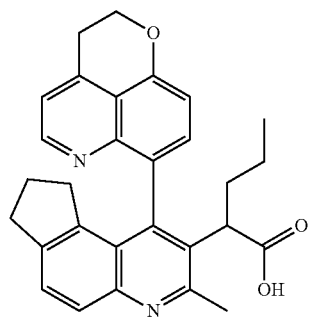 [SMILES: CCCC(C(=O)O)c1c(C)nc2ccc3c(c2c1-c1ccc2c4c(ccnc14)CCO2)CCC3]
Cpd022
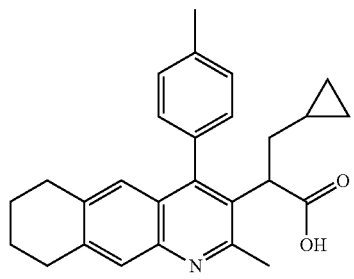 [SMILES: Cc1ccc(-c2c(C(CC3CC3)C(=O)O)c(C)nc3cc4c(cc23)CCCC4)cc1]
Cpd023
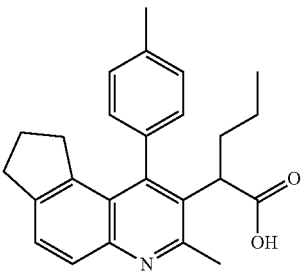 [SMILES: CCCC(C(=O)O)c1c(C)nc2ccc3c(c2c1-c1ccc(C)cc1)CCC3]
Cpd024
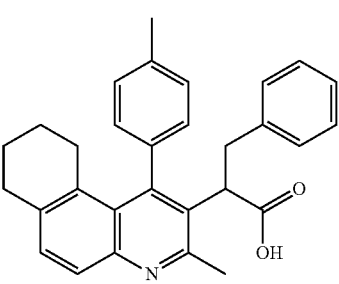 [SMILES: Cc1ccc(-c2c(C(Cc3ccccc3)C(=O)O)c(C)nc3ccc4c(c23)CCCC4)cc1]
Cpd025
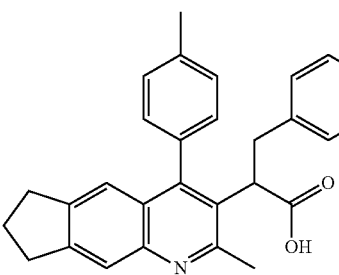
Cpd026
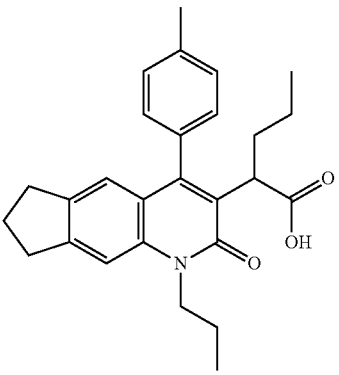 [SMILES: CCCC(C(=O)O)c1c(-c2ccc(C)cc2)c2cc3c(cc2n(CCC)c1=O)CCC3]

TABLE 1-continued
Structures of example compounds of the invention and their respective codes.
| CPD CODE | STRUCTURE |
|---|---|
| Cpd027 | 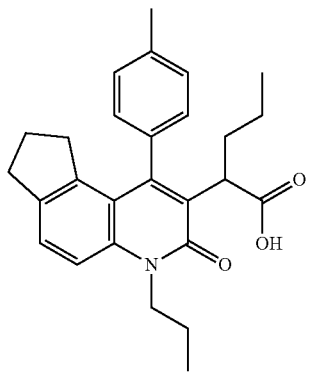 [SMILES: CCCC(C(=O)O)c1c(-c2ccc(C)cc2)c2c3c(ccc2n(CCC)c1=O)CCC3] |
| Cpd028 | 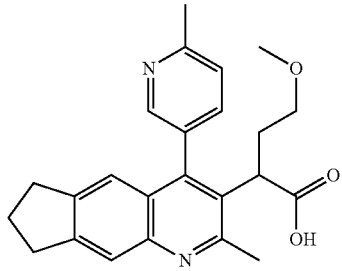 [SMILES: COCCC(C(=O)O)c1c(C)nc2cc3c(cc2c1-c1ccc(C)nc1)CCC3] |
| Cpd029 | 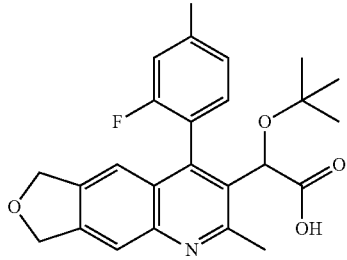 |
| Cpd030 | 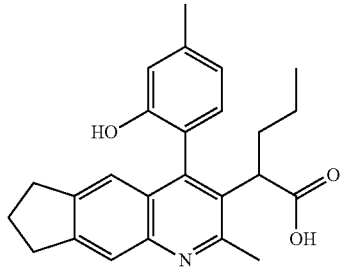 [SMILES: CCCC(C(=O)O)c1c(C)nc2cc3c(cc2c1-c1ccc(C)cc1O)CCC3] |
| Cpd031 | 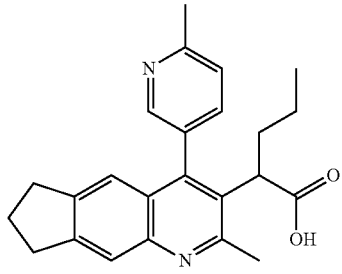 |
| Cpd032 | 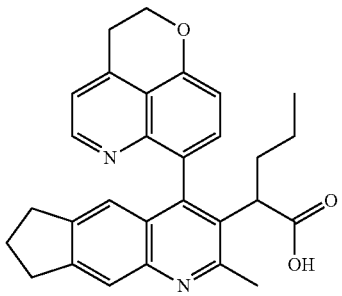 [SMILES: CCCC(C(=O)O)c1c(C)nc2cc3c(cc2c1-c1ccc2c4c(ccnc14)CCO2)CCC3] |
| Cpd033 | 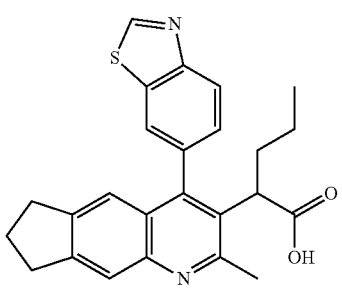 [SMILES: CCCC(C(=O)O)c1c(C)nc2cc3c(cc2c1-c1ccc2ncsc2c1)CCC3] |
| Cpd034 | 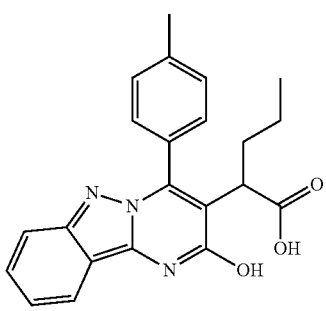 [SMILES: CCCC(C(=O)O)c1c(O)nc2c3ccccc3nn2c1-c1ccc(C)cc1] |
| Cpd035 | 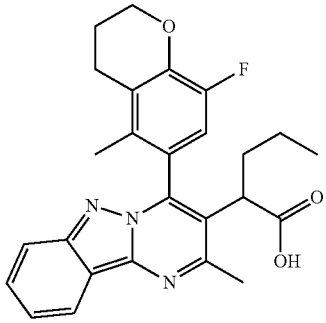 [SMILES: CCCC(C(=O)O)c1c(C)nc2c3ccccc3nn2c1-c1cc(F)c2c(c1C)CCCO2] |
| Cpd036 | 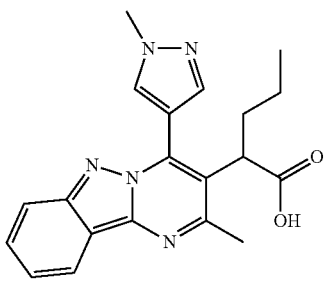 [SMILES: CCCC(C(=O)O)c1c(C)nc2c3ccccc3nn2c1-c1cnn(C)c1] |

TABLE 1-continued
Structures of example compounds of the invention and their respective codes.
| CPD CODE | STRUCTURE |
|---|---|
| Cpd037 | 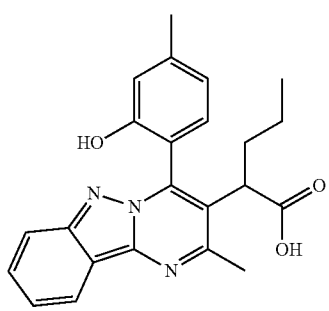 [SMILES: CCCC(C(=O)O)c1c(C)nc2c3ccccc3nn2c1-c1ccc(C)cc1O] |
| Cpd038 | 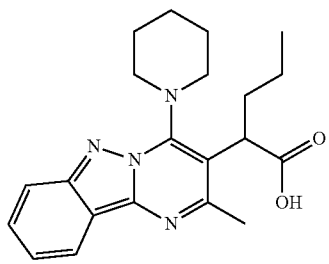 [SMILES: CCCC(C(=O)O)c1c(C)nc2c3ccccc3nn2c1N1CCCCC1] |
| Cpd039 | 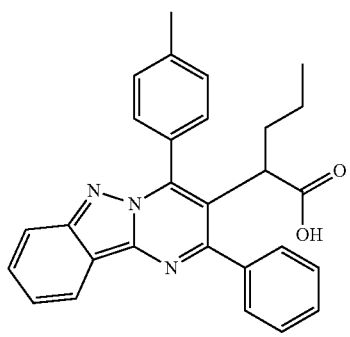 [SMILES: CCCC(C(=O)O)c1c(-c2ccccc2)nc2c3ccccc3nn2c1-c1ccc(C)cc1] |
| Cpd040 | 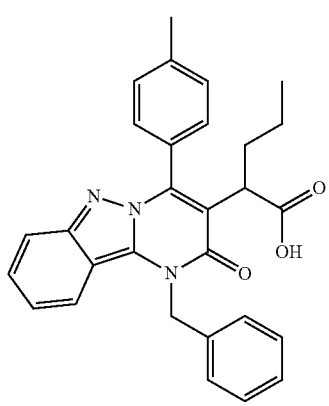 [SMILES: CCCC(C(=O)O)c1c(-c2ccc(C)cc2)n2nc3ccccc3c2n(Cc2ccccc2)c1=O] |
| Cpd041 | 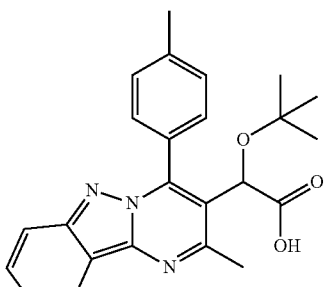 |
| Cpd042 | 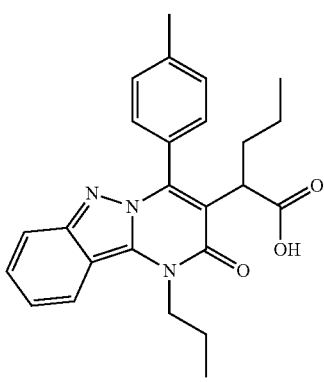 [SMILES: CCCC(C(=O)O)c1c(-c2ccc(C)cc2)n2nc3ccccc3c2n(CCC)c1=O] |
| Cpd043 | 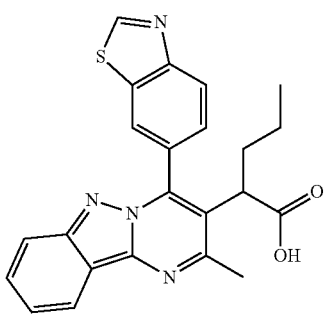 [SMILES: CCCC(C(=O)O)c1c(C)nc2c3ccccc3nn2c1-c1ccc2ncsc2c1] |
| Cpd044 | 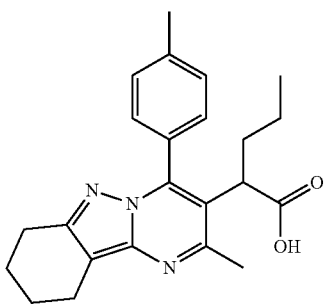 [SMILES: CCCC(C(=O)O)c1c(C)nc2c3c(nn2c1-c1ccc(C)cc1)CCCC3] |

TABLE 1-continued
Structures of example compounds of the invention and their respective codes.
| CPD CODE | STRUCTURE |
|---|---|
| Cpd045 | 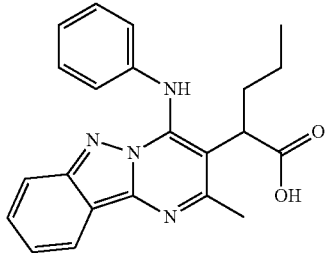 [SMILES: CCCC(C(=O)O)c1c(C)nc2c3ccccc3nn2c1Nc1ccccc1] |
| Cpd046 | 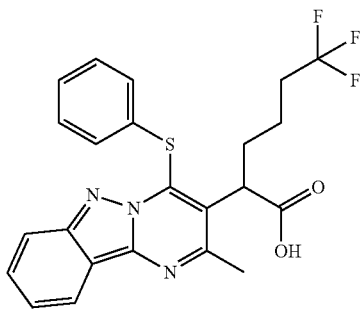 [SMILES: Cc1nc2c3ccccc3nn2c(Sc2ccccc2)c1C(CCCC(F)(F)F)C(=O)O] |
| Cpd047 | 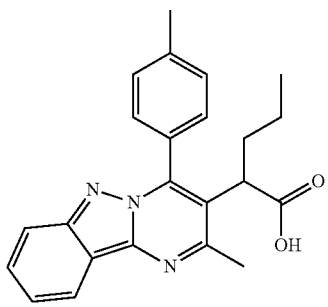 [SMILES: CCCC(C(=O)O)c1c(C)nc2c3ccccc3nn2c1-c1ccc(C)cc1] |
| Cpd048 | 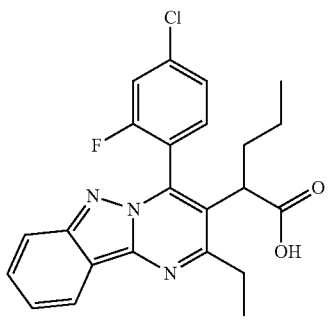 [SMILES: CCCC(C(=O)O)c1c(CC)nc2c3ccccc3nn2c1-c1ccc(Cl)cc1F] |
| Cpd049 | 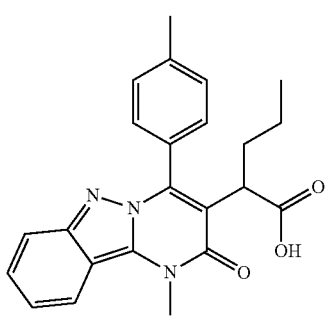 [SMILES: CCCC(C(=O)O)c1c(-c2ccc(C)cc2)n2nc3ccccc3c2n(C)c1=O] |
| Cpd050 | 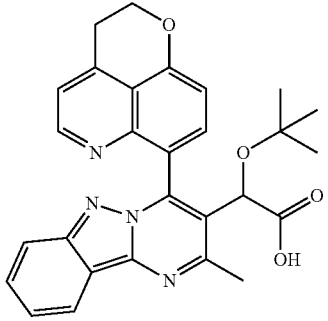 [SMILES: Cc1nc2c3ccccc3nn2c(-c2ccc3c4c(ccnc24)CCO3)c1C(OC(C)(C)C)C(=O)O] |
| Cpd051 | 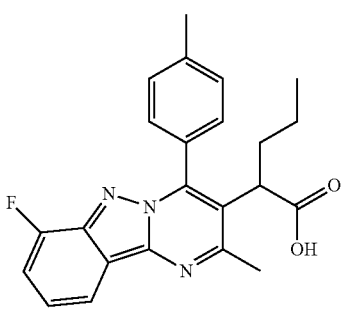 [SMILES: CCCC(C(=O)O)c1c(C)nc2c3cccc(F)c3nn2c1-c1ccc(C)cc1] |
| Cpd052 | 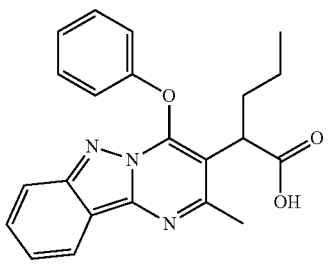 [SMILES: CCCC(C(=O)O)c1c(C)nc2c3ccccc3nn2c1Oc1ccccc1] |
| Cpd053 | 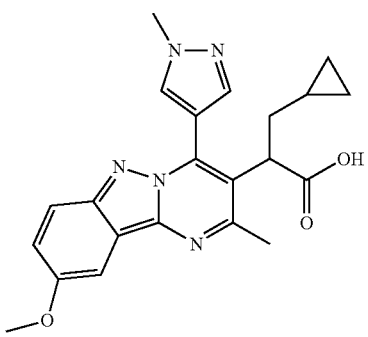 [SMILES: COc1ccc2nn3c(-c4cnn(C)c4)c(C(CC4CC4)C(=O)O)c(C)nc3c2c1] |
| Cpd054 | 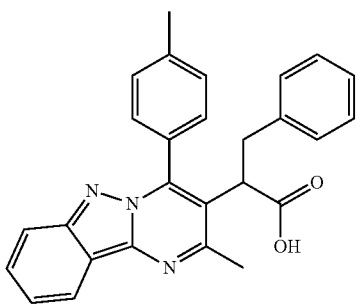 [SMILES: Cc1ccc(-c2c(C(Cc3ccccc3)C(=O)O)c(C)nc3c4ccccc4nn23)cc1] |

TABLE 1-continued
Structures of example compounds of the invention and their respective codes.
CPD CODE   STRUCTURE
Cpd055
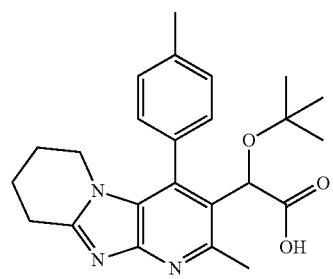 [SMILES: Cc1ccc(-c2c(C(OC(C)(C)C)C(=O)O)c(C)nc3nc4n(c23)CCCC4)cc1]
Cpd056
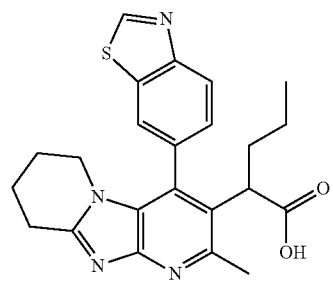 [SMILES: CCCC(C(=O)O)c1c(C)nc2nc3n(c2c1-c1ccc2ncsc2c1)CCCC3]
Cpd057
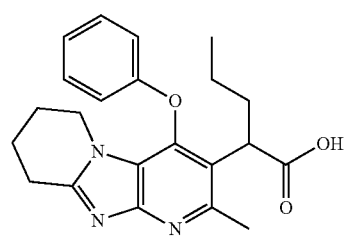 [SMILES: CCCC(C(=O)O)c1c(C)nc2nc3n(c2c1Oc1ccccc1)CCCC3]
Cpd058
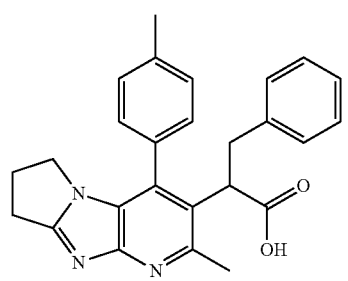 [SMILES: Cc1ccc(-c2c(C(Cc3ccccc3)C(=O)O)c(C)nc3nc4n(c23)CCC4)cc1]
Cpd059
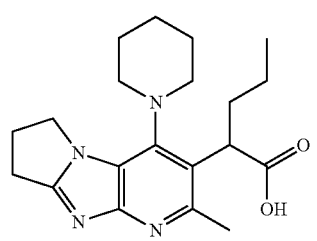 [SMILES: CCCC(C(=O)O)c1c(C)nc2nc3n(c2c1N1CCCCC1)CCC3]
TABLE 1-continued
Structures of example compounds of the invention and their respective codes.
CPD CODE   STRUCTURE
Cpd060
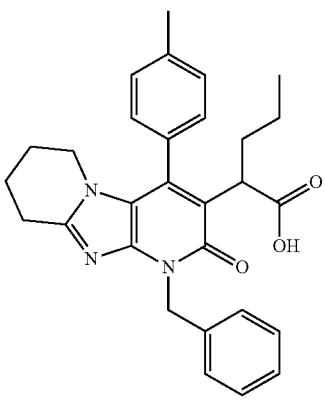 [SMILES: CCCC(C(=O)O)c1c(-c2ccc(C)cc2)c2c(nc3n2CCCC3)n(Cc2ccccc2)c1=O]
Cpd061
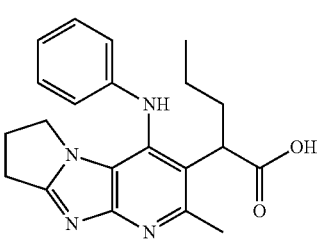 [SMILES: CCCC(C(=O)O)c1c(C)nc2nc3n(c2c1Nc1ccccc1)CCC3]
Cpd062
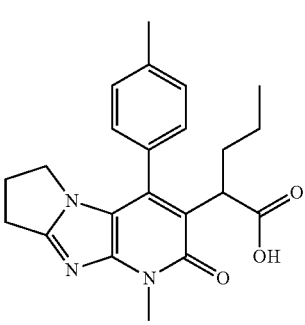 [SMILES: CCCC(C(=O)O)c1c(-c2ccc(C)cc2)c2c(nc3n2CCC3)n(C)c1=O]
Cpd063
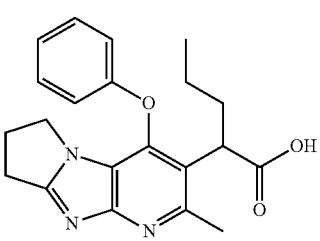

TABLE 1-continued
Structures of example compounds of the invention and their respective codes.
| CPD CODE | STRUCTURE |
|---|---|
| Cpd064 | 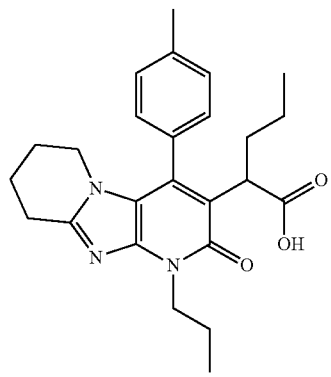 [SMILES: CCCC(C(=O)O)c1c(-c2ccc(C)cc2)c2c(nc3n2CCCC3)n(CCC)c1=O] |
| Cpd065 | 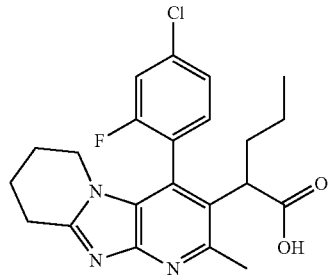 [SMILES: CCCC(C(=O)O)c1c(C)nc2nc3n(c2c1-c1ccc(Cl)cc1F)CCCC3] |
| Cpd066 | 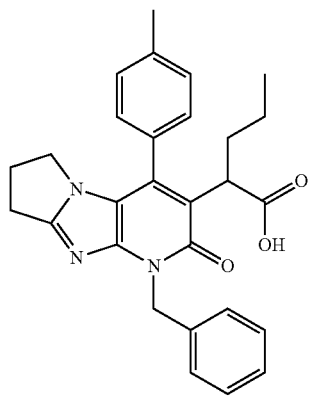 [SMILES: CCCC(C(=O)O)c1c(-c2ccc(C)cc2)c2c(nc3n2CCC3)n(Cc2ccccc2)c1=O] |
| Cpd067 | 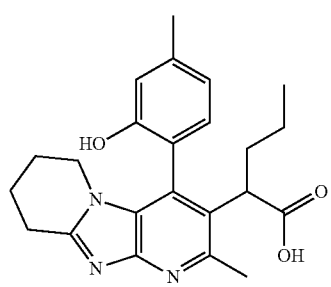 [SMILES: CCCC(C(=O)O)c1c(C)nc2nc3n(c2c1-c1ccc(C)cc1O)CCCC3] |
TABLE 1-continued
Structures of example compounds of the invention and their respective codes.
| CPD CODE | STRUCTURE |
|---|---|
| Cpd068 | 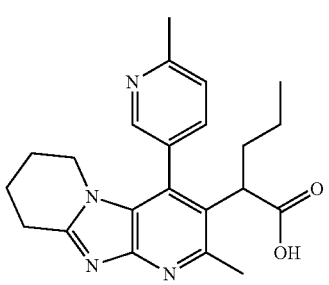 [SMILES: CCCC(C(=O)O)c1c(C)nc2nc3n(c2c1-c1ccc(C)nc1)CCCC3] |
| Cpd069 | 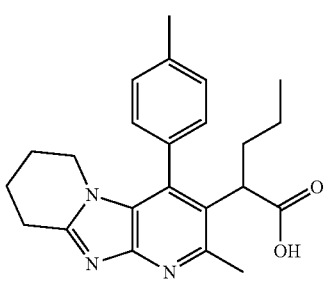 [SMILES: CCCC(C(=O)O)c1c(C)nc2nc3n(c2c1-c1ccc(C)cc1)CCCC3] |
| Cpd070 | 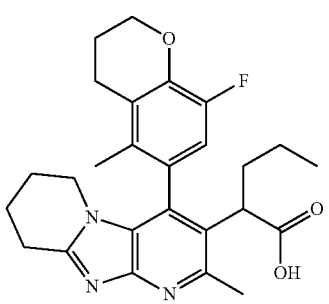 [SMILES: CCCC(C(=O)O)c1c(C)nc2nc3n(c2c1-c1cc(F)c2c(c1C)CCCO2)CCCC3] |
| Cpd071 | 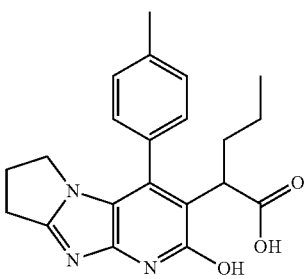 [SMILES: CCCC(C(=O)O)c1c(O)nc2nc3n(c2c1-c1ccc(C)cc1)CCC3] |
| Cpd072 | 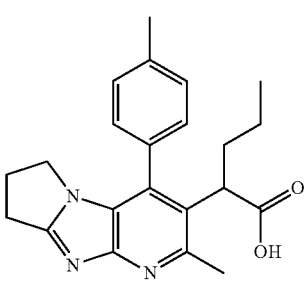 [SMILES: CCCC(C(=O)O)c1c(C)nc2nc3n(c2c1-c1ccc(C)cc1)CCC3] |

US 9,132,129 B2
TABLE 1-continued
Structures of example compounds of the invention and their respective codes.
CPD CODE  STRUCTURE
Cpd073
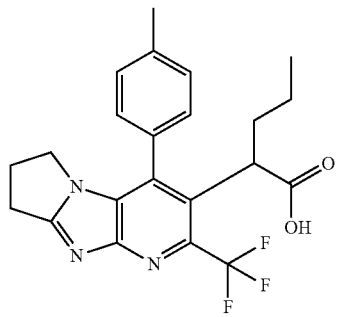 [SMILES: CCCC(C(=O)O)c1c(C(F)(F)F)nc2nc3n(c2c1-c1ccc(C)cc1)CCC3]
Cpd074
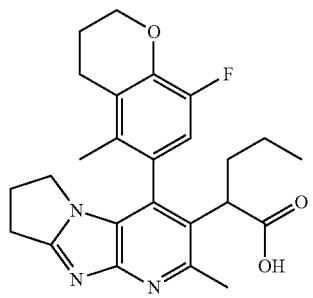 [SMILES: CCCC(C(=O)O)c1c(C)nc2nc3n(c2c1-c1cc(F)c2c(c1C)CCCO2)CCC3]
Cpd075
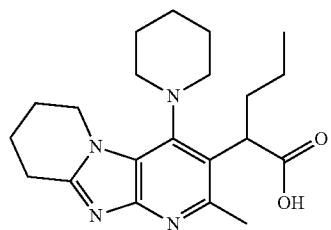 [SMILES: CCCC(C(=O)O)c1c(C)nc2nc3n(c2c1N1CCCCC1)CCCC3]
Cpd076
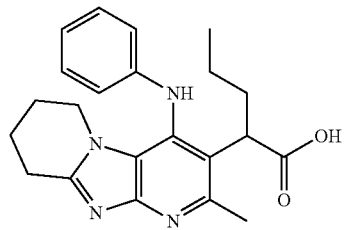
Cpd077
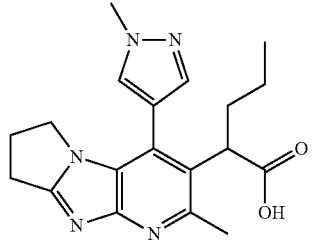 [SMILES: CCCC(C(=O)O)c1c(C)nc2nc3n(c2c1-c1cnn(C)c1)CCC3]
TABLE 1-continued
Structures of example compounds of the invention and their respective codes.
CPD CODE  STRUCTURE
Cpd078
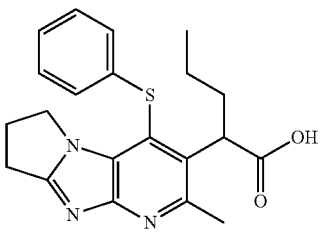
Cpd079
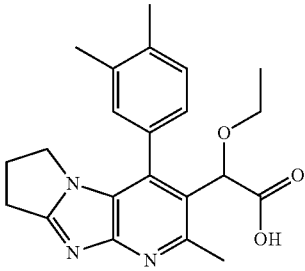 [SMILES: CCOC(C(=O)O)c1c(C)nc2nc3n(c2c1-c1ccc(C)c(C)c1)CCC3]
Cpd080
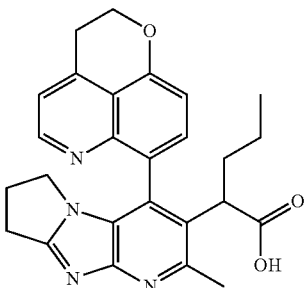
Cpd081
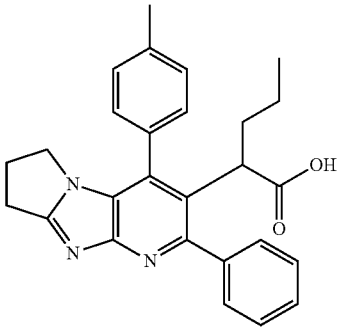 [SMILES: CCCC(C(=O)O)c1c(-c2ccccc2)nc2nc3n(c2c1-c1ccc(C)cc1)CCC3]
Cpd082
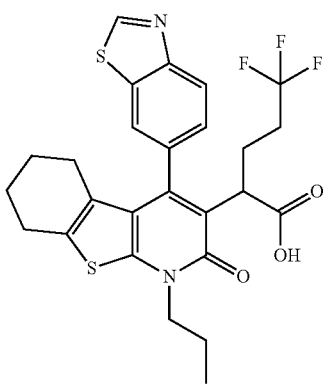 [SMILES: CCCn1c(=O)c(C(CCC(F)(F)F)C(=O)O)c(-c2ccc3ncsc3c2)c2c3c(sc21)CCCC3]

TABLE 1-continued
Structures of example compounds of the invention and their respective codes.
CPD CODE   STRUCTURE
Cpd083
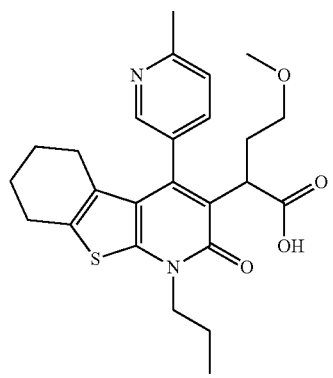 [SMILES: CCCn1c(=O)c(C(CCOC)C(=O)O)c(-c2ccc(C)nc2)c2c3c(sc21)CCCC3]
Cpd084
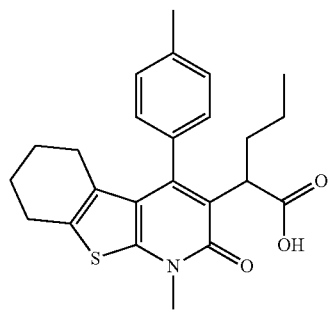 [SMILES: CCCC(C(=O)O)c1c(-c2ccc(C)cc2)c2c3c(sc2n(C)c1=O)CCCC3]
Cpd085
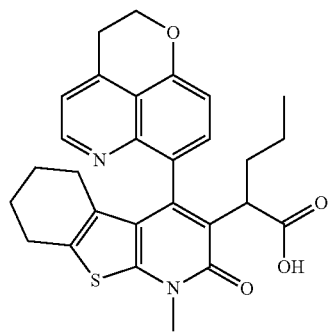 [SMILES: CCCC(C(=O)O)c1c(-c2ccc3c4c(ccnc24)CCO3)c2c3c(sc2n(C)c1=O)CCCC3]
Cpd086
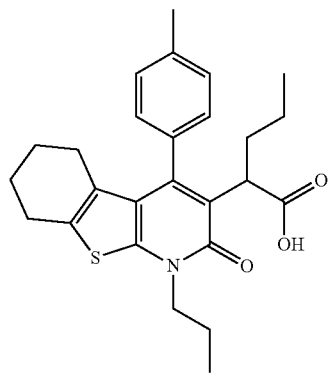 [SMILES: CCCC(C(=O)O)c1c(-c2ccc(C)cc2)c2c3c(sc2n(CCC)c1=O)CCCC3]
TABLE 1-continued
Structures of example compounds of the invention and their respective codes.
CPD CODE   STRUCTURE
Cpd087
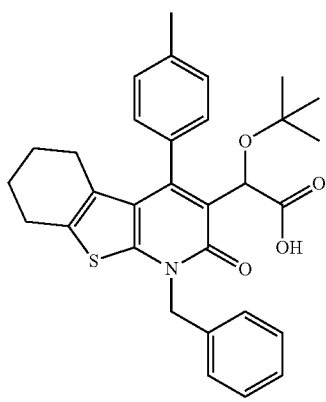 [SMILES: Cc1ccc(-c2c(C(OC(C)(C)C)C(=O)O)c(=O)n(Cc3ccccc3)c3sc4c(c23)CCCC4)cc1]
Cpd088
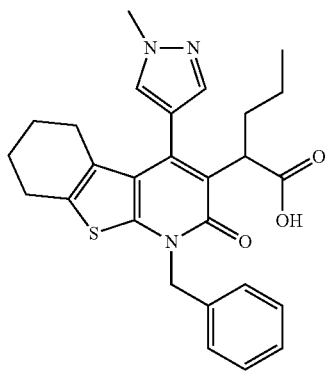 [SMILES: CCCC(C(=O)O)c1c(-c2cnn(C)c2)c2c3c(sc2n(Cc2ccccc2)c1=O)CCCC3]
Cpd089
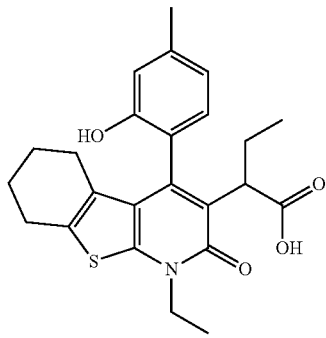 [SMILES: CCC(C(=O)O)c1c(-c2ccc(C)cc2O)c2c3c(sc2n(CC)c1=O)CCCC3]
Cpd090
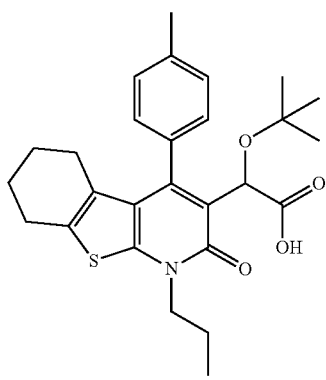 [SMILES: CCCn1c(=O)c(C(OC(C)(C)C)C(=O)O)c(-c2ccc(C)cc2)c2c3c(sc21)CCCC3]

TABLE 1-continued
Structures of example compounds of the invention and their respective codes.
CPD CODE   STRUCTURE
Cpd091
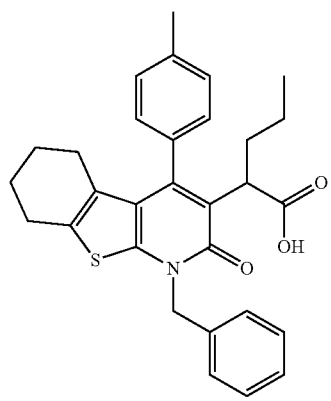 [SMILES: CCCC(C(=O)O)c1c(-c2ccc(C)cc2)c2c3c(sc2n(Cc2ccccc2)c1=O)CCCC3]
Cpd092
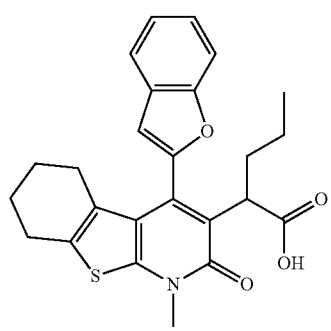 [SMILES: CCCC(C(=O)O)c1c(-c2cc3ccccc3o2)c2c3c(sc2n(C)c1=O)CCCC3]
Cpd093
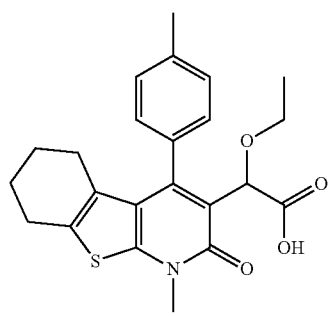 [SMILES: CCOC(C(=O)O)c1c(-c2ccc(C)cc2)c2c3c(sc2n(C)c1=O)CCCC3]
Cpd094
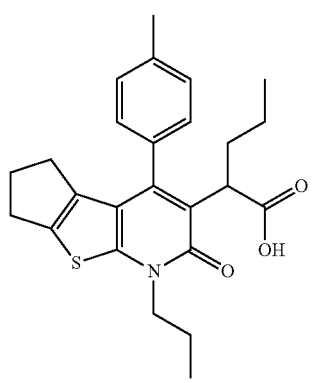 [SMILES: CCCC(C(=O)O)c1c(-c2ccc(C)cc2)c2c3c(sc2n(CCC)c1=O)CCC3]
TABLE 1-continued
Structures of example compounds of the invention and their respective codes.
CPD CODE   STRUCTURE
Cpd095
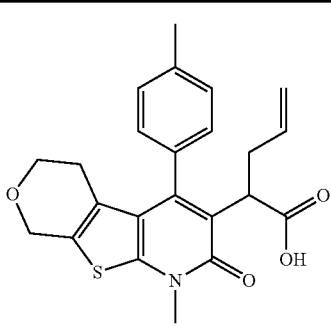
Cpd096
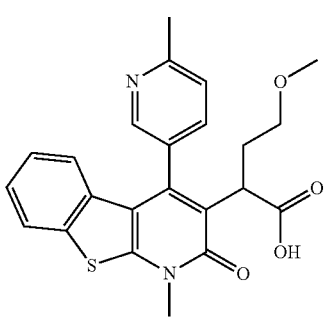 [SMILES: COCCC(C(=O)O)c1c(-c2ccc(C)nc2)c2c3ccccc3sc2n(C)c1=O]
Cpd097
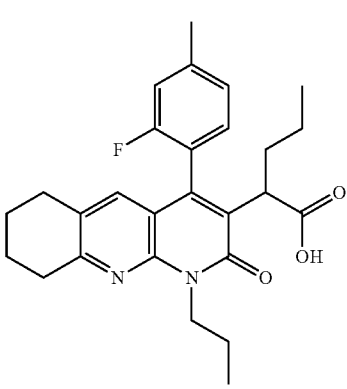 [SMILES: CCCC(C(=O)O)c1c(-c2ccc(C)cc2F)c2cc3c(nc2n(CCC)c1=O)CCCC3]
Cpd098
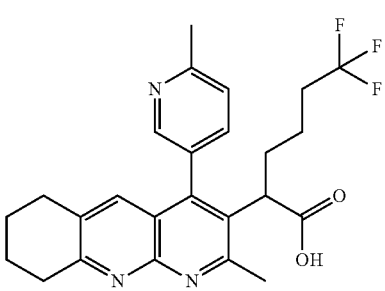 [SMILES: Cc1ccc(-c2c(C(CCCC(F)(F)F)C(=O)O)c(C)nc3nc4c(cc23)CCCC4)cn1]

TABLE 1-continued
Structures of example compounds of the invention and their respective codes.
CPD CODE  STRUCTURE
Cpd099
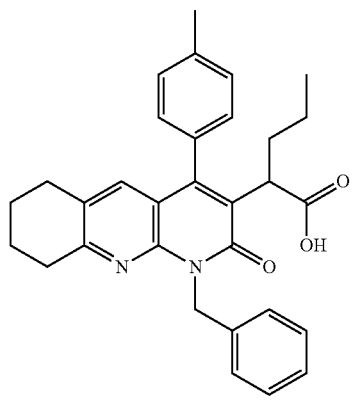 [SMILES: CCCC(C(=O)O)c1c(-c2ccc(C)cc2)c2cc3c(nc2n(Cc2ccccc2)c1=O)CCCC3]
Cpd100
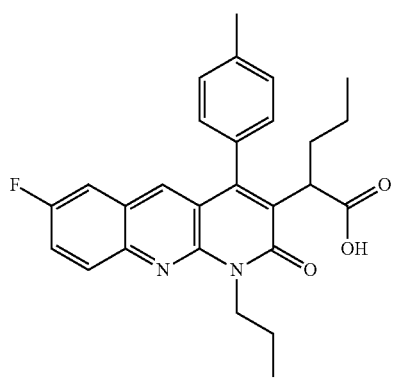 [SMILES: CCCC(C(=O)O)c1c(-c2ccc(C)cc2)c2cc3cc(F)ccc3nc2n(CCC)c1=O]
Cpd101
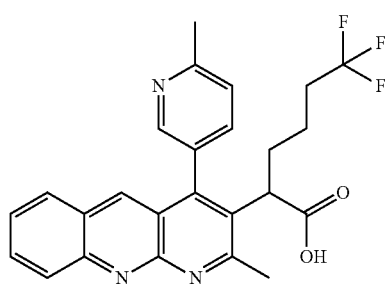 [SMILES: Cc1ccc(-c2c(C(CCCC(F)(F)F)C(=O)O)c(C)nc3nc4ccccc4cc23)cn1]
Cpd102
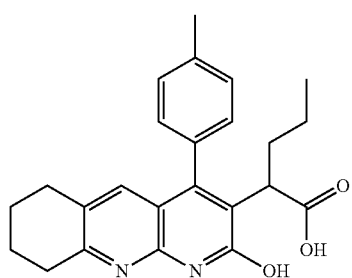 [SMILES: CCCC(C(=O)O)c1c(O)nc2nc3c(cc2c1-c1ccc(C)cc1)CCCC3]
TABLE 1-continued
Structures of example compounds of the invention and their respective codes.
CPD CODE  STRUCTURE
Cpd103
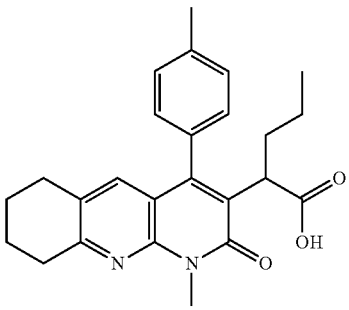 [SMILES: CCCC(C(=O)O)c1c(-c2ccc(C)cc2)c2cc3c(nc2n(C)c1=O)CCCC3]
Cpd104
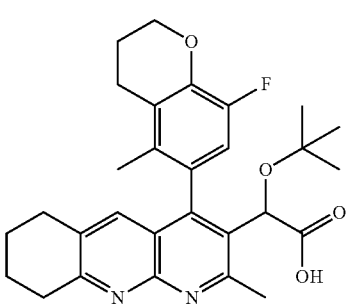 [SMILES: Cc1nc2nc3c(cc2c(-c2cc(F)c4c(c2C)CCCO4)c1C(OC(C)(C)C)C(=O)O)CCCC3]
Cpd105
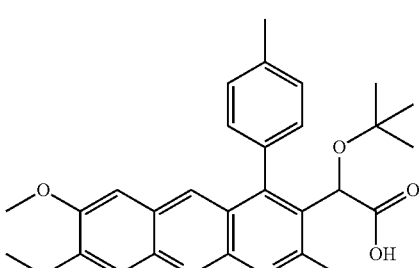
Cpd106
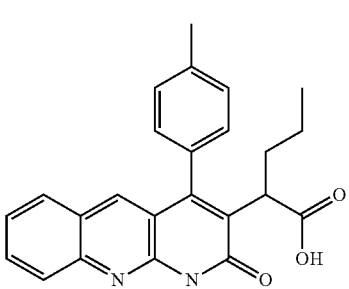
Cpd107
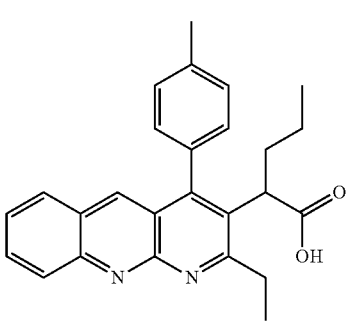 [SMILES: CCCC(C(=O)O)c1c(CC)nc2nc3ccccc3cc2c1-c1ccc(C)cc1]

TABLE 1-continued
Structures of example compounds of the invention and their respective codes.
CPD CODE  STRUCTURE
Cpd108
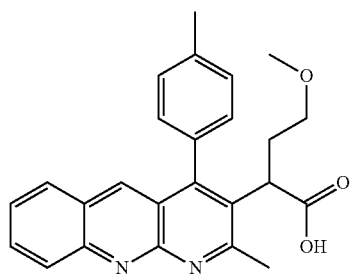 [SMILES: COCCC(C(=O)O)c1c(C)nc2nc3ccccc3cc2c1-c1ccc(C)cc1]
Cpd109
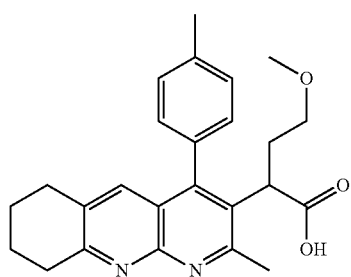 [SMILES: COCCC(C(=O)O)c1c(C)nc2nc3c(cc2c1-c1ccc(C)cc1)CCCC3]
Cpd110
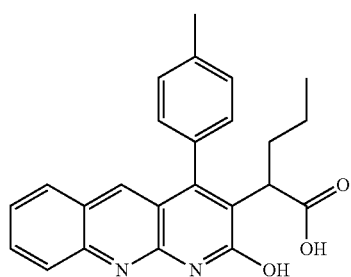 [SMILES: CCCC(C(=O)O)c1c(O)nc2nc3ccccc3cc2c1-c1ccc(C)cc1]
Cpd111
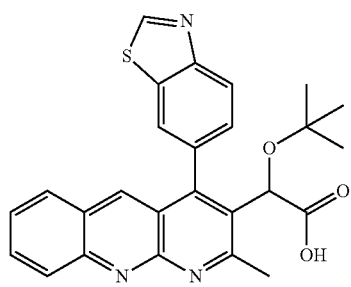 [SMILES: Cc1nc2nc3ccccc3cc2c(-c2ccc3ncsc3c2)c1C(OC(C)(C)C)C(=O)O]
Cpd112
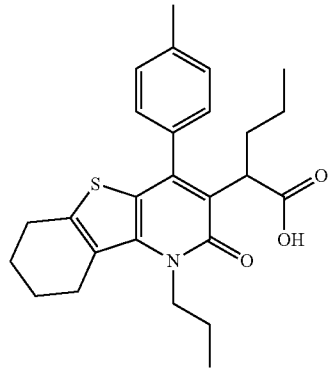 [SMILES: CCCC(C(=O)O)c1c(-c2ccc(C)cc2)c2sc3c(c2n(CCC)c1=O)CCCC3]
TABLE 1-continued
Structures of example compounds of the invention and their respective codes.
CPD CODE  STRUCTURE
Cpd113
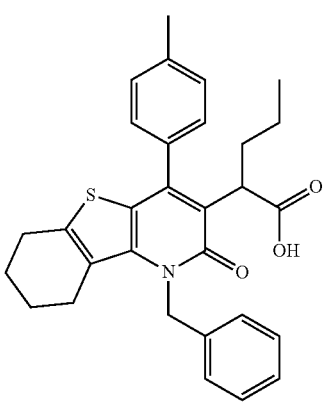 [SMILES: CCCC(C(=O)O)c1c(-c2ccc(C)cc2)c2sc3c(c2n(Cc2ccccc2)c1=O)CCCC3]
Cpd114
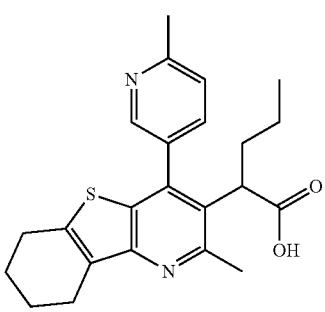 [SMILES: CCCC(C(=O)O)c1c(C)nc2c3c(sc2c1-c1ccc(C)nc1)CCCC3]
Cpd115
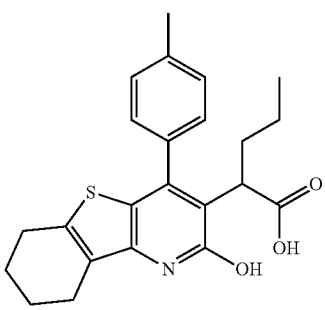 [SMILES: CCCC(C(=O)O)c1c(O)nc2c3c(sc2c1-c1ccc(C)cc1)CCCC3]
Cpd116
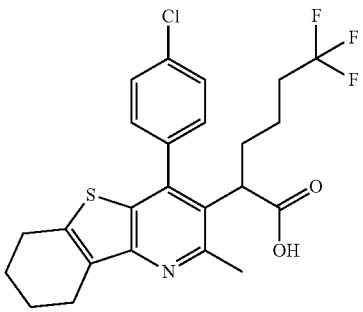 [SMILES: Cc1nc2c3c(sc2c(-c2ccc(Cl)cc2)c1C(CCCC(F)(F)F)C(=O)O)CCCC3]

TABLE 1-continued
Structures of example compounds of the invention and their respective codes.
CPD CODE  STRUCTURE
Cpd117
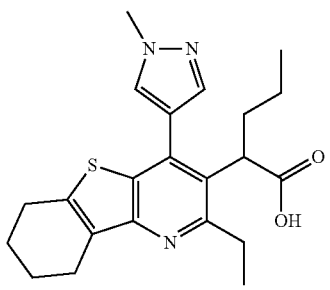 [SMILES: CCCC(C(=O)O)c1c(CC)nc2c3c(sc2c1-c1cnn(C)c1)CCCC3]
Cpd118
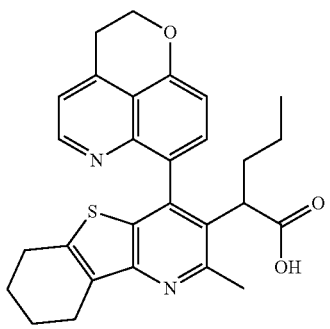 [SMILES: CCCC(C(=O)O)c1c(C)nc2c3c(sc2c1-c1ccc2c4c(ccnc14)CCO2)CCCC3]
Cpd119
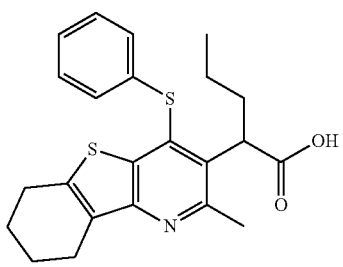
Cpd120
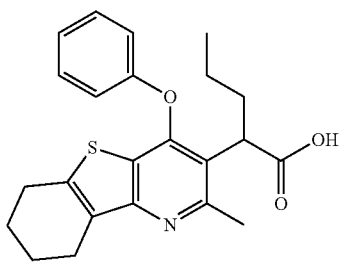 [SMILES: CCCC(C(=O)O)c1c(C)nc2c3c(sc2c1Oc1ccccc1)CCCC3]
Cpd121
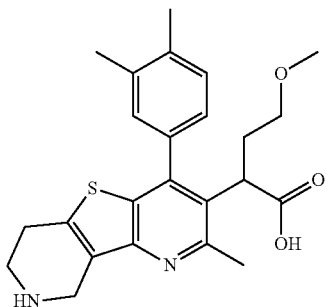 [SMILES: COCCC(C(=O)O)c1c(C)nc2c3c(sc2c1-c1ccc(C)c(C)c1)CCNC3]
TABLE 1-continued
Structures of example compounds of the invention and their respective codes.
CPD CODE  STRUCTURE
Cpd122
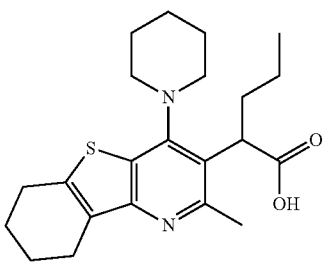 [SMILES: CCCC(C(=O)O)c1c(C)nc2c3c(sc2c1N1CCCCC1)CCCC3]
Cpd123
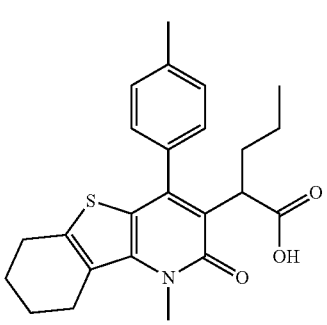 [SMILES: CCCC(C(=O)O)c1c(-c2ccc(C)cc2)c2sc3c(c2n(C)c1=O)CCCC3]
Cpd124
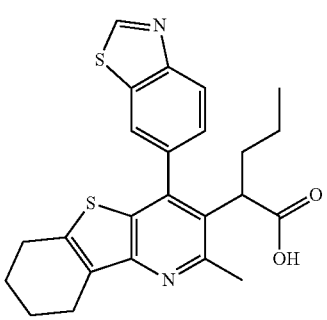 [SMILES: CCCC(C(=O)O)c1c(C)nc2c3c(sc2c1-c1ccc2ncsc2c1)CCCC3]
Cpd125
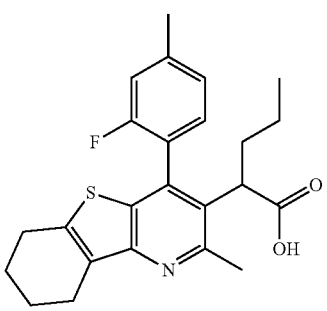 [SMILES: CCCC(C(=O)O)c1c(C)nc2c3c(sc2c1-c1ccc(C)cc1F)CCCC3]
Cpd126
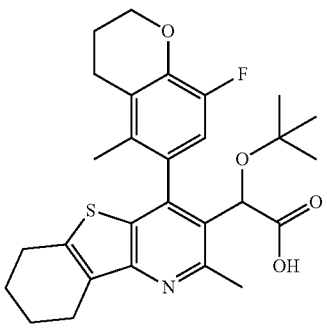 [SMILES: Cc1nc2c3c(sc2c(-c2cc(F)c4c(c2C)CCCO4)c1C(OC(C)(C)C)C(=O)O)CCCC3]

TABLE 1-continued
Structures of example compounds of the invention and their respective codes.
CPD CODE  STRUCTURE
Cpd127
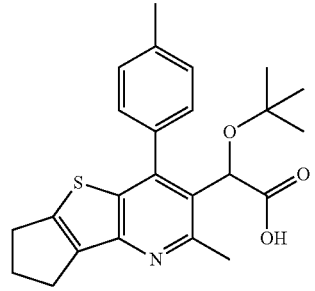 [SMILES: Cc1ccc(-c2c(C(OC(C)(C)C)C(=O)O)c(C)nc3c4c(sc23)CCC4)cc1]
Cpd128
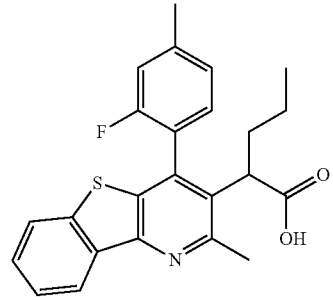 [SMILES: CCCC(C(=O)O)c1c(C)nc2c(sc3ccccc32)c1-c1ccc(C)cc1F]
Cpd129
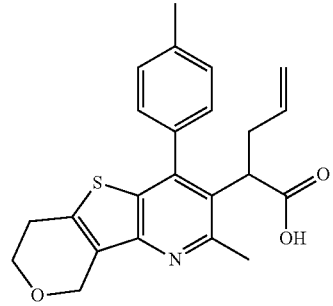 [SMILES: C=CCC(C(=O)O)c1c(C)nc2c3c(sc2c1-c1ccc(C)cc1)CCOC3]
Cpd130
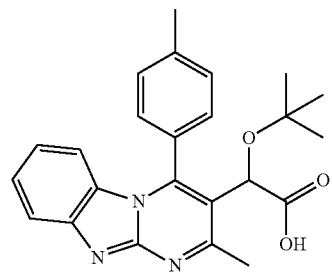 [SMILES: Cc1ccc(-c2c(C(OC(C)(C)C)C(=O)O)c(C)nc3nc4ccccc4n23)cc1]
Cpd131
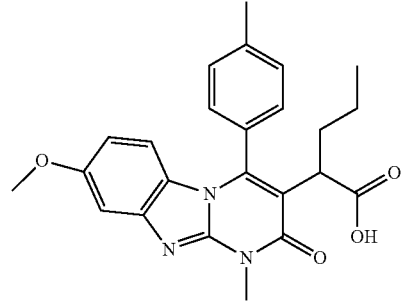 [SMILES: CCCC(C(=O)O)c1c(-c2ccc(C)cc2)n2c3ccc(OC)cc3nc2n(C)c1=O]
TABLE 1-continued
Structures of example compounds of the invention and their respective codes.
CPD CODE  STRUCTURE
Cpd132
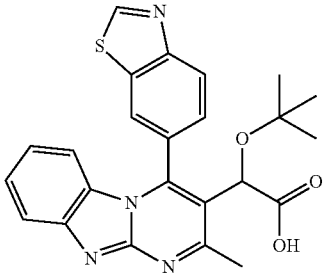 [SMILES: Cc1nc2nc3ccccc3n2c(-c2ccc3ncsc3c2)c1C(OC(C)(C)C)C(=O)O]
Cpd133
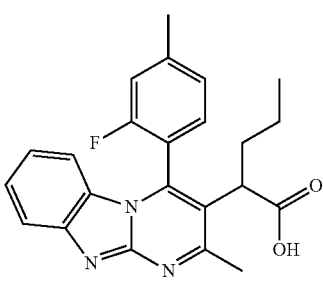 [SMILES: CCCC(C(=O)O)c1c(C)nc2nc3ccccc3n2c1-c1ccc(C)cc1F]
Cpd134
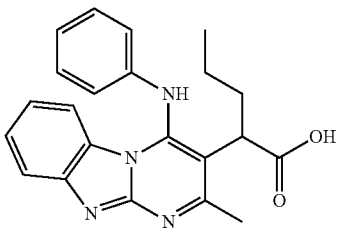 [SMILES: CCCC(C(=O)O)c1c(C)nc2nc3ccccc3n2c1Nc1ccccc1]
Cpd135
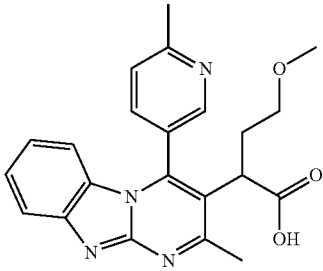 [SMILES: COCCC(C(=O)O)c1c(C)nc2nc3ccccc3n2c1-c1ccc(C)nc1]
Cpd136
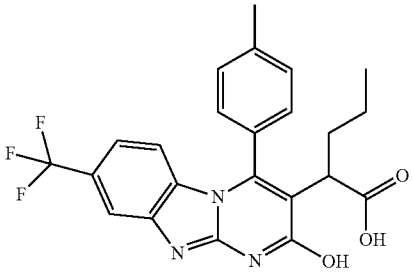 [SMILES: CCCC(C(=O)O)c1c(O)nc2nc3cc(C(F)(F)F)ccc3n2c1-c1ccc(C)cc1]

TABLE 1-continued
Structures of example compounds of the invention and their respective codes.
CPD CODE  STRUCTURE
Cpd137
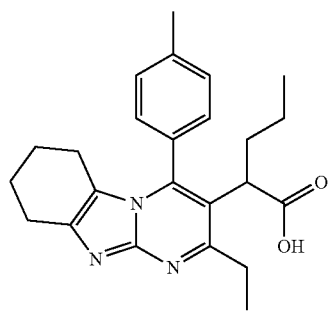 [SMILES: CCCC(C(=O)O)c1c(CC)nc2nc3c(n2c1-c1ccc(C)cc1)CCCC3]
Cpd138
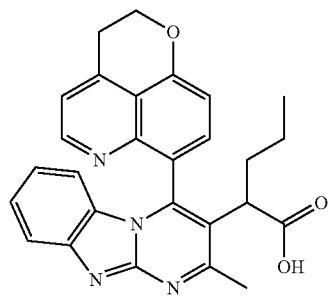 [SMILES: CCCC(C(=O)O)c1c(C)nc2nc3ccccc3n2c1-c1ccc2c3c(ccnc13)CCO2]
Cpd139
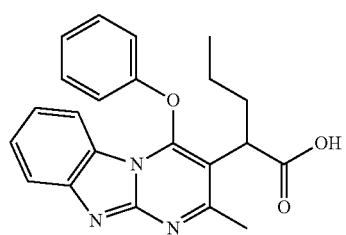 [SMILES: CCCC(C(=O)O)c1c(C)nc2nc3ccccc3n2c1Oc1ccccc1]
Cpd140
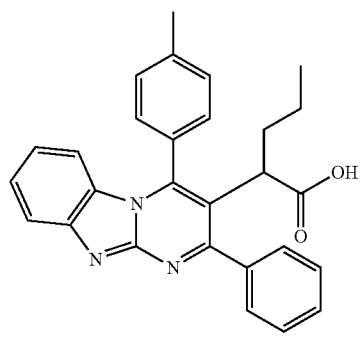 [SMILES: CCCC(C(=O)O)c1c(-c2ccccc2)nc2nc3ccccc3n2c1-c1ccc(C)cc1]
Cpd141
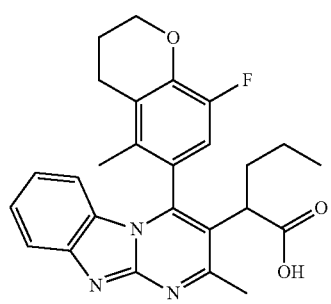 [SMILES: CCCC(C(=O)O)c1c(C)nc2nc3ccccc3n2c1-c1cc(F)c2c(c1C)CCCO2]
TABLE 1-continued
Structures of example compounds of the invention and their respective codes.
CPD CODE  STRUCTURE
Cpd142
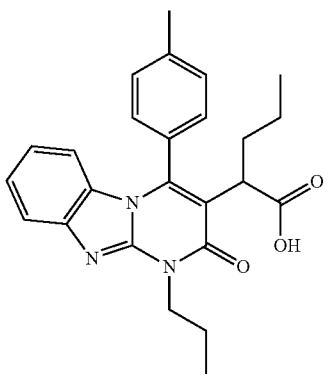 [SMILES: CCCC(C(=O)O)c1c(-c2ccc(C)cc2)n2c3ccccc3nc2n(CCC)c1=O]
Cpd143
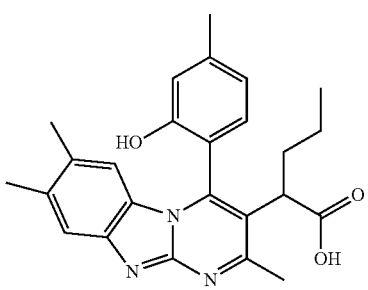 [SMILES: CCCC(C(=O)O)c1c(C)nc2nc3cc(C)c(C)cc3n2c1-c1ccc(C)cc1O]
Cpd144
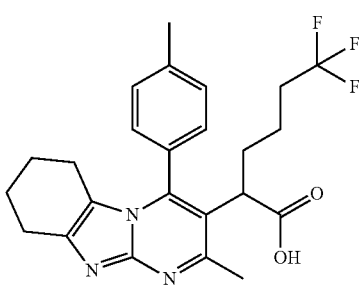 [SMILES: Cc1ccc(-c2c(C(CCCC(F)(F)F)C(=O)O)c(C)nc3nc4c(n23)CCCC4)cc1]
Cpd145
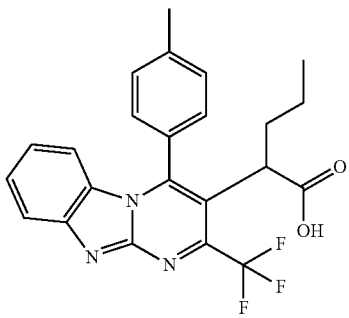 [SMILES: CCCC(C(=O)O)c1c(C(F)(F)F)nc2nc3ccccc3n2c1-c1ccc(C)cc1]
Cpd146
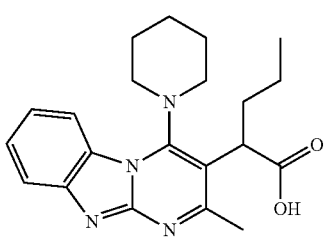 [SMILES: CCCC(C(=O)O)c1c(C)nc2nc3ccccc3n2c1N1CCCCC1]

TABLE 1-continued
Structures of example compounds of the invention and their respective codes.
CPD CODE  STRUCTURE
Cpd147
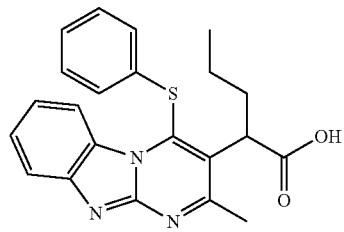 [SMILES: CCCC(C(=O)O)c1c(C)nc2nc3ccccc3n2c1Sc1ccccc1]
Cpd148
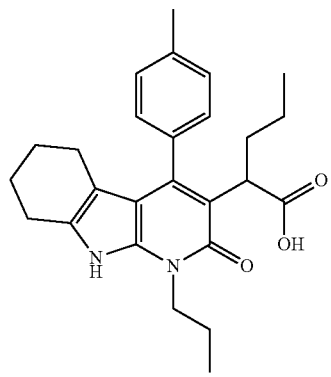 [SMILES: CCCC(C(=O)O)c1c(-c2ccc(C)cc2)c2c3c([nH]c2n(CCC)c1=O)CCCC3]
Cpd149
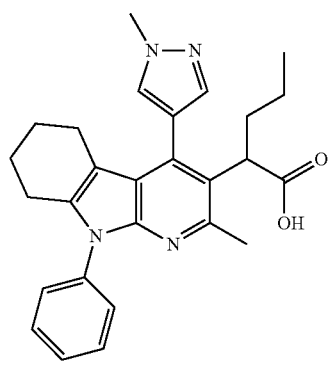 [SMILES: CCCC(C(=O)O)c1c(C)nc2c(c3c(n2-c2ccccc2)CCCC3)c1-c1cnn(C)c1]
Cpd150
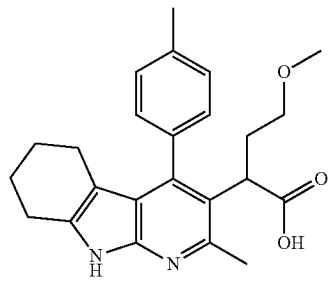 [SMILES: COCCC(C(=O)O)c1c(C)nc2[nH]c3c(c2c1-c1ccc(C)cc1)CCCC3]
TABLE 1-continued
Structures of example compounds of the invention and their respective codes.
CPD CODE  STRUCTURE
Cpd151
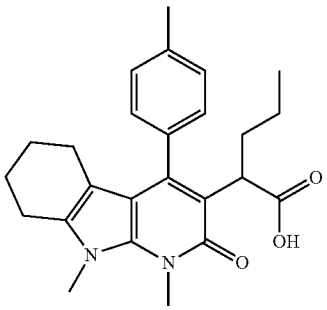 [SMILES: CCCC(C(=O)O)c1c(-c2ccc(C)cc2)c2c3c(n(C)c2n(C)c1=O)CCCC3]
Cpd152
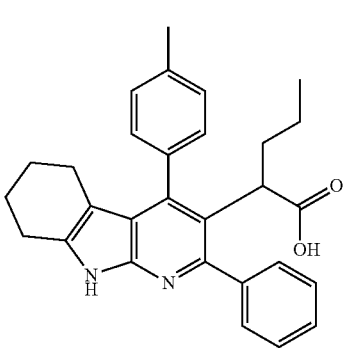 [SMILES: CCCC(C(=O)O)c1c(-c2ccccc2)nc2[nH]c3c(c2c1-c1ccc(C)cc1)CCCC3]
Cpd153
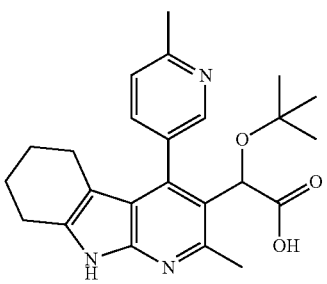 [SMILES: Cc1ccc(-c2c(C(OC(C)(C)C)C(=O)O)c(C)nc3[nH]c4c(c23)CCCC4)cn1]
Cpd154
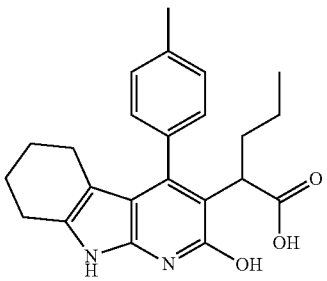 [SMILES: CCCC(C(=O)O)c1c(O)nc2[nH]c3c(c2c1-c1ccc(C)cc1)CCCC3]

TABLE 1-continued

Structures of example compounds of the invention and their respective codes.

| CPD CODE | STRUCTURE |
|---|---|
| Cpd155 | 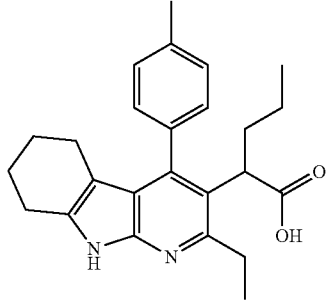 [SMILES: CCCC(C(=O)O)c1c(CC)nc2[nH]c3c(c2c1-c1ccc(C)cc1)CCCC3] |

Part A: Examples Describing the Materials Used, General Preparation Methods and Synthesis of Compounds of the Invention All the preparative HPLC purifications mentioned in this experimental part have been carried out with the following system: a Waters 2489 UV/Visible Detector, a Waters 2545 Binary Gradient Module, a Waters Fraction Collector III and a Waters Dual Flex Injector.

The separations were performed with a SunFire Prep C18 ODB column (5 μm; 19×100 mm) equipped with a SunFire C18 guard column (5 μm; 19×10 mm). Elutions were carried out with the methods described in the following tables, and detection wavelengths were fixed at 210 and 254 nm.

HPLC method 1

| Time (min) | Flow Rate (mL/min) | Solvent A (%) | Solvent B (%) |
|---|---|---|---|
| 0 | 20 | 80 | 20 |
| 2.00 | 20 | 80 | 20 |
| 8.00 | 20 | 10 | 90 |
| 10.80 | 20 | 10 | 90 |
| 11.00 | 20 | 80 | 20 |
| 16.00 | 20 | 80 | 20 |

Solvent A: Formic Acid LC-MS grade 0.1% in milliQ water
Solvent B: Acetonitrile HPLC grade.

HPLC method 2

| Time (min) | Flow Rate (mL/min) | Solvent A (%) | Solvent B (%) |
|---|---|---|---|
| 0 | 20 | 50 | 50 |
| 2.00 | 20 | 50 | 50 |
| 9.00 | 20 | 10 | 90 |
| 11.00 | 20 | 10 | 90 |
| 11.20 | 20 | 50 | 50 |
| 16.00 | 20 | 50 | 50 |

Solvent A: Formic Acid LC-MS grade 0.1% in milliQ water
Solvent B: Acetonitrile HPLC grade.

Example 1

Preparation of 2-(2-methyl-4-p-tolylpyrimido[1,2-b]indazol-3-yl)pentanoic acid (Cpd 047)

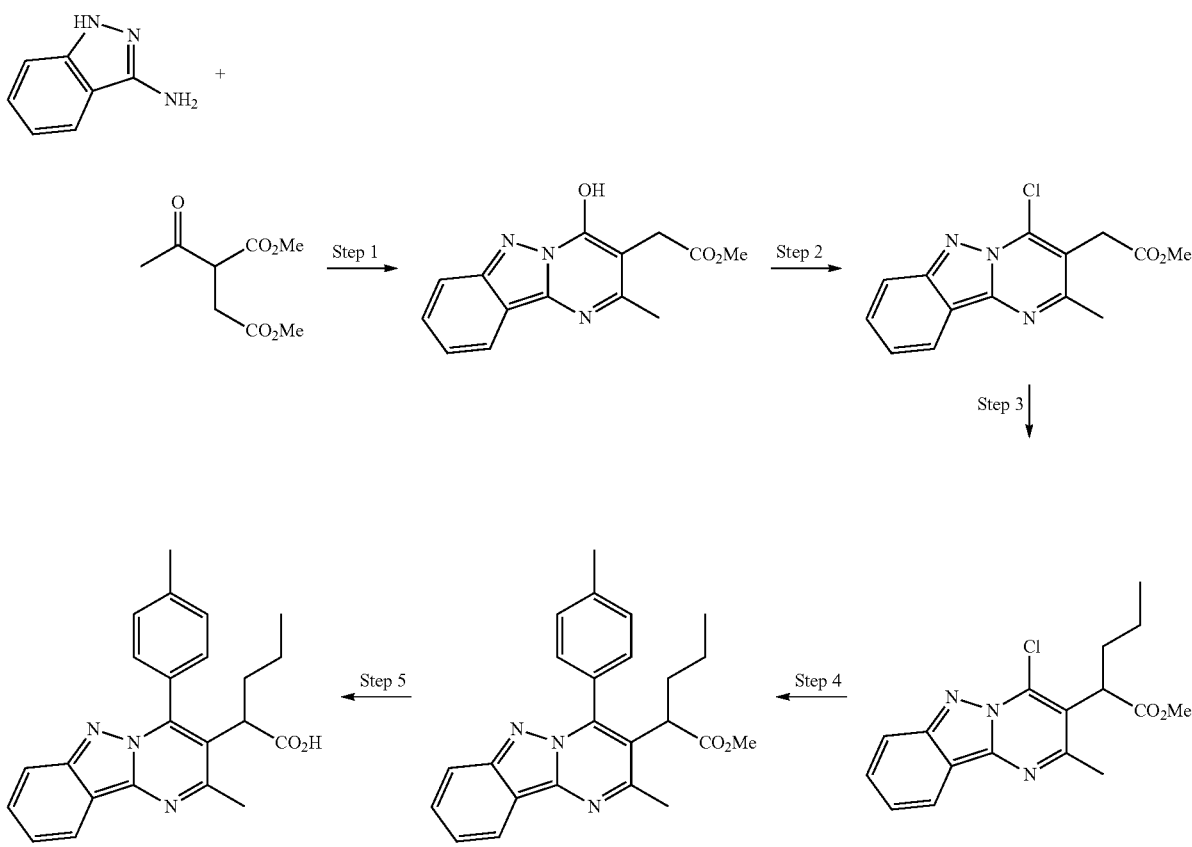

Step 1:
A mixture of a dimethyl acetylsuccinate (1.55 g; 8.27 mmol) and 1H-indazol-3-amine (1 g; 7.5 mmol) in toluene (7.5 mL) was heated to reflux under a Dean Stark system for 48 h. The precipitate was filtered-off, washed with toluene and diethylether to afford 1.34 g (67%) of methyl 2-(4-hydroxy-2-methylpyrimido[1,2-b]indazol-3-yl)acetate, which was used for the next step without any further purification. ESI/APCI(+): 272 (M+H).

Step 2:
The methyl 2-(4-hydroxy-2-methylpyrimido[1,2-b]indazol-3-yl)acetate (1.34 g; 4.94 mmol) was suspended in phosphorus oxychloride (5.1 mL) and dimethylaniline (0.96 mL) was added under nitrogen atmosphere. The well-stirred reaction mixture was heated at 60° C. for 3 days. Phosphorus oxychloride in excess was removed under reduced pressure and the remaining oil was placed in an ice-bath. A cold saturated sodium hydrogenocarbonate solution was carefully added until neutralization. The aqueous layer was extracted with ethyl acetate, the organics were combined, dried over sodium sulfate, concentrated under reduced pressure. Purification by flash chromatography on silica gel using a gradient of ethyl acetate (1-20%) in dichloromethane furnished 0.659 g (46%) of methyl 2-(4-chloro-2-methylpyrimido[1,2-b]indazol-3-yl)acetate as a light yellow solid. ESI/APCI(+): 290-292 (M+H).

Step 3:
To a solution of methyl 2-(4-chloro-2-methylpyrimido[1,2-b]indazol-3-yl)acetate (0.289 g; 1 mmol) in dry DMF (4 mL) at −10° C. was slowly added a 1N solution of LHMDS in tetrahydrofuran (1.1 mL; 1.1 mmol). Then, 1-iodopropane (0.146 mL; 1.5 mmol) was added and the reaction mixture was stirred at room temperature for 20 h. The reaction mixture was quenched by addition of a saturated solution of ammonium chloride and the mixture was extracted with ethyl acetate. The organic layer was washed with water, brine, dried over sodium sulfate and concentrated under reduced pressure. Purification by flash chromatography on silica gel using a gradient of ethyl acetate (2-20%) in dichloromethane furnished 0.252 g (76%) of methyl 2-(4-chloro-2-methylpyrimido[1,2-b]indazol-3-yl)pentanoate as an oil. ESI/APCI(+): 332-334 (M+H).

Step 4:
To a sonicated solution of methyl 2-(4-chloro-2-methylpyrimido[1,2-b]indazol-3-yl)pentanoate (0.252 g; 0.74 mmol) and 4-methylphenylboronic acid (0.201 mg; 1.48 mmol) in a mixture of water/DME (⅓, 3 mL) were added palladiumtetrakistriphenylphosphine (0.128 mg; 0.11 mmol) and diisopropylethylamine (0.368 mL; 2.22 mmol). The solution was stirred for 20 min at 140° C. under microwave irradiation. Ethyl acetate was added to the reaction mixture and the solution was washed with a 1N hydrochloric acid solution, a 1N sodium hydrogenocarbonate and brine. The organic phase was dried over magnesium sulfate, filtered and concentrated under reduced pressure. Purification by flash chromatography on silica gel using a gradient of ethyl acetate (1-40%) in dichloromethane furnished 0.264 g (90%) of methyl 2-(2-methyl-4-p-tolylpyrimido[1,2-b]indazol-3-yl)pentanoate as an oil. ESI/APCI(+): 388 (M+H).

Step 5:
To a solution of methyl 2-(2-methyl-4-p-tolylpyrimido[1,2-b]indazol-3-yl)pentanoate (0.264 g; 0.68 mmol) in a mixture methanol-ethanol (2:1) (21 mL) was added a 5% sodium hydroxide solution (16.3 mL; 20.4 mmol) and the reaction mixture was heated to 60° C. for 18 h. The organic volatiles were removed under reduced pressure and the remaining basic solution was acidified till pH 2 with a 1N hydrochloric acid solution and the aqueous layer was extracted with ethyl acetate. The organics were combined, dried over magnesium sulfate and concentrated under reduced pressure. Purification by flash chromatography on silica gel using a gradient of methanol (1-20%) in dichloromethane and by preparative HPLC (method 2) furnished 0.076 g (30%) of 2-(2-methyl-4-p-tolylpyrimido[1,2-b]indazol-3-yl)pentanoic acid as a white solid. ESI/APCI(+): 374 (M+H). ESI/APCI(−): 372 (M−H).

Example 2

Preparation of 2-(-2-methyl-4-p-tolyl-6,7,8,9-tetrahydrobenzo[g]quinolin-3-yl)pentanoic acid and 2-(3-methyl-1-4-p-tolyl-7,8,9,10-tetrahydrobenzo[f]quinolin-2-yl)pentanoic acid (Cpd 001 and Cpd 003)

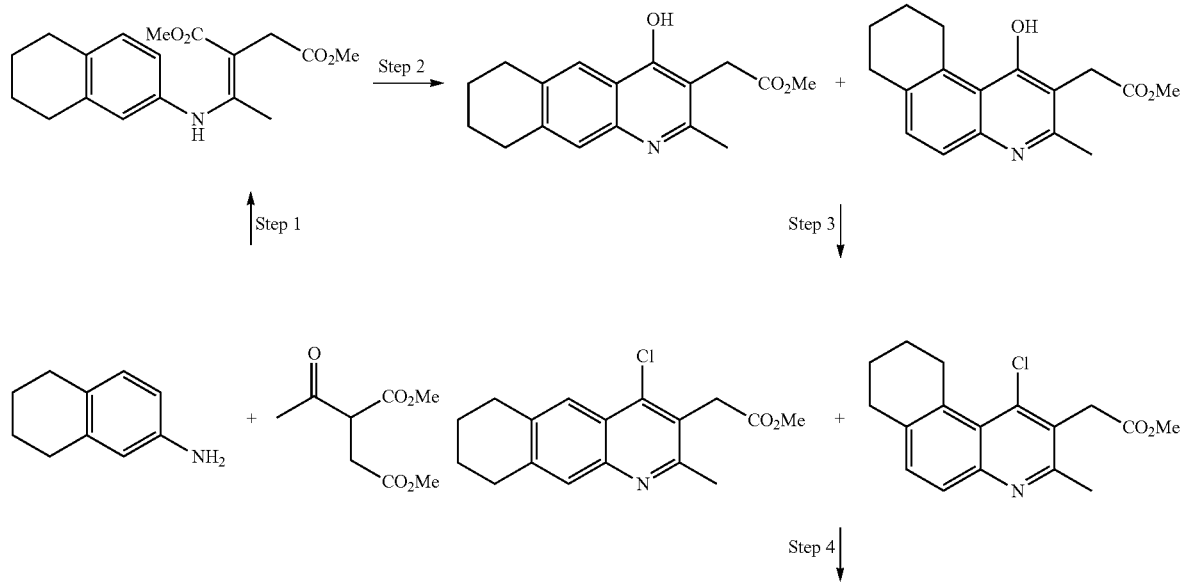

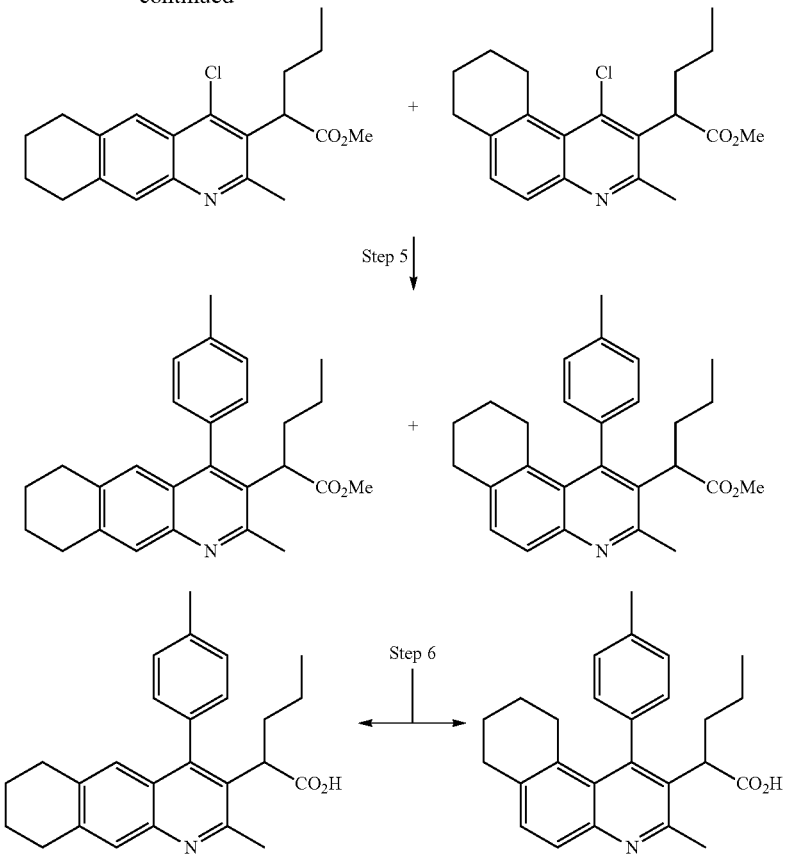

Step 1:

The 5,6,7,8-tetrahydronaphthalen-2-amine (10 g; 68 mmol) and dimethyl acetylsuccinate (11.6 g; 62 mmol) were mixed together, placed in a dessicator and the homogeneous mixture was stirred under vacuum (3 mbars) for 3 days. Purification by flash chromatography on silica gel using a gradient of ethyl acetate (1 to 20%) in heptane furnished 12.9 g (60%) of dimethyl 2-(1-(5,6,7,8-tetrahydronaphthalen-2-ylamino)ethylidene)succinate as a deep orange oil.

Step 2:

A solution of dimethyl 2-(1-(5,6,7,8-tetrahydronaphthalen-2-ylamino)ethylidene)succinate (12.9 g; 40 mmol) in diphenylether (40 mL) was divided in 4 fractions of 10 mL and each fraction was heated at 250° C. for 15 minutes in a microwave oven (20 mL Biotage reactor). The 4 batches were combined and ethanol (120 mL) was added. The mixture was placed in a sonication bath for 10 minutes and then left at room temperature for 15 minutes. The formed precipitate was filtered off, successively washed with ethanol, heptane, ethylacetate, diisopropylether and dried under reduced pressure over phosphorus pentoxide to furnish 4.9 g (39%) of a mixture of methyl 2-(4-hydroxy-2-methyl-6,7,8,9-tetrahydrobenzo[g]quinolin-3-yl)acetate and methyl 2-(1-hydroxy-3-methyl-7,8,9,10-tetrahydrobenzo[f]quinolin-2-yl)acetate as a yellow solid. ESI/APCI(+): 286 (M+H).

Step 3:

A mixture of methyl 2-(4-chloro-2-methyl-6,7,8,9-tetrahydrobenzo[g]quinolin-3-yl)acetate and methyl 2-(1-chloro-3-methyl-7,8,9,10-tetrahydrobenzo[f]quinolin-2-yl)acetate (4.9 g; 17.1 mmol) was dissolved in phosphorus oxychloride (17 mL) under a nitrogen atmosphere and the reaction mixture was heated at reflux for 4 h. After cooling, the volatiles were removed under reduced pressure and the reaction mixture was quenched by adding crushed-ice and a saturated solution of sodium hydrogen carbonate to pH 7. The product was extracted with ethyl acetate and the organic layers were collected, dried over magnesium sulfate and concentrated under reduced pressure. Purification by flash-chromatography on silica gel using a gradient of ethyl acetate (10-75%) in dichloromethane furnished 4.49 g (86%) of a mixture of methyl 2-(4-chloro-2-methyl-6,7,8,9-tetrahydrobenzo[g]quinolin-3-yl)acetate and methyl 2-(1-chloro-3-methyl-7,8,9,10-tetrahydrobenzo[f]quinolin-2-yl)acetate as a yellow solid. ESI/APCI(+): 304-306 (M+H). $^1$H NMR (DMSO-$d_6$) δ 7.78-7.41 (m, 4H, 4 Harom.); 4.07 (s, 4H, 2×CH$_2$); 3.66 (s, 6H, 2×CO$_2$CH$_3$); 3.34 (m, 3H, Hcyclohexyl); 2.95-2.91 (m, 5H, Hcyclohexyl); 2.61 (s, 6H, 2×CH$_3$); 1.81-1.73 (m, 8H, Hcyclohexyl).

Step 4:

To a solution of a mixture of methyl 2-(4-chloro-2-methyl-6,7,8,9-tetrahydrobenzo[g]quinolin-3-yl)acetate and methyl 2-(1-chloro-3-methyl-7,8,9,10-tetrahydrobenzo[f]quinolin-2-yl)acetate (0.911 g; 3 mmol) in dry DMF (12 mL) at −10° C. was added LHMDS (1M in THF) (3.3 mL; 3.3 mmol) and 1-iodopropane (0.439 mL; 4.5 mmol). The reaction mixture was allowed to warm up to room temperature and the reaction mixture was stirred for 20 h. A saturated ammonium chloride solution (12 ml) was added and the mixture was extracted with ethyl acetate. The organics were combined, washed with brine, dried over magnesium sulfate and concentrated under reduced pressure. Purification by flash-chromatography on silica gel using a gradient of ethyl acetate (2-30%) in dichloromethane furnished 0.544 g (52%) of a mixture of methyl 2-(4-chloro-2-methyl-6,7,8,9-tetrahydrobenzo[g]quinolin-3-yl)pentanoate and methyl 2-(1-chloro-3-methyl-7,8,9,10-tetrahydrobenzo[f]quinolin-2-yl)pentanoate as a light beige solid. ESI/APCI(+): 346-348 (M+H).

Step 5:

To a mixture of methyl 2-(4-chloro-2-methyl-6,7,8,9-tetrahydrobenzo[g]quinolin-3-yl)pentanoate and methyl 2-(1-chloro-3-methyl-7,8,9,10-tetrahydrobenzo[f]quinolin-2-yl)pentanoate (0.207 g; 0.6 mmol) dissolved in a mixture of 1,2-dimethoxyethane-water (3:1) (4.8 mL) were added 4-methylboronic acid (0.163 g; 1.2 mmol), tetrakis(triphenylphosphine)palladium (0.104 g; 0.09 mmol) and diisopropylethylamine (0.298 mL; 1.8 mmol) and the reaction mixture was heated at 100° C. for 48 h. After cooling, brine was added and the reaction mixture was extracted with ethyl acetate. The organic layers were combined, dried over magnesium sulfate and concentrated under reduced pressure. Purification by flash-chromatography on silica gel using a gradient of ethyl acetate (1-25%) in dichloromethane furnished 0.208 g (86%) of a mixture of methyl 2-(-2-methyl-4-p-tolyl-6,7,8,9-tetrahydrobenzo[g]quinolin-3-yl)pentanoate and methyl 2-(3-methyl-1-4-p-tolyl-7,8,9,10-tetrahydrobenzo[f]quinolin-2-yl)pentanoate as a bright yellow solid. ESI/APCI(+): 402 (M+H).

Step 6:

To a suspension of methyl 2-(2-methyl-4-p-tolyl-6,7,8,9-tetrahydrobenzo[g]quinolin-3-yl)pentanoate and methyl 2-(3-methyl-1-p-tolyl-7,8,9,10-tetrahydrobenzo[f]quinolin-2-yl)pentanoate (0.208 g; 0.518 mmol) in a mixture of methanol and ethanol (2:1) (15 mL) was added a 5% sodium hydroxide solution (15.54 mmol; 12.4 mL) and the reaction mixture was heated at reflux for 18 h. The organic volatiles were removed under reduced pressure and the remaining basic solution was acidified to pH 2 with a 1N hydrochloric solution. The precipitate was filtered and dried. Purification by preparative HPLC (method 2) furnished 0.066 g (33%) of a mixture of 2-(-2-methyl-4-p-tolyl-6,7,8,9-tetrahydrobenzo[g]quinolin-3-yl)pentanoic acid and 2-(3-methyl-1-4-p-tolyl-7,8,9,10-tetrahydrobenzo[f]quinolin-2-yl)pentanoic acid as a beige solid. ESI/APCI(+): 388 (M+H).

Example 3

Preparation of 2-(3-methyl-1-p-tolyl-8,9-dihydro-7H-cyclopenta[f]quinolin-2-yl)pentanoic acid and 2-(2-methyl-4-p-tolyl-7,8-dihydro-6H-cyclopenta[g]quinolin-3-yl)pentanoic acid (Cpd 012 and Cpd 023)

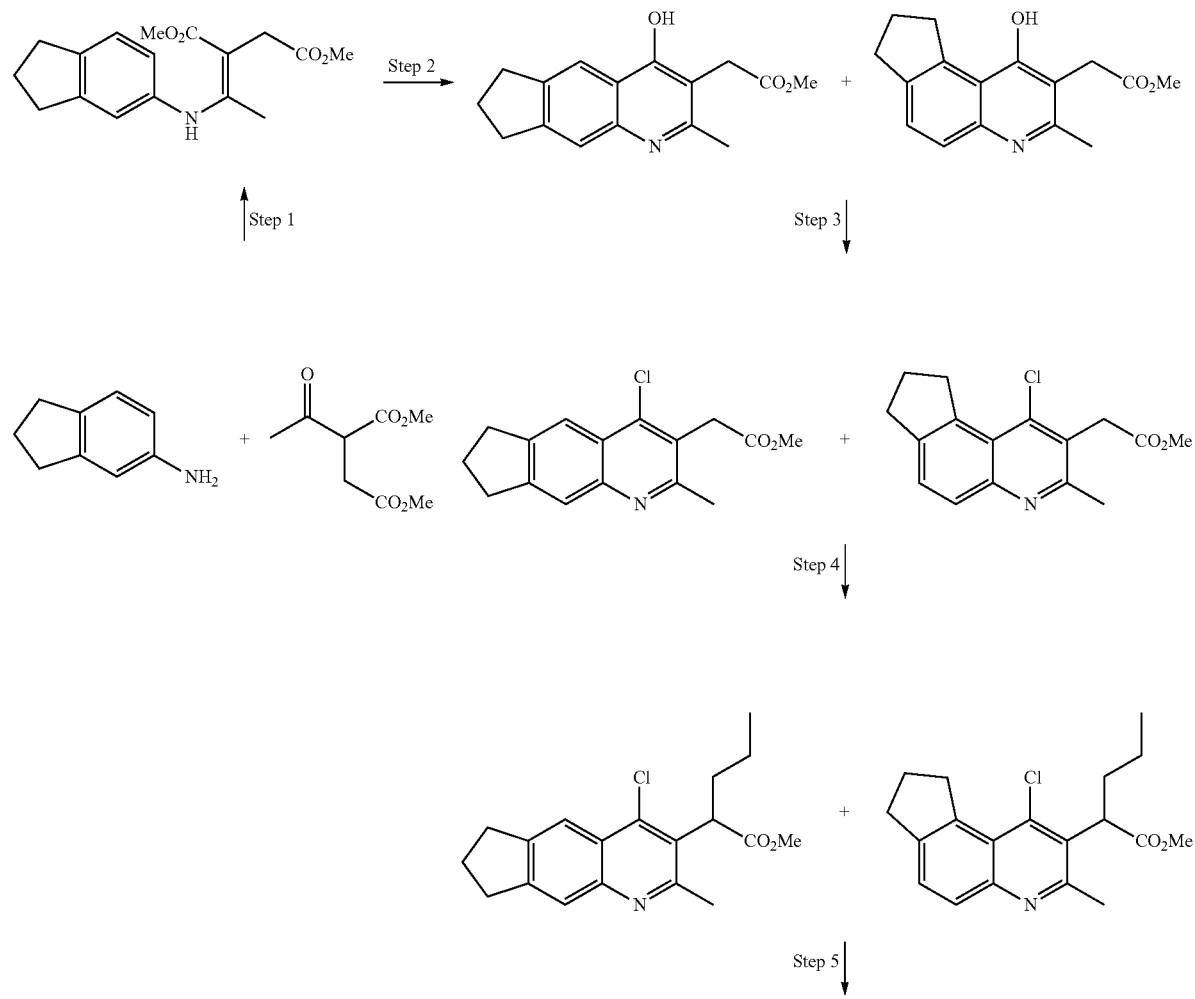

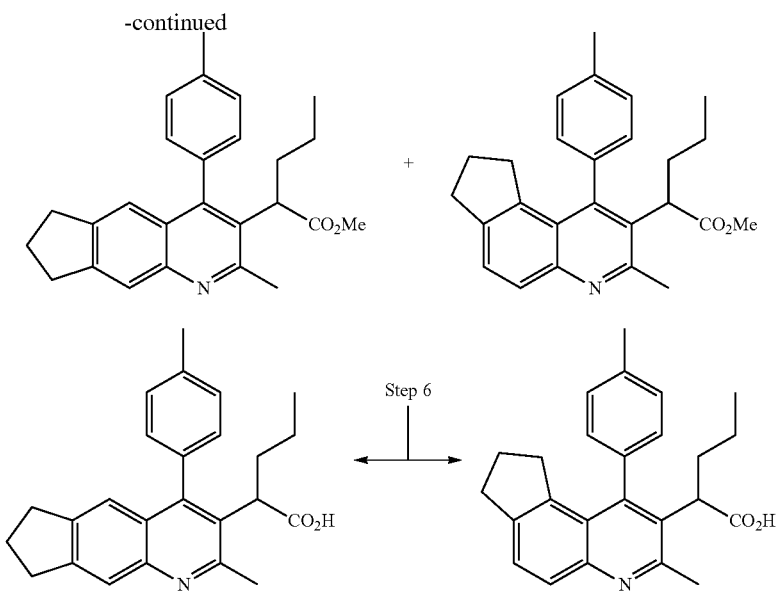

Step 1:

2,3-dihydro-1H-inden-5-amine (10 g; 75 mmol) and dimethyl acetylsuccinate (12.82 g; 68 mmol) were mixed in a flask placed in a dessicator and the homogeneous mixture was stirred under vacuum (3 mbars) for 3 days. Purification by flash chromatography on silica gel using a gradient of ethyl acetate (0 to 20%) in heptane furnished 11.1 g (48%) of dimethyl 2-(1-(2,3-dihydro-1H-inden-5-ylamino)ethylidene)succinate as a deep orange oil.

Step 2:

A solution of dimethyl-2-(1-(2,3-dihydro-1H-inden-5-ylamino)ethylidene)succinate (11 g; 36 mmol) in diphenylether (36 mL) was divided in 4 fractions of 9 mL and each fraction was heated at 250° C. for 15 minutes in a microwave oven (20 mL Biotage reactor). The 4 batches were combined and ethanol (120 mL) was added. The mixture was placed in a sonication bath for 10 minutes and then left at room temperature for 15 minutes. The formed precipitate was filtered off, successively washed with ethanol, heptane, ethylacetate and diisopropylether and then dried under reduced pressure over phosphorus pentoxide to furnish 4.5 g (46%) of a mixture of methyl 2-(4-hydroxy-2-methyl-7,8-dihydro-6H-cyclopenta[g]quinolin-3-yl)acetate and methyl 2-(1-hydroxy-3-methyl-8,9-dihydro-7H-cyclopenta[f]quinolin-2-yl)acetate as a yellow solid. ESI/APCI(+): 272 (M+H).

Step 3:

A mixture of methyl 2-(4-hydroxy-2-methyl-7,8-dihydro-6H-cyclopenta[g]quinolin-3-yl)acetate and methyl 2-(1-hydroxy-3-methyl-8,9-dihydro-7H-cyclopenta[f]quinolin-2-yl)acetate (4.4 g; 16.2 mmol) was dissolved in phosphorus oxychloride (17 mL) under a nitrogen atmosphere and the reaction mixture was heated at reflux for 4 h. After cooling, the volatiles were removed under reduced pressure and the reaction mixture was quenched by adding crushed-ice and a saturated solution of sodium hydrogen carbonate to pH 7. The product was extracted with ethyl acetate and the organic layers were collected, dried over magnesium sulfate and concentrated under reduced pressure. Purification by flash-chromatography on silica gel using a gradient of ethyl acetate (10-75%) in dichloromethane furnished 4.41 g (94%) of a mixture of methyl 2-(4-chloro-2-methyl-7,8-dihydro-6H-cyclopenta[g]quinolin-3-yl)acetate and methyl 2-(1-chloro-3-methyl-8,9-dihydro-7H-cyclopenta[f]quinolin-2-yl)acetate as a yellow solid. ESI/APCI(+): 290-292 (M+H). $^1$H NMR (DMSO-$d_6$) δ 7.92 (s, 1H, 1 Harom.); 7.77 (m, 2H, 2 Harom.); 7.64 (m, 1H, 1 Harom.); 4.09 (s, 4H, 2×CH$_2$); 3.66 (s, 6H, 2×CO$_2$CH$_3$); 3.66-3.58 (m, 2H, Hcyclohexyl); 3.08-2.97 (m, 6H, Hcyclohexyl); 2.62 (s, 6H, 2×CH$_3$); 2.14-2.07 (m, 4H, Hcyclohexyl).

Step 4:

To a solution of a mixture of methyl 2-(4-chloro-2-methyl-7,8-dihydro-6H-cyclopenta[g]quinolin-3-yl)acetate and methyl 2-(1-chloro-3-methyl-8,9-dihydro-7H-cyclopenta[f]quinolin-2-yl)acetate (1.45 g; 5 mmol) in dry DMF (20 mL) at −10° C. was added LHMDS (1M in THF) (5.5 mL; 5.5 mmol) and 1-iodopropane (0.733 mL; 7.5 mmol). The reaction mixture was allowed to warm up to room temperature and the reaction mixture was stirred for 20 h. A saturated ammonium chloride solution (12 ml) was added and the mixture was extracted with ethyl acetate. The organics were combined, washed with brine, dried over magnesium sulfate and concentrated under reduced pressure. Purification by flash-chromatography on silica gel using a gradient of ethyl acetate (2-30%) in dichloromethane furnished 1.59 g (96%) of a mixture of methyl 2-(4-chloro-2-methyl-7,8-dihydro-6H-cyclopenta[g]quinolin-3-yl)pentanoate and methyl 2-(1-chloro-3-methyl-8,9-dihydro-7H-cyclopenta[f]quinolin-2-yl)pentanoate as a light beige solid. ESI/APCI(+): 332 (M+H).

Step 5:

To a mixture of 2-(2-methyl-4-p-tolyl-7,8-dihydro-6H-cyclopenta[g]quinolin-3-yl)pentanoate and methyl 2-(3-methyl-4-p-tolyl-7,8-dihydro-6H-cyclopenta[g]quinolin-2-yl)pentanoate (0.207 g; 0.6 mmol) dissolved in a mixture of 1,2-dimethoxyethane-water (3:1) (4.8 mL) were added 4-methylboronic acid (0.272 g; 2 mmol), tetrakis(triphenylphosphine)palladium (0.173 g; 0.15 mmol) and diisopropylethylamine (0.538 mL; 3 mmol) and the reaction mixture was heated in a microwave oven for 20 minutes at 140° C. After cooling, brine was added and the reaction mixture was extracted with ethyl acetate. The organic layers were combined, dried over magnesium sulfate and concentrated under reduced pressure. Purification by flash-chromatography on silica gel using a gradient of ethyl acetate (1-30%) in dichloromethane furnished 0.316 g (81%) of a mixture of methyl 2-(2-methyl-4-p-tolyl-7,8-dihydro-6H-cyclopenta[g]quinolin-3-yl)pentanoate and methyl 2-(3-methyl-1-p-tolyl-8,9-dihydro-7H-cyclopenta[f]quinolin-2-yl)pentanoate as a light beige solid. ESI/APCI(+):388 (M+H).

Step 6:

To a solution of methyl 2-(2-methyl-4-p-tolyl-7,8-dihydro-6H-cyclopenta[g]quinolin-3-yl)pentanoate and methyl 2-(3-methyl-4-p-tolyl-8,9-dihydro-6H-cyclopenta[g]quinolin-3-yl)pentanoate (0.316 g; 0.81 mmol) in a mixture methanol-ethanol (2:1) (24 mL) was added a 5% sodium hydroxide solution (24.46 mmol; 19.5 mL) and the reaction mixture was heated to 60° C. for 18 h. The organic volatiles were removed under reduced pressure and the remaining basic solution was acidified to pH 2 with a 1N hydrochloric solution and the aqueous layer was extracted with ethyl acetate. The organics were combined, dried over magnesium sulfate and concentrated under reduced pressure. Purification by preparative HPLC (method 1) furnished 0.003 g (1%) of 2-(3-methyl-1-p-tolyl-8,9-dihydro-7H-cyclopenta[f]quinolin-2-yl)pentanoic acid. ESI/APCI(+): 374 (M+H). $^1$H NMR (CDCl$_3$) δ 7.90 (d, J=8.35 Hz, 1H, H-9); 7.53 (d, J=8.35 Hz, 1H, H-8); 7.27 (bs, 1H, H-6'); 7.26 (bs, 1H, H-5'); 7.25 (d, J=8.2 Hz, 1H, H-3'); 7.06 (d, J=8.2 Hz, 1H, H-2'); 3.83 (t, J=6.7 Hz, 1H, H-12); 2.89, (m, 2H, H-7); 2.72 (s, 3H, H-10); 2.47 (s, 3H, H-7'); 2.22 (m, 1H, H-5); 2.18 (m, 1H, H-13); 2.02 (m, 1H, H-5); 1.84 (m, 1H, H-6); 1.76 (m, 1H, H-6); 1.63 (m, 1H, H-13); 1.19 (m, 1H, H-14); 0.97 (m, 1H, H-14); 0.737 (t, J=7.3 Hz, 3H, H-15). $^{13}$C NMR (CDCl$_3$) δ 177.4 (C-11); 155.7 (C-2); 148.1 (C-4); 145.4 (C-9a); 143.1 (C-7a); 139.8 (C-4b); 137.9 (C-4'); 136.6 (C-1'); 131.5 (C-3); 129.8 (C-2'); 129.7 (C-3'); 128.9 (C-6'); 128.5 (C-5'); 126.7 (C-9); 126.6 (C-8); 124.1 (C-4a); 46.04 (C-12); 34.12 (C-5); 33.12 (C-7); 32.77 (C-13); 25.25 (C-6); 23.50 (C-10); 21.44 (C-14); 21.40 (C-7'); 14.14 (C-15).

and 0.011 g (3.6%) of 2-(2-methyl-4-p-tolyl-7,8-dihydro-6H-cyclopenta[g]quinolin-3-yl)pentanoic acid and 2-(3-methyl-1-p-tolyl-8,9-dihydro-7H-cyclopenta[f]quinolin-2-yl) pentanoic acid as a (8/2) mixture. ESI/APCI(+): 374 (M+H).

Example 4

Preparation of ethyl 4-oxo-2-propylpentanoate

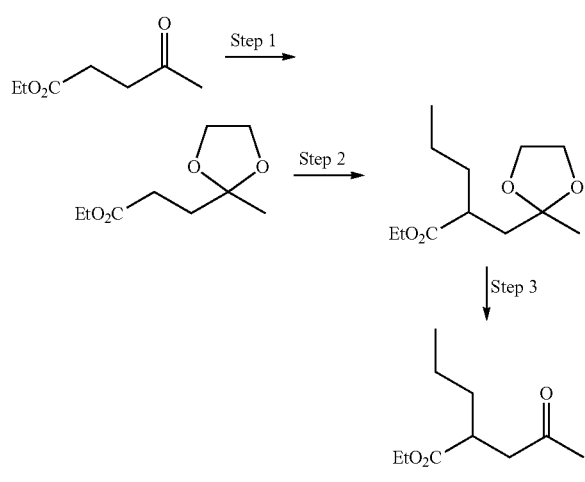

Step 1:

In a flask equipped by a Dean-Stark trap, a mixture of ethyl levulinate (28.83 g; 200 mmol), ethylene glycol (37.24 g; 600 mmol) and a catalytic amount of pyridinium para-toluenesulfonic acid in toluene (200 mL) was heated at reflux until the theoretical amount of water was distilled off. After cooling, the mixture was washed with a saturated solution of sodium hydrogen carbonate. The basic layer was extracted with diethylether and the organics were combined, then washed with brine and water. The organic layer was dried over sodium sulfate and concentrated under reduced pressure to afford the ethyl 3-(2-methyl-1,3-dioxolan-2-yl)propanoate as a colorless oil. ESI/APCI(+): 189 (M+H). $^1$H NMR (CDCl$_3$): δ 4.12 (q, J=7.14 and 14.25 Hz, 2H, CO$_2$CH$_2$CH$_3$); 3.93 (m, 4H, OCH$_2$CH$_2$O); 2.37 (m, 2H, CH$_2$); 2.02 (m, 2H, CH$_2$); 1.32 (s, 3H, CH$_3$); 1.25 (t, J=7.14 Hz, 3H, CO$_2$CH$_2$CH$_3$).

Step 2:

To a cooled (−78° C.) solution of lithium diisopropylamine (30 mL; 60 mmol; 2N in THF) in THF (8 mL) was added hexamethylphosphoramide (12 mL) and the solution was stirred for 30 min. A solution of ethyl 3-(2-methyl-1,3-dioxolan-2-yl)propanoate (9.4 g; 50 mmol), in tetrahydrofurane (9 mL), was added over 30 min and stirring was continued for 1 h. Propyl iodide (6.84 mL; 70 mmol) was slowly added and the solution was allowed to warm to room temperature for 4 h. the reaction was quenched by adding a saturated aqueous solution of ammonium chloride. The two phases were separated and the aqueous layer was extracted with ethyl acetate (50 mL) and the combined organic layers were dried with sodium sulfate, filtered and concentrated under reduced pressure. The crude residue was purified by flash-chromatography on silica gel using a gradient of ethyl acetate (0-40%) in heptane to furnish 9.8 g (85%) of ethyl 2-((2-methyl-1,3-dioxolan-2-yl)methyl)pentanoate as an oil. ESI/APCI(+): 231 (M+H).

Step 3:

To a solution of ethyl 2-((2-methyl-1,3-dioxolan-2-yl)methyl)pentanoate (9.8 g; 42.55 mmol) in hexane (106 mL) at −78° C. under nitrogen atmosphere was added borontribromide (55 mL; 55 mmol; 1M in dichloromethane) and the reaction mixture was stirred at −20° C. for 2 h. Water (50 mL) and ethyl acetate (50 mL) were added to the reaction mixture and the layers were separated. The aqueous layer was extracted with ethyl acetate and the combined organic layers were dried over sodium sulfate, filtered and concentrated under reduced pressure. Purification by flash chromatography on silica gel using a gradient of ethyl acetate (1-40%) in heptane furnished 6.41 g (81%) of ethyl 4-oxo-2-propylpentanoate as a light yellow oil. ESI/APCI(+): 187 (M+H). $^1$H NMR (CDCl$_3$): δ 4.15 (q, J=7.14 and 14.25 Hz, 2H, CO$_2$CH$_2$CH$_3$); 2.88 (m, 2H, CH$_2$); 2.51 (m, 1H, CH); 2.16 (s, 3H, CH$_3$); 1.62-1.23 (m, 7H, CH$_2$CH$_2$CH$_3$); 0.90 (t, J=7.14 Hz, 3H, CO$_2$CH$_2$CH$_3$).

Example 5

Preparation of 2-(2-methyl-4-p-tolyl-pyrrolidino[1,2-b]imidazo[4,5-b]pyridin-3-yl)pentanoic acid (Cpd 072)

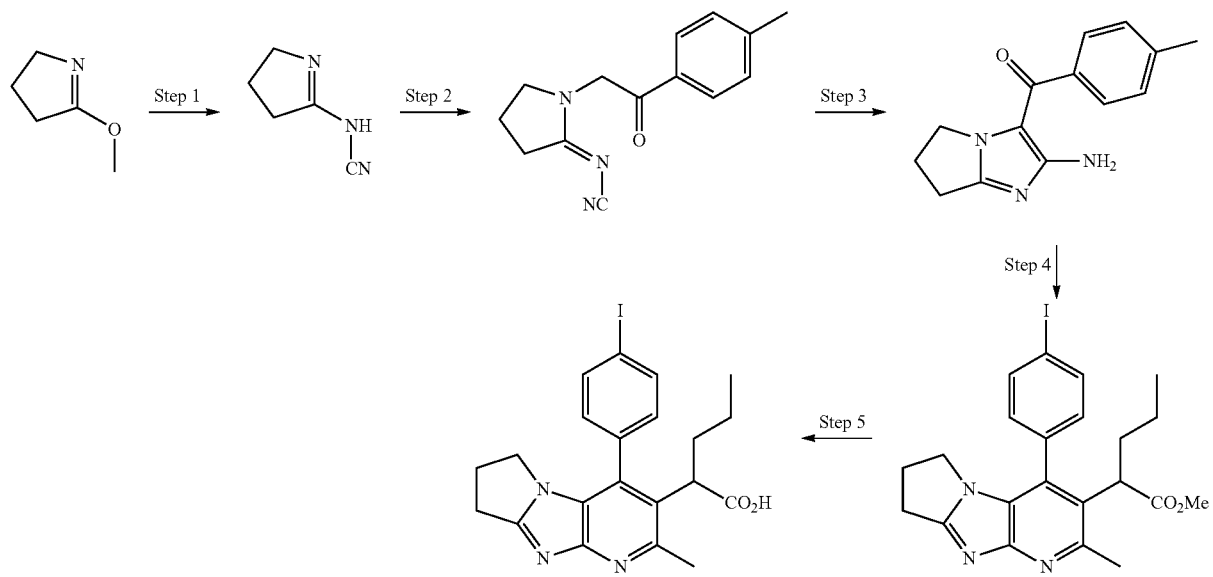

Step 1:
To a solution of 5-methoxy-3,4-dihydro-2H-pyrrole (1.98 g; 20 mmol) in methanol (20 mL) was slowly add cyanamide (0.882 g; 21 mmol). After 5 minutes, a suspension appeared and the reaction mixture was stirred at room temperature for 8 days. The volatiles were removed under reduced pressure to afford 2.18 g (100%) of N-(pyrrolidin-2-ylidene)cyanamide as a white solid which was used without further purification. ESI/APCI(+): 110 (M+H). $^1$H NMR (DMSO-d$_6$) δ 9.50-8.60 (bs, 1H, NH); 3.44 (m, 2H, CH$_2$); 2.66 (m, 2H, CH$_2$); 2.02 (m, 2H, CH$_2$).

Step 2:
A suspension of N-(pyrrolidin-2-ylidene)cyanamide (1.09 g; 10 mmol) in acetonitrile (20 mL) was heated gently until dissolution and then potassium hydrogenocarbonate (1.66 g; 12 mmol) and 2-bromo-1-p-tolylethanone (2.98 g; 14 mmol) were added. The well stirred mixture was heated at reflux for 21 h and an extra amount of 2-bromo-1-p-tolylethanone (0.426 g; 2 mmol) was added. The reaction mixture was heated for 6 additional hours. After cooling, the precipitate was filtered, washed with dichloromethane and the filtrate was concentrated under reduced pressure. The crude residue was purified by flash-chromatography on silica gel using a gradient of ethyl acetate (1-20%) in dichloromethane to furnish 2.02 g (84%) of N-(1-(2-oxo-2-p-tolylethyl)pyrrolidin-2-ylidene)cyanamide as an orange solid. ESI/APCI(+): 242 (M+H). $^1$H NMR (CDI$_3$) δ 7.83 (d, J=8.22 Hz, 2H, Harom.); 7.29 (d, J=8.04 Hz, 2H, Harom.); 4.81 (s, 2H, COCH$_2$); 3.69 (m, 2H, CH$_2$); 3.03 (m, 2H, CH$_2$); 2.43 (s, 3H, CH$_3$); 2.24 (m, 2H, CH$_2$).

Step 3:
Sodium ethanolate (3.4 mL; 9.12 mmol) was added to a solution of N-(1-(2-oxo-2-p-tolylethyl)pyrrolidin-2-ylidene)cyanamideulfonate (2 g; 8.29 mmol) in dry ethanol (50 mL) under a nitrogen atmosphere and the reaction mixture was heated at reflux for 30 min. After cooling, the volatiles were removed under reduced pressure and the crude residue was purified by flash-chromatography on silica gel using a gradient of methanol (1-10%) in dichloromethane to afford 1.23 g (61%) of (2-amino-6,7-dihydro-5H-pyrrolo[1,2-a]imidazol-3-yl)(p-tolyl)methanone as a brownish solid. ESI/APCI(+): 242 (M+H). $^1$H NMR (DMSO-d$_6$): δ 7.33 (m, 4H, Harom.); 6.40 (bs, 2H, NH$_2$); 3.45 (m, 2H, CH$_2$); 2.67 (m, 2H, CH$_2$); 2.36 (s, 3H, CH$_3$); 2.30 (m, 2H, CH$_2$).

Step 4:
To a solution of (2-amino-6,7-dihydro-5H-pyrrolo[1,2-a]imidazol-3-yl)(p-tolyl)methanone (0.280 g; 1.16 mmol) and ethyl 4-oxo-2-propylpentanoate (0.432 g; 2.32 mmol) in dry DMF (9 mL) under a nitrogen atmosphere was added trimethylsilyl chloride (1.19 mL; 9.28 mmol). The mixture was stirred in a sealed tube and heated at 100° C. for 24 h. The starting amino-imidazole was detected on TLC as the main compound so an extra amount of ethyl 4-oxo-2-propylpentanoate (0.308 g; 1.66 mmol) and trimethylsilyl chloride (0.6 mL; 4.64 mmol) were added and the mixture was stirred at 100° C. for 48 additional hours. After cooling, the mixture was poured into water and the suspension was vigorously stirred for 10 min. The aqueous layer was extracted with ethyl acetate and the combined organic layers were dried over sodium sulfate and concentrated under reduced pressure. Purification by flash-chromatography on silica gel using a gradient of methanol (0-20%) in dichloromethane as eluent furnished 0.228 g (50%) of ethyl 2-(2-methyl-4-p-tolyl-pyrrolidino[1,2-b]imidazo[4,5-b]pyridin-3-yl)pentanoate as a brown oil. ESI/APCI(+): 229 (M+H).

Step 5:
To a suspension of ethyl 2-(2-methyl-4-p-tolyl-pyrrolidino[1,2-b]imidazo[4,5-b]pyridin-3-yl)pentanoate (0.228 g; 0.582 mmol) in a mixture of methanol and ethanol (2:1) (18 mL) was added a 5% sodium hydroxide solution (17.47 mmol; 14 mL) and the reaction mixture was heated at 60° C. for 18 h. The organic volatiles were removed under reduced pressure and the remaining basic solution was acidified to pH 2 with a hydrochloric acid solution (1N) and extracted with ethyl acetate twice. The organic layers were combined, dried over sodium sulfate and concentrated under reduced pressure. Purification by preparative HPLC (method 1) furnished 0.015 g (7%) of 2-(2-methyl-4-p-tolyl-pyrrolidino[1,2-b]imidazo[4,5-b]pyridin-3-yl)pentanoic acid as a beige solid. ESI/APCI(+): 364 (M+H).

Example 6

Preparation of 2-(2-methyl-4-p-tolyl-5,6,7,8-tetrahydropyridino[1,2-b]imidazo[4,5-b]pyridin-3-yl)pentanoic acid (Cpd 069)

cyanamide (1.52 g; 5.95 mmol) in dry ethanol (36 mL) under a nitrogen atmosphere and the reaction mixture was heated at reflux for 30 min. After cooling, the volatiles were removed under reduced pressure and the crude residue was purified by flash-chromatography on silica gel using a gradient of methanol (1-10%) in dichloromethane to afford 1.04 g (68%) of (2-amino-5,6,7,8-tetrahydroimidazo[1,2-a]pyridin-3-yl)(p-tolyl)methanone as a brownish solid. ESI/APCI(+): 256 (M+H). $^1$H NMR (DMSO-$d_6$): δ 7.35 (m, 4H, Harom.); 5.63

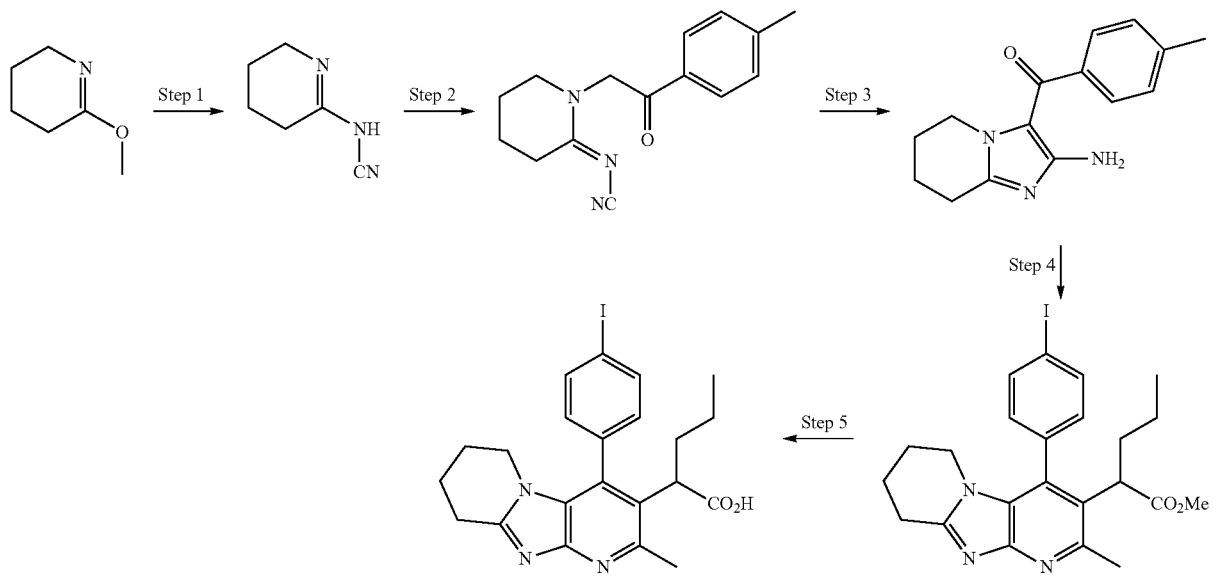

Step 1:
To a solution of 6-methoxy-2,3,4-5-tetrahydropyridine (2.26 g; 20 mmol) in methanol (20 mL) was slowly add cyanamide (0.882 g; 21 mmol). After 5 minutes, a suspension appeared and the reaction mixture was stirred at room temperature for 8 days. The volatiles were removed under reduced pressure to afford 2.46 g (100%) of N-(piperidin-2-ylidene)cyanamide as a white solid which was used without further purification. ESI/APCI(+): 124 (M+H). $^1$H NMR (DMSO-$d_6$) δ 8.99 (bs, 1H, NH); 3.18 (m, 2H, $CH_2$); 2.53 (m, 2H, $CH_2$); 1.66 (m, 4H, 2×$CH_2$).

Step 2:
A suspension of N-(piperidin-2-ylidene)cyanamide (1.23 g; 10 mmol) in acetonitrile (20 mL) was heated gently until dissolution and then potassium hydrogenocarbonate (1.66 g; 12 mmol) and 2-bromo-1-p-tolylethanone (2.98 g; 14 mmol) were added. The well stirred mixture was heated at reflux for 21 h and an extra amount of 2-bromo-1-p-tolylethanone (0.426 g; 2 mmol) was then added. The reaction mixture was heated for 6 additional hours. After cooling, the precipitate was filtered, washed with dichloromethane and the filtrate was concentrated under reduced pressure. The crude residue was purified by flash-chromatography on silica gel using a gradient of ethyl acetate (1-20%) in dichloromethane to furnish 1.52 g (59%) of N-(1-(2-oxo-2-p-tolylethyl)piperidin-2-ylidene)cyanamide as an orange solid. ESI/APCI(+): 256 (M+H). $^1$H NMR ($CDI_3$) δ 7.83 (d, J=8.22 Hz, 2H, Harom.); 7.29 (d, J=8.04 Hz, 2H, Harom.); 4.89 (s, 2H, $COCH_2$); 3.43 (m, 2H, $CH_2$); 2.89 (m, 2H, $CH_2$); 2.43 (s, 3H, $CH_3$); 1.92 (m, 4H, 2×$CH_2$).

Step 3:
Sodium ethanolate (2.44 mL; 6.55 mmol) was added to a solution of N-(1-(2-oxo-2-p-tolylethyl)piperidin-2-ylidene)

(bs, 2H, $NH_2$); 3.64 (m, 2H, $CH_2$); 2.66 (m, 2H, $CH_2$); 2.36 (s, 3H, $CH_3$); 1.74 (m, 4H, 2×$CH_2$).

Step 4:
To a solution of (2-amino-5,6,7,8-tetrahydroimidazo[1,2-a]pyridin-3-yl)(p-tolyl)methanone (0.510 g; 2 mmol) and ethyl 4-oxo-2-propylpentanoate (0.745 g; 4 mmol) in dry DMF (16 mL) under a nitrogen atmosphere was added trimethylsilyl chloride (3 mL; 12 mmol). The mixture was stirred in a sealed tube and heated at 100° C. for 24 h. The starting amino-imidazole was detected on TLC as the main compound so an extra amount of ethyl 4-oxo-2-propylpentanoate (0.372 g; 2 mmol) and trimethylsilyl chloride (1 mL; 4 mmol) were added and the mixture was stirred at 100° C. for 48 additional hours. After cooling, the mixture was poured into water and the suspension was vigorously stirred for 10 min. The aqueous layer was extracted with ethyl acetate and the combined organic layers were dried over sodium sulfate and concentrated under reduced pressure. Purification by flash-chromatography on silica gel using a gradient of methanol (0-20%) in dichloromethane as eluent furnished 0.370 g (45%) of ethyl 2-(2-methyl-4-p-tolyl-5,6,7,8-tetrahydropyridino[1,2-b]imidazo[4,5-b]pyridin-3-yl)pentanoate as a brown oil. ESI/APCI(+): 406 (M+H).

Step 5:
To a suspension of ethyl 2-(2-methyl-4-p-tolyl-5,6,7,8-tetrahydropyridino[1,2-b]imidazo[4,5-b]pyridin-3-yl)pentanoate (0.370 g; 0.912 mmol) in a mixture of methanol and ethanol (2:1) (30 mL) was added a 5% sodium hydroxide solution (27.37 mmol; 21.9 mL) and the reaction mixture was heated at 60° C. for 18 h. The organic volatiles were removed under reduced pressure and the remaining basic solution was acidified to pH 2 with a hydrochloric acid solution (1N) and extracted with ethyl acetate twice. The organic layers were combined, dried over sodium sulfate and concentrated under reduced pressure. Purification by preparative HPLC (method 1) furnished 0.07 g (2%) of 2-(2-methyl-4-p-tolyl-5,6,7,8-tetrahydropyridino[1,2-b]imidazo[4,5-b]pyridin-3-yl)pentanoic acid as a beige solid. ESI/APCI(+): 378 (M+H).

Example 7

Preparation of 2-[2-oxo-1-propyl-4-(p-tolyl)-5,6,7,8-tetrahydro[1]benzothieno[2,3-b]pyridin-3-yl]pentanoic acid (Cpd 086)

Step 1:
To a solution of sodium ethoxide 21% in ethanol (1.8 mL; 4.8 mmol) in dry ethanol (30 mL) under a nitrogen atmosphere was added (2-amino-4,5,6,7-tetrahydrobenzo[b]thiophen-3-yl)(p-tolyl)methanone (1.09 g; 4 mmol) and diethyl succinate (0.929 mL; 5.6 mmol). The mixture was heated to 100° C. for 24 h. The reaction mixture was dissolved with water (8 ml) and acidified with a solution of hydrochloric acid 1N to pH 1 and the aqueous layer was extracted with ethyl acetate. The organics were combined, dried over sodium sulphate and concentrated under reduced pressure. The crude was suspended in dry ethanol (30 mL) and a catalytic amount of concentrated sulfuric acid (10 drops) was carefully added. The reaction mixture was heated to reflux for 21 h. The volatiles were removed under reduced pressure and the remaining residue was purified by flash-chromatography on silica gel using a gradient of methanol (1-20%) in ethyl acetate as eluent to furnish 0.358 g (19.6%) of ethyl[2-hydroxy-4-(p-tolyl)-5,6,7,8-tetrahydro[1]benzothieno[2,3-b]pyridin-3-yl]acetate as an ochre solid. ESI/APCI(+): 382 (M+H).
Step 2:
To a solution of ethyl[2-hydroxy-4-(p-tolyl)-5,6,7,8-tetrahydro[1]benzothieno[2,3-b]pyridin-3-yl]acetate (0.074 g; 0.193 mmol) in dry DMF (1 mL) at −10° C. was added LHMDS (1M in THF) (0.485 mL; 0.485 mmol) and 1-iodopropane (0.076 mL; 0.776 mmol). The reaction mixture was allowed to warm up to room temperature and the reaction mixture was stirred for 18 h. A saturated ammonium chloride solution (2 ml) was added and the mixture was extracted with ethyl acetate. The organics were combined, washed with brine, dried over magnesium sulfate and concentrated under reduced pressure. The crude material was purified by flash-chromatography on silica gel column using a gradient of methanol (1-10%) in dichloromethane as eluent to afford 0.075 g (83%) of ethyl[2-oxo-1-propyl-4-(p-tolyl)-5,6,7,8-tetrahydro[1]benzothieno[2,3-b]pyridin-3-yl]pentanoate as an oil. ESI/APCI(+): 466 (M+H).
Step 3:
To a suspension of ethyl[2-oxo-1-propyl-4-(p-tolyl)-5,6,7,8-tetrahydro[1]benzothieno[2,3-b]pyridin-3-yl]pentanoate (0.071 g; 0.152 mmol) in a mixture of methanol and ethanol (2:1) (4.5 mL) was added a 5% sodium hydroxide solution (3.66 mL; 4.57 mmol) and the reaction mixture was heated to 90° C. for 7 h. The organic volatiles were removed under reduced pressure and the remaining basic solution was acidified to pH 2 with a 1N hydrochloric acid solution. The aqueous layer was extracted with ethyl acetate and the organics were combined, dried over sodium sulfate, concentrated under reduced pressure. Purification by preparative HPLC (method 2) furnished 0.015 g (22.7%) of 2-[2-oxo-1-propyl-4-(p-tolyl)-5,6,7,8-tetrahydro[1]benzothieno[2,3-b]pyridin-3-yl]pentanoic acid as a white solid. ESI/APCI(+): 438 (M+H).

Example 8

Preparation of 2-[2-ethyl-4-p-tolylbenzo[b][1,8]naphthyridin-3-yl]pentanoic acid (Cpd 110)

Step 1:
Iron powder (39 g; 700 mmol) and concentrated hydrochloric acid (0.583 mL; 7 mmol) were added to a solution of 2-nitrobenzaldehyde (10.58 g; 70 mmol) in a mixture ethanol (210 mL)-water (52 mL). The well-stirred reaction mixture was heated to reflux for 5 h. After cooling, the suspension was filtered on a plug of celite, washed with ethanol and the filtrate was concentrated under reduced pressure until the organics were removed. The remaining aqueous layer was extracted with ethyl acetate, the organics were combined, dried over sodium sulfate, concentrated under reduced pressure to furnish 8.2 g (96%) of 2-aminobenzaldehyde as a yellow oil, which crystallized slowly. ESI/APCI(+): 122 (M+H). NMR $^1$H (CDCl$_3$) (ppm): δ 9.87 (s, 1H, CHO); 7.48 (dd, 1H, Harom.); 7.31 (td, 1H, Harom.); 6.75 (td, 1H, Harom.); 6.51 (dd, 1H, Harom.); 6.11 (bs, 2H, NH$_2$).
Step 2:
To a solution of 2-aminobenzaldehyde (2.42 g; 20 mmol) in dry ethanol (60 mL) was added malonitrile (1.89 mL; 30 mmol) and piperidine (0.988 mL; 10 mmol). The reaction mixture was partitioned in four sealed tubes and heated at 100° C. for 24 h. The volatiles were removed under reduced pressure and the remaining crude was purified by flash-chromatography using a gradient of ethyl acetate (5-80%) in dichloromethane as eluent to furnish 1.94 g (57%) of 2-aminoquinoline-3-carbonitrile as an ochre solid. ESI/APCI: 170 (M+H).
Step 3:
To a solution of 2-aminoquinoline-3-carbonitrile (1.86 g; 11 mmol) in dry tetrahydrofurane (110 mL) under a nitrogen atmosphere was slowly added a solution of p-tolylmagnesium bromide (1M in THF) (55 mL; 55 mmol). The resulting solution was stirred at room temperature for 4 h. A solution of hydrochloric acid 3N (220 mL) was added to hydrolyse the intermediate imine and the reaction mixture was heated to reflux for 2 h and then stirred at room temperature for 18 h. After cooling to 0° C., the reaction mixture was basified with a solution of sodium hydroxide 6N. The product was extracted with ethyl acetate (160 mL) and the organics were dried over sodium sulfate, filtered and concentrated under reduced pressure. Purification by flash-chromatography on silica gel using a gradient of ethyl acetate (5-100%) in dichloromethane as eluent furnished 2.6 g (90%) of (2-aminoquinolin-3-yl)(p-tolyl)methanone as an ochre solid. ESI/APCI(+): 263 (M+H).
Step 4:
To a solution of (2-aminoquinolin-3-yl)(p-tolyl)methanone (0.525 g; 2 mmol) and diethyl malonate (1.22 mL; 8 mmol) in ethanol (10 mL) under nitrogen atmosphere was added a solution of sodium ethoxide 21% (w/w) in ethanol (2.24 mL; 6 mmol). The mixture was stirred in a sealed tube and heated to 100° C. for 48 h. The volatiles were removed under reduced pressure and the remaining residue was purified by flash-chromatography on silica gel column using a gradient of ethyl acetate (1-60%) in dichloromethane as eluent to furnish 0.217 g (30%) of ethyl 2-hydroxy-4-p-tolylbenzo[b][1,8]naphthyridine-3-carboxylate as a bright yellow solid. ESI/APCI(+): 359 (M+H). NMR $^1$H (DMSO-d$_6$)

(ppm): δ 12.54 (s, 1H, NH); 8.21 (s, 1H, Harom.); 8.03 (d, 1H, Harom.); 7.93-7.80 (m, 2H, 2×Harom.); 7.51-7.46 (m, 1H, Harom.); 7.41-7.32 (m, 4H, 4×Harom.); 4.02 (q, 2H, OCH$_2$CH$_3$); 2.43 (s, 3H, CH$_3$); 0.94 (t, 3H, OCH$_2$CH$_3$).

The rest of the synthesis can be achieve according to Scheme 13 to afford 2-[2-ethyl-4-p-tolylbenzo[b][1,8]naphthyridin-3-yl]pentanoic acid.

Example 9

Preparation of 2-[2-hydroxy-4-(p-tolyl)-6,7,8,9-tetrahydrobenzo[b][1,8]naphthyridin-3-yl]pentanoic acid (cpd 102)

Step 1:
To a solution of ethoxymethylenemalonitrile (6.11 g; 50 mmol) in dry tetrahydrofuran (170 mL) at −35° C. was carefully added in small portions a mixture of 1-(pyrrolidino)-1-cyclohexene 8.45 mL; 52.5 mmol) in dry tetrahydrofuran (120 mL) under a nitrogen atmosphere. After 1.5 h of stirring, the reaction mixture was allowed to warm slowly until 0° C. and stirring was carried on 1 h more. A solution of ammonia in methanol 7N (120 mL) was slowly added and the resulting mixture was stirred at room temperature for 18 h. The mixture was diluted in water and dichloromethane was added; the organic layer was washed with brine, dried over magnesium sulfate and concentrated under reduced pressure. The crude residue was crystallized in ethanol (2 times) to afford 1.22 g (14%) of 2-amino-5,6,7,8-tetrahydroquinoline-3-carbonitrile as a white solid. ESI/APCI(+): 174 (M+H).
Step 2:
To a solution of 2-amino-5,6,7,8-tetrahydroquinoline-3-carbonitrile (1.2 g; 6.93 mmol) in dry tetrahydrofurane (70 mL) under nitrogen atmosphere was slowly added a solution of p-tolylmagnesium bromide (1M in THF) (35 mL; 35 mmol). The resulting solution was stirred at room temperature for 3 h and heated at 50° C. for 3 h. A solution of hydrochloric acid 3N (140 mL) was added to hydrolyse the intermediate imine and the reaction mixture was heated to reflux for 3 h. After cooling at 0° C., the reaction mixture was basified with a solution of sodium hydroxide 6N. The product was extracted with dichloromethane (200 mL) and the organics were dried over sodium sulfate, filtered and concentrated under reduced pressure. Purification by flash-chromatography on silica gel using a gradient of ethyl acetate (10-100%) in dichloromethane as eluent furnished 1.51 g (82%) of (2-amino-5,6,7,8-tetrahydroquinolin-3-yl)(p-tolyl)methanone as a bright yellow solid. ESI/APCI(+): 267 (M+H).
Step 3:
To a solution of (2-amino-5,6,7,8-tetrahydroquinolin-3-yl)(p-tolyl)methanone (0.533 g; 2 mmol) and diethyl malonate (1.22 mL; 8 mmol) in ethanol (10 mL) under nitrogen atmosphere was added a solution of sodium ethoxide 21% (w/w) in ethanol (2.24 mL; 6 mmol). The mixture was stirred in a sealed tube and heated to 100° C. for 48 h. The volatiles were removed under reduced pressure and the remaining residue was purified by flash-chromatography on silica gel column using a gradient of ethyl acetate (1 to 60%) in dichloromethane as eluent to furnish 0.186 g (25%) of ethyl 2-hydroxy-4-(p-tolyl)-6,7,8,9-tetrahydrobenzo[b][1,8]naphthyridine-3-carboxylate as a white solid. ESI/APCI(+): 363 (M+H). NMR $^1$H (DMSO-d$_6$) (ppm): δ 12.37 (s, 1H, NH); 7.35-7.19 (m, 5H, 5×Harom.); 4.00 (q, 2H, OCH$_2$CH$_3$); 2.88 (m, 2H, CH$_2$); 2.66 (m, 2H, CH$_2$); 2.35 (s, 3H, CH$_3$); 1.86-1.79 (m, 2H, CH$_2$); 1.74-1.69 (m, 2H, CH$_2$); 0.90 (t, 3H, OCH$_2$CH$_3$).

The following steps of the synthesis can be performed according to Scheme 13 to afford 2-[2-hydroxy-4-(p-tolyl)-6,7,8,9-tetrahydrobenzo[b][1,8]naphthyridin-3-yl]pentanoic acid.

Example 10

Preparation of 2-[2-oxo-1-propyl-4-(p-tolyl)-5,6,7,8-tetrahydro[1]benzothieno[3,2-b]pyridin-3-yl]pentanoic acid (Cpd 112)

Step 1:
Phosphorus oxychloride (11.5 mL; 124 mmol) was cooled in an ice-salt bath and DMF (10.0 mL; 130 mmol) was added over a period of 20 min (a sticky white solid was formed). Cyclohexanone (8.0 mL; 77 mmol) was added over 15 min (the sticky solid turned into a bright yellow solution). The mixture was heated at 50° C. and hydroxylamine hydrochloride (30 g; 432 mmol) was added in 5 portions at 5 min intervals maintaining the temperature between 45 and 55° C. via cooling if needed. The reaction mixture was poured into ice-water (300 mL) and the aqueous mixture was stirred for 1 h. The brown solid was filtered, washed with water and dried under reduced pressure over phosphorus pentoxide to afford 9.06 g (83%) of 2-chlorocyclohex-1-enecarbonitrile as a rust-brown solid. ESI/APCI (+): 160-162 (M+H+H$_2$O). $^1$H-NMR (400 MHz, DMSO-d$_6$) (ppm) δ: 2.48 (2H, m), 2.35 (2H, m), 1.74-1.77 (2H, M), 1.71-1.66 (2H, M).
Step 2:
To a solution of 2-chlorocyclohex-1-enecarbonitrile (3.01 g; 21.3 mmol) in a mixture ethanol-tetrahydrofurane (6:1, 42 mL) were added potassium carbonate (3.12 g; 22.6 mmol) and ethyl 2-mercaptoacetate (3.5 mL; 31.9 mmol). The solution was heated under nitrogen atmosphere at 90° C. for 24 h. The solvent was evaporated under reduced pressure and the residue was purified by flash-chormatography on silica gel using a gradient of ethyl acetate (0-10%) in heptane as eluent to yield 2.4 g (50%) of ethyl 3-amino-4,5,6,7-tetrahydrobenzo[b]thiophene-2-carboxylate as a bright yellow solid. ESI/APCI (+): 226 (M+H).

The following steps of the synthesis can be performed according to Scheme 10 to afford the 2-[2-oxo-1-propyl-4-(p-tolyl)-5,6,7,8-tetrahydro[1]benzothieno[3,2-b]pyridin-3-yl]pentanoic acid.

Example 11

Preparation of tert-butoxy-(2-methyl-4-p-tolyl-6,7,8,9-tetrahydro-benzo[q]quinolin-3-yl)-acetic acid (Cpd 002)

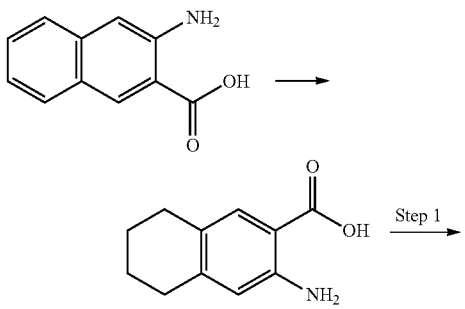

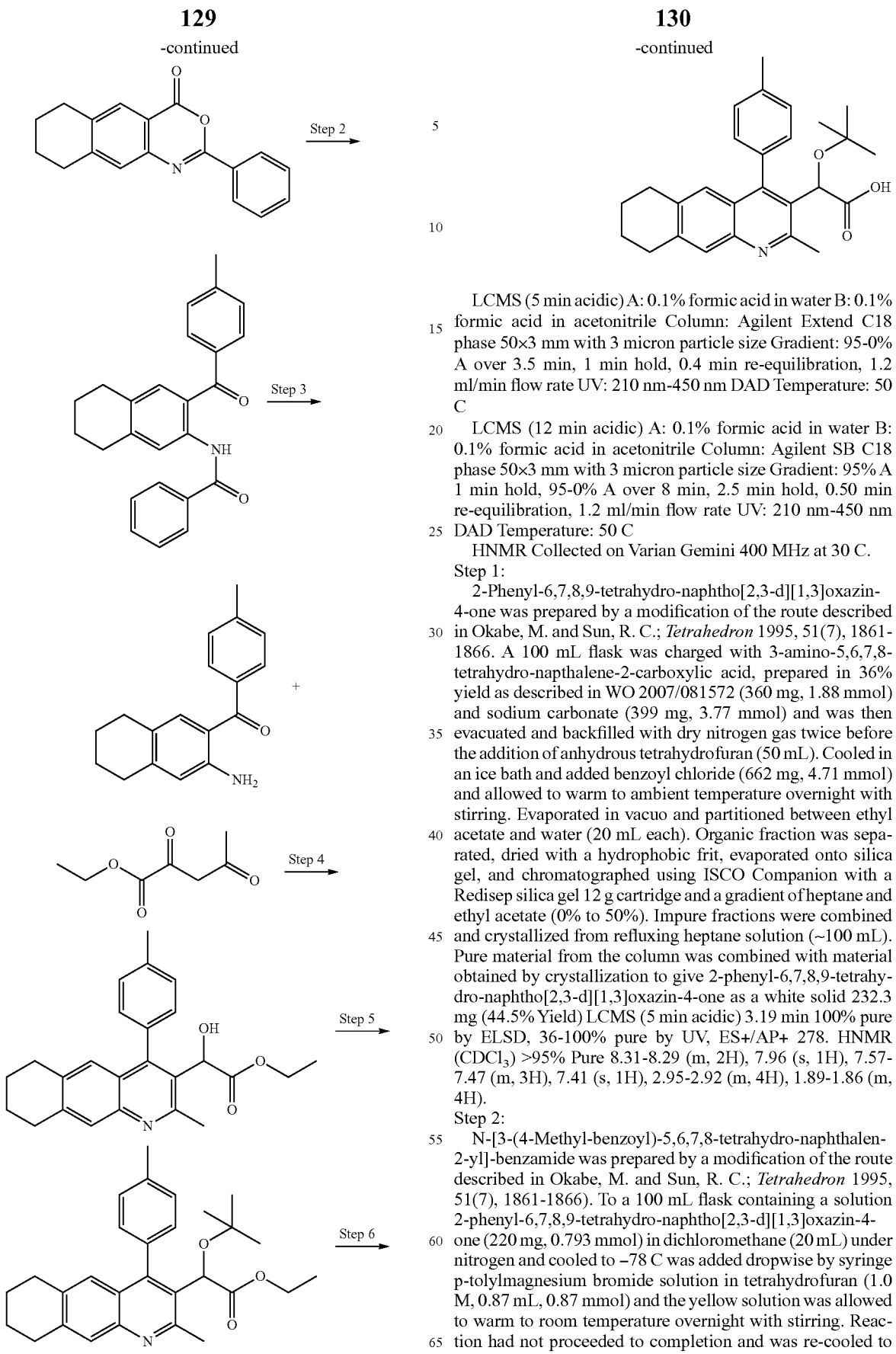

LCMS (5 min acidic) A: 0.1% formic acid in water B: 0.1% formic acid in acetonitrile Column: Agilent Extend C18 phase 50×3 mm with 3 micron particle size Gradient: 95-0% A over 3.5 min, 1 min hold, 0.4 min re-equilibration, 1.2 ml/min flow rate UV: 210 nm-450 nm DAD Temperature: 50 C LCMS (12 min acidic) A: 0.1% formic acid in water B: 0.1% formic acid in acetonitrile Column: Agilent SB C18 phase 50×3 mm with 3 micron particle size Gradient: 95% A 1 min hold, 95-0% A over 8 min, 2.5 min hold, 0.50 min re-equilibration, 1.2 ml/min flow rate UV: 210 nm-450 nm DAD Temperature: 50 C HNMR Collected on Varian Gemini 400 MHz at 30 C.

Step 1:

2-Phenyl-6,7,8,9-tetrahydro-naphtho[2,3-d][1,3]oxazin-4-one was prepared by a modification of the route described in Okabe, M. and Sun, R. C.; *Tetrahedron* 1995, 51(7), 1861-1866. A 100 mL flask was charged with 3-amino-5,6,7,8-tetrahydro-napthalene-2-carboxylic acid, prepared in 36% yield as described in WO 2007/081572 (360 mg, 1.88 mmol) and sodium carbonate (399 mg, 3.77 mmol) and was then evacuated and backfilled with dry nitrogen gas twice before the addition of anhydrous tetrahydrofuran (50 mL). Cooled in an ice bath and added benzoyl chloride (662 mg, 4.71 mmol) and allowed to warm to ambient temperature overnight with stirring. Evaporated in vacuo and partitioned between ethyl acetate and water (20 mL each). Organic fraction was separated, dried with a hydrophobic frit, evaporated onto silica gel, and chromatographed using ISCO Companion with a Redisep silica gel 12 g cartridge and a gradient of heptane and ethyl acetate (0% to 50%). Impure fractions were combined and crystallized from refluxing heptane solution (~100 mL). Pure material from the column was combined with material obtained by crystallization to give 2-phenyl-6,7,8,9-tetrahydro-naphtho[2,3-d][1,3]oxazin-4-one as a white solid 232.3 mg (44.5% Yield) LCMS (5 min acidic) 3.19 min 100% pure by ELSD, 36-100% pure by UV, ES+/AP+ 278. HNMR (CDCl$_3$) >95% Pure 8.31-8.29 (m, 2H), 7.96 (s, 1H), 7.57-7.47 (m, 3H), 7.41 (s, 1H), 2.95-2.92 (m, 4H), 1.89-1.86 (m, 4H).

Step 2:

N-[3-(4-Methyl-benzoyl)-5,6,7,8-tetrahydro-naphthalen-2-yl]-benzamide was prepared by a modification of the route described in Okabe, M. and Sun, R. C.; *Tetrahedron* 1995, 51(7), 1861-1866. To a 100 mL flask containing a solution 2-phenyl-6,7,8,9-tetrahydro-naphtho[2,3-d][1,3]oxazin-4-one (220 mg, 0.793 mmol) in dichloromethane (20 mL) under nitrogen and cooled to –78 C was added dropwise by syringe p-tolylmagnesium bromide solution in tetrahydrofuran (1.0 M, 0.87 mL, 0.87 mmol) and the yellow solution was allowed to warm to room temperature overnight with stirring. Reaction had not proceeded to completion and was re-cooled to –78 C and added more p-tolylmagnesium bromide solution (0.30 mL, 0.38 eq) and transferred the reaction to an acetonitrile-$CO_2$ bath (−42 C) and stirred for 1 hour. Quenched by addition of saturated ammonium chloride solution (2 mL) and allowed to warm to ambient temperature. Diluted further with water (10 mL) and the organic fraction was removed using a hydrophobic frit, evaporated onto silica gel, and chromatographed using ISCO Companion with a Redisep silica gel 40 g cartridge and a gradient of heptane and ethyl acetate (0% to 20%). Evaporation gave N-[3-(4-methyl-benzoyl)-5,6,7,8-tetrahydro-naphthalen-2-yl]-benzamide as a pale yellow solid 191.4 mg (65.3% Yield). LCMS (5 min acidic) 3.52 min 100% pure by ELSD and UV ES+ 370. HNMR ($CDCl_3$) >95% pure 11.69 (s, 1H), 8.08-8.06 (m, 2H), 7.65-7.63 (m, 2H), 7.55-7.48 (m, 3H), 7.33-7.29 (m, 3H), 2.92-2.89 (m, 2H), 2.71-2.68 (m, 2H), 2.46 (s, 3H), 1.87-1.79 (m, 4H).
Step 3:
To a 50 mL flask containing a stirred solution of N-[3-(4-methyl-benzoyl)-5,6,7,8-tetrahydro-naphthalen-2-yl]-benzamide (191 mg, 517 µmol) in tetrahydrofuran (5 mL), ethanol (5 mL) and water (1 mL) under nitrogen was added sodium hydroxide (340 mg, 8.5 mmol) and heated at reflux overnight. Heating was discontinued and solvents removed in vacuo. Added water (20 mL) and extracted with ethyl acetate (3×20 mL). Combined organics were dried with magnesium sulphate and evaporated in vacuo to give 3-amino-5,6,7,8-tetrahydro-naphthalen-2-yl)-p-tolyl-methanone as a partially crystalline red oil 146 mg (107% Yield). LCMS (5 min acidic) 2.99 min 100% pure by ELSD and UV ES+ and AP+ 266. HNMR ($CDCl_3$) >90% pure 7.57-7.55 (m, 2H), 7.27-7.24 (m, 2H), 7.16 (s, 1H), 6.46 (s, 1H), 5.63 (br-s, 2H), 2.72-2.69 (m, 2H), 2.59-2.56 (m, 2H), 2.43 (s, 3H), 1.77-1.73 (m, 4H).
Step 4:
Step 4A: A 50 mL flask containing 3-amino-5,6,7,8-tetrahydro-naphthalen-2-yl)-p-tolyl-methanone (145 mg, 546 µmol) and ethyl 2,4-dioxovalerate (77.0 uL, 546 µmol) was evacuated and backfilled with dry nitrogen gas (3×) before the addition of anhydrous N,N-dimethylformamide (5 mL) and trimethylsilylchloride (279 uL, 2.18 mmol). The red-orange solution was heated at 60 C in an oil bath for 2 hours. Evaporated in vacuo and partitioned between dichloromethane and water (10 mL each). Organics were removed using hydrophobic frit and evaporated in vacuo to give the crude product as a yellow solid (170 mg). Chromatographed twice using ethyl acetate-heptane systems on silica, but unable to achieve separation of the two components. The 75:25 mixture of components (163 mg, 25% desired isomer) was used directly in the next step.
Step 4B: To a 50 mL flask containing a solution of the mixture of isomers from step 1 in ethanol (10 mL) under nitrogen was added sodium borohydride (55 mg, 1.44 mmol) and the yellow suspension was stirred at ambient temperature overnight. Evaporated in vacuo and acidified with hydrochloric acid solution (2 N, 5 mL) and extracted with ethyl acetate (2×5 mL). Organics were dried using a hydrophobic frit and evaporated onto silica gel. Chromatographed using ISCO Companion with a Redisep silica gel 4 g cartridge and a gradient of starting with dichloromethane and ending with dichloromethane:methanol:ammonia (90:10:1). The product was not obtained pure and was subjected again to chromatography using the same conditions as before but with a gradient of heptane and ethyl acetate (0-30%). Evaporation gave hydroxy-(2-methyl-4-p-tolyl-6,7,8,9-tetrahydro-benzo[g] quinolin-3-yl)-acetic acid ethyl ester as a white solid 15.3 mg (7.1% over two steps). LCMS (12 min acidic) 4.82 min 100% pure by ELSD and UV ES+ and AP+ 390. HNMR ($CDCl_3$) >95% pure 7.75 (s, 1H), 7.34-7.30 (m, 2H), 7.24-7.22 (m, 2H), 7.01 (s, 1H), 5.25 (s, 1H), 4.23-4.15 (10 peaks, 2H), 3.31 (br-s, 1H), 3.02-2.99 (m, 2H), 2.81-2.78 (m, 2H), 2.70 (s, 3H), 2.48 (s, 3H), 1.86-1.79 (m, 4H), 1.19 (t, 3H).
Step 5:
To a 50 mL flask containing a stirred suspension of hydroxy-(2-methyl-4-p-tolyl-6,7,8,9-tetrahydro-benzo[g] quinolin-3-yl)-acetic acid ethyl ester (15.3 mg, 39.0 µmol) in tert-butyl acetate (4 mL) under nitrogen was added perchloric acid (72%, 9.80 uL, 117 µmol) and the clear solution was stirred at ambient temperature for 3 hours. Added sodium carbonate solution (10%) until neutralization had occurred and extracted with ethyl acetate (10 mL). Organics were dried using a hydrophobic frit and evaporated onto silica. Chromatographed using ISCO Companion with a Redisep silica gel 4 g cartridge and a gradient of heptane and ethyl acetate (0-20%). Evaporation gave tert-butoxy-(2-methyl-4-p-tolyl-6,7,8,9-tetrahydro-benzo[g]quinolin-3-yl)-acetic acid ethyl ester as a clear oil 11.1 mg (63.8% Yield). LCMS (5 min acidic) 2.66 min 100% pure by ELSD and UV ES+ and AP+ 446. HNMR ($CDCl_3$) >95% pure 7.76 (br-s, 1H), 7.37-7.32 (m, 3H), 7.22-7.20 (m, 1H), 7.03 (br-s, 1H), 5.14 (s, 1H), 4.21-4.15 (m, 2H), 3.00 (br-t, 2H), 2.85-2.73 (m, 5H), 2.50 (s, 3H), 1.88-1.77 (m, 4H), 1.22 (t, 3H), 0.97 (s, 9H).
Step 6:
A 50 mL flask containing a solution of tert-butoxy-(2-methyl-4-p-tolyl-6,7,8,9-tetrahydro-benzo[g]quinolin-3-yl)-acetic acid ethyl ester (11.1 mg 25.0 µmol) in ethanol (1 mL) and tetrahydrofuran (1 mL) under nitrogen was added sodium hydroxide solution (1.0 M, 250 µL, 250 µmol) and stirred at ambient temperature overnight. Complete conversion was then achieved by heating to 60 C for 30 min. Evaporated in vacuo and azeotroped with toluene (2×5 mL). Residue was taken up in water (10 mL) and acidified to pH=2 with hydrochloric acid solution (2 M) then extracted into ethyl acetate (2×10 mL). Organics were dried with magnesium sulfate and evaporated onto silica gel. Chromatographed using ISCO Companion with a Redisep silica gel 4 g cartridge with an isocratic gradient of ethyl acetate:acetic acid (90:10). Evaporation gave tert-butoxy-(2-methyl-4-p-tolyl-6,7,8,9-tetrahydro-benzo[g]quinolin-3-yl)-acetic acid as a colorless solid 7.1 mg (68% Yield). LCMS (12 min acidic) 5.32 min 100% pure by ELSD and UV AP+ and ES+ 418. HNMR ($CDCl_3$) >95% pure 7.77 (br-s, 1H), 7.59 (br-d, 1H), 7.36-7.32 (br-m, 2H), 7.22 (br-d, 1H), 7.10 (br-s, 1H), 5.29 (br-s, 1H), 2.99 (br-t, 2H), 2.85-2.78 (m, 4H), 2.49 (s, 3H), 2.18 (s, 3H), 1.86-1.81 (m, 4H), 0.98 (s, 9H)
Part B: Biological Evaluation of the Compounds of the Invention Example 12

Evaluation of the Anti-HIV Activity of the Compounds of the Invention

MT4 based Cytopathic Effect Assay
A rapid and automated assay procedure was used for the in vitro evaluation of anti-HIV agents. An HTLV-1 transformed T4-cell line MT-4, which was previously shown to be highly susceptible to and permissive for HIV infection, served as the target cell line. Inhibition of the HIV-induced cytopathogenic effect was used as the end point. The viability of both HIV- and mock-infected cells was assessed spectrophotometrically via in situ reduction of 3-(4,5-dimethylthiazol-2-yl)-2,5-diphenyltetrazolium bromide (MTT). The 50% cytotoxic concentration ($CC_{50}$ in µg/ml) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in \%}$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($EC_{50}$ in µg/ml or µM). The ratio of $CC_{50}$ to $EC_{50}$ was defined as the selectivity index (SI). Examples of $EC_{50}$, $CC_{50}$ and SI values for inhibition of proliferation of HIV by particular compounds of the invention are listed in table 3 herein below.

Examples of inhibition of cell proliferation by particular compounds of the invention can be found by looking at the respective $CC_{50}$ values in the MT-4 cell line.

Cells: MT-4 cells (Miyoshi et al., 1982) were grown and maintained in RPMI 1640medium supplemented with 10% heat-inactivated fetal calf serum, 2 mM I-glutamine, 0.1% sodium bicarbonate, and 20æg of gentamicin per ml.

Viruses: The HIV-1(NL4.3) strain (Adachi et al., 1986) is a molecular clone obtained from the National Institutes of Health (Bethesda, Md.). The HIV-2(ROD) (Barr,-Sinoussi et al., 1983) stock was obtained from culture supernatant of HIV-2 infected cell lines.

MT-2 Based Antiviral Assay (S8737E)

Much like the MT-4 based cytopathic effect assay, this assay is designed to determine the effects of small molecules on the replication of HIV-1 in the lymphobastoid cell line, MT2, and is able to detect the antiviral effect of compounds acting at any stage of the HIV-1 replication cycle. The assay, along with its associated cytotoxicity assay, was described in detail in 2005 in a paper by Cao et al (Antimicrobial Agents and Chemotherapy 2005; 49(9), p 3833-3841).

Briefly; MT2 cells are infected with the HIV-1 virus (NL4.3 strain) and transferred to assay plates containing serial dilutions of compounds to be tested. The assay plates are incubated for 3 days (MT2) to allow for several rounds of viral replication/infection to take place. At the end of this time, supernatant is transferred into new plates containing JC53BL cells.

JC53BL cells express CXCR4, CCR5 and CD4 receptors, and HIV-1-LTR-β-Gal. Under normal culture conditions undetectable levels of β-Galactosidase are expressed, but in the presence of HIV-1, the viral Tat protein is able to activate the HIV-1-LTR in the JC53BL cells resulting in the increased expression of the β-Gal enzyme. The expression can be measured using the 'FluorAce β-Galactosidase reporter' assay. The levels of β-Gal are directly proportional to the levels of Tat (up to a threshold) allowing virus quantification. Compounds that inhibit virus replication will give rise to a reduced signal and a dose-response curve for each compound can be generated. This is then used to determine the IC50 for each compound, a measure of the compound's potency, in a manner similar to the MT-4 based cytopathic effect assay.

The MT-2 based antiviral assay requires a separate cytotoxicity assessment of the compounds. This was performed using a 3 day MT-2 cytotoxicity assay as follows:

3 Day MT2 Cytotoxicity Assay (S8738E)

The assay is designed to test whether or not compounds have cytotoxic activity in MT2 cells by measuring the viability of these cells in the presence of compounds. The assay is carried out by adding MT2 assay plates containing serial dilutions of the compounds to be screened. After 3 days incubation, the viability of the cells remaining in the plates is assayed using the commercially available reagent CellTiter-Glo (Promega Ltd). The data generated is then used to calculate the concentration of compound required to cause 50% cytotoxicity (CC50).

References:

Adachi, A., Gendelman, H., Koenig, S., Folks, T., Willey, R., Rabson, A. and Martin, M (1986) Production of acquired immunodeficiency syndrome-associated retrovirus in human and nonhuman cells transfected with an infectious molecular clone, *J. Virol.*, 59, 284-291.

Barr-Sinoussi, F., Chemann, J. C., Rey, F., Nugeyre, M. T., Chamaret, S., Gruest, J., Dauguet, C., Axler-Blin, C., V, zinet-Brun, F., Rouzioux, C., Rozenbaum, W., Montagnier, L. (1983) Isolation of a T-lymphotropic retrovirus from patient at risk for AIDS, *Science* (Wash D.C.) 220, 868-871.

Cao J, Isaacson J, Patick A K, Blair W S. (2005) High-throughput human immunodeficiency virus type 1 (HIV-1) full replication assay that includes HIV-1 Vif as an antiviral target. Antimicrobial Agents and Chemotherapy; 49(9), p 3833-3841.

Miyoshi, I., Taguchi, H., Kobonishi, I., Yoshimoto, S., Ohtsuki, Y., Shiraishi, Y. and Akagi, T. (1982) Type C virus-producing cell lines derived from adult T cell leukemia, *Gann mongr,* 28, 219-228.

Example 13

Assays to Measure the LEDGF-Integrase Interaction Inhibitory Activity of Compounds of the Invention Alpha Screen Interaction Assay An AlphaScreen assay was performed according to the manufacturer's protocol (Perkin Elmer, Benelux). Reactions were performed in 25 µl final volume in 384-well Optiwell™ microtiter plates (Perkin Elmer). The reaction buffer contained 25 mM Tris-HCl (pH 7.4), 150 mM NaCl, 1 mM $MgCl_2$, 0.01% (v/v) Tween-20 and 0.1% (w/v) bovine serum albumin. $His_6$-tagged integrase (300 nM final concentration) was incubated with the compounds for 30 min at 4° C. The compounds were added at varying concentrations spanning a wide range from 0.1 up to 100 µM. Afterwards 100 nM flag-LEDGF/p75 was added and incubation was prolonged for an additional hour at 4° C. Subsequently 5 µl of Ni-chelate-coated acceptor beads and 5 µl anti-flag donor beads were added to a final concentration of 20 µg/ml of both beads. Proteins and beads were incubated for 1 h at 30° C. in order to allow association to occur. Exposure of the reaction to direct light was omitted as much as possible and the emission of light from the acceptor beads was measured in the EnVision plate reader (Perkin Elmer, Benelux) and analyzed using the EnVision manager software. IN/DNA binding was analyzed in a similar setting using $His_6$-tagged integrase (1 µM final concentration) and an oligodeoxynucleotide mimicking the IN ELISA oligonucleotide substrate (30 nM final concentration). Counterscreens with JPO2 or PogZ, respectively, were essentially performed as described previously.

Expression and purification of recombinant proteins: $His_6$-tagged HIV-1 integrase, 3× flag-tagged LEDGF/p75, MBP- JPO2 and MBP-PogZ were purified for AlphaScreen applications as described previously 23, 25, 56.

HTRF Interaction Assay

An Homogeneous Time Resolved Fluorescence (HTRF) assay was performed in a manner similar to previous reports on HTRF protein protein assays as reviewed by Mathis (Clin Chem, 2005). The assay procedure was performed as follows: reactions were performed in 20 μl final volume in 384-well black low volume microtiter plates (Greiner). The final reaction buffer contained 29 mM phosphase buffer (pH 7), 10 mM HEPES buffer (pH 7.4), 68.5 mM NaCl, 1.4 mM KCl, 400 mM KF 0.05% (w/v) pluronic acid (P104, Sigma Aldrich) and 1% (v/v) DMSO. His$_6$-tagged integrase (78 nM final concentration) was incubated with mannose binding protein fused to the Δ325 carboxy terminal integrase binding domain of LEDGF in the presence of compound for 2 hours at room temperature. Both these protein regents were supplied by Prof. Zeger Debyser of Katholieke Universiteit Leuven, Leuven, Belgium. The compounds were added at varying concentrations spanning a wide range from 0.1 up to 100 μM. Afterwards 8.3 nM of europium cryptate conjugated anti-MBP monoclonal antibody and 17 nM anti-His antibody conjugated with the acceptor fluorophore d2. Following a 2 hour room temperature incubation the plates were read on an EnVision™ microplate reader (Perkin Elmer) using an excitation wavelength of 320 nM. The ratio of fluorescence emitted at 665 nM and 620 nM was used to assess the degree to which the protein protein interaction had been inhibited.

References:

Bartholomeeusen, K., et al. Differential interaction of HIV-1 integrase and JPO2 with the C terminus of LEDGF/p75. J. Mol. Biol. 372, 407-421 (2007).

Bartholomeeusen, K., et al. Lens Epithelium Derived Growth Factor/p75 interacts with the transposase derived DDE domain of pogZ. J. Biol. Chem. (2009).

Busschots, K., et al. The interaction of LEDGF/p75 with integrase is lentivirus-specific and promotes DNA binding. J. Biol. Chem. 280, 17841-17847 (2005).

Mathis G., Probing molecular interactions with homogeneous techniques based on rare earth cryptates and fluorescence energy transfer. Clin. Chem. 41 (9), 1391-7 (1995)

Compounds of the invention showed an inhibitory activity on the LEDGF-integrase interaction and an anti-HIV activity. Examples thereof are listed in Table 2.

TABLE 2

Activity of the compounds according to the methods of examples 12 and 13.

| CPD CODE | Alphascreen IC$_{50}$ (μM) | HTRF IC$_{50}$ (μM) | MT4 EC$_{50}$ (μM) | MT4 CC$_{50}$ (μM) | SI | MT2 EC$_{50}$ (μM) | MT2 CC$_{50}$ (μM) | SI | Comment |
|---|---|---|---|---|---|---|---|---|---|
| Cpd001 | 0.47 | | 1.45 | 92 | 63 | | | | mixture containing 50% of Cpd003 |
| Cpd002 | | 0.55 | | | | 0.46 | >10 | >22 | |
| Cpd003 | 0.47 | | 1.45 | 92 | 63 | | | | mixture containing 50% of Cpd001 |
| Cpd012 | 1.08 | | 4.4 | 0.53 | 82 | 155 | 1.68 | >20 | |
| Cpd023 | 4.6 | | | 4.5 | 114.5 | 25 | | | |
| Cpd047 | 7.85 | | 3.1 | 5.51 | 200 | 24 | >20 | | |

All publications and patent applications cited herein are incorporated by reference to the same extent as if each individual publication or patent application was specifically and individually indicated to be incorporated by reference.

What is claimed is:

1. A compound according to the formula (E2):

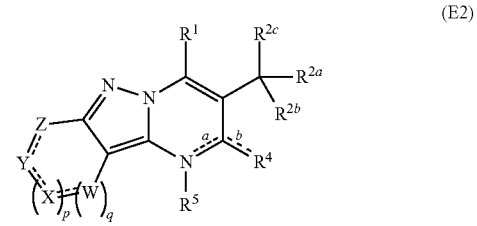

(E2)

wherein,
each dotted line represents an optional double bond, whereby if the dotted line "a" forms a double bond, the dotted line "b" does not form a double bond and whereby if the dotted line "b" forms a double bond, the dotted line "a" does not form a double bond;

$R^1$ is independently selected from the group consisting of alkyl; cycloalkyl; aryl; heterocycle; arylalkyl; and heterocycle-alkyl;
wherein in the cycloalkyl or alkyl moiety of said alkyl, cycloalkyl, arylalkyl, or heterocycle-alkyl, one or more —CH$_3$ or —CH$_2$— is optionally replaced by one or more moieties selected from the group consisting of —NH$_2$, —NH—, —O—, and —S—;
and wherein said alkyl, cycloalkyl, aryl, heterocycle, arylalkyl, or heterocycle-alkyl can be unsubstituted or substituted with one or more $Z^1$;

$R^{2a}$ is hydrogen;
$R^{2b}$ is selected from the group consisting of alkyl; alkenyl; arylalkyl; and heterocycle-alkyl;
wherein in the alkyl moiety of said alkyl, alkenyl, arylalkyl, or heterocycle-alkyl, one or more —CH$_3$ or —CH$_2$— is optionally replaced by one or more moieties selected from the group consisting of —NH$_2$, —NH—, —O—, and —S—;
and wherein said alkyl, alkenyl, arylalkyl, or heterocycle-alkyl can be unsubstituted or substituted with one or more $Z^1$;

$R^{2c}$ is —COOR$^3$;
$R^3$ is selected from the group consisting of hydrogen and alkyl;

when the dotted line "a" forms a double bond, $R^4$ is independently selected from the group consisting of hydrogen; hydroxyl; alkyl; aryl; heterocycle; arylalkyl; and heterocycle-alkyl; and when the dotted line "b" forms a double bond, $R^4$ is independently selected from O and S;

wherein in the alkyl moiety of said alkyl, arylalkyl, or heterocycle-alkyl, one or more —$CH_3$ or —$CH_2$— is optionally replaced by one or more moieties selected from the group consisting of —$NH_2$, —NH—, —O—, and —S—; and wherein said alkyl, aryl, heterocycle, arylalkyl, or heterocycle-alkyl can be unsubstituted or substituted with one or more $Z^1$;

when the dotted line "a" forms a double bond, $R^5$ is not present and when the dotted line "b" forms a double bond, $R^5$ is independently selected from the group consisting of hydrogen; alkyl; aryl; heterocycle; arylalkyl; and heterocycle-alkyl; and wherein said alkyl, aryl, heterocycle, arylalkyl, or heterocycle-alkyl can be unsubstituted or substituted with one or more $Z^1$;

W, X, Y, and Z are independently selected from the group consisting of $CR^{10}$ and $CR^{10}R^{11}$ depending on whether they are adjacent to a double or a single bond;

p is selected from the group consisting of 0; 1; 2; and 3;

q is selected from the group consisting of 0 and 1;

$R^{10}$ and $R^{11}$ are independently selected from the group consisting of hydrogen, halogen; —$OZ^2$; —$SZ^2$; and alkyl; and wherein said alkyl optionally includes one or more heteroatoms, said heteroatoms being selected from the group consisting of atoms O, S and N;

each $Z^1$ is independently selected from the group consisting of halogen; —$OZ^2$; —$SZ^2$; trifluoromethyl; alkyl; aryl; heterocycle; arylalkyl; and heterocycle-alkyl; and wherein in the alkyl moiety of said alkyl, arylalkyl, or heterocycle-alkyl, one or more —$CH_3$ and —$CH_2$— is optionally replaced by one or more moieties selected from the group consisting of —$NH_2$, —NH—, —O—, and —S—; and wherein said alkyl, aryl, heterocycle, arylalkyl, or heterocycle-alkyl can be unsubstituted or substituted with one or more $Z^{11}$;

each $Z^{11}$ is independently selected from the group consisting of halogen; —$OZ^{12}$; —$SZ^{12}$; trifluoromethyl; alkyl; aryl; heterocycle; arylalkyl; and heterocycle-alkyl; and each $Z^2$ and $Z^{12}$ is independently selected from the group consisting of hydrogen; alkyl; aryl; heterocycle; arylalkyl; and heterocycle-alkyl; and wherein in said alkyl, aryl, heterocycle, arylalkyl, or heterocycle-alkyl, one or more —$CH_3$, —$CH_2$—, or —CH═ is optionally replaced by one or more moieties selected from the group consisting of —$NH_2$, —NH—, —O—, —S—, and —N═;

or a pharmaceutically acceptable salt thereof.

2. A compound according to claim 1, wherein $R^{2c}$ is COOH.

3. A compound according to claim 1, wherein $R^1$ is selected from $C_1$-$C_6$ alkyl, phenyl; phenylalkyl, heteroaryl, O-phenyl; S-phenyl or NH-phenyl and wherein said phenyl; phenylalkyl, heteroaryl, O-phenyl; S-phenyl or NH-phenyl can be unsubstituted or substituted with one or more halogen, OH or $C_1$-$C_4$alkyl.

4. A compound according to claim 1, wherein $R^{2b}$ is selected from the group consisting of $C_1$-$C_6$ alkyl and $C_1$-$C_6$-alkoxy, said $C_1$-$C_6$ alkyl and $C_1$-$C_6$ alkoxy being optionally substituted with up to three F atoms.

5. A compound according to claim 1, wherein the dotted line "a" forms a double bond, the dotted line "b" does not form a double bond, $R^5$ is not present and $R^4$ is selected from hydrogen, hydroxyl, alkyl or aryl, wherein said alkyl and aryl can be unsubstituted or substituted with one or more halogens.

6. A compound according to claim 1, wherein the dotted line "b" forms a double bond, the dotted line "a" does not form a double bond, $R^4$ is O and $R^5$ is selected from $C_1$-$C_6$alkyl or benzyl.

7. A compound according to claim 1, wherein p is 1 and q is 1.

8. A compound according to claim 1, wherein $R^{10}$ and $R^{11}$ are independently selected from the group consisting of hydrogen and alkyl.

9. A compound according to claim 1, wherein $R^{10}$ and $R^{11}$ are hydrogen.

10. A compound selected from:

| Cpd Code | Compound | Cpd Code | Compound |
|---|---|---|---|
| 034 | | 035 | |

-continued

| Cpd Code | Compound | Cpd Code | Compound |
|---|---|---|---|
| 036 | | 037 | |
| 038 | | 039 | |
| 040 | | 041 | |
| 042 | | 043 | |

-continued

| Cpd Code | Compound | Cpd Code | Compound |
|---|---|---|---|
| 044 | | 045 | |
| 046 | | 047 | |
| 048 | | 049 | |
| 050 | | 051 | |
| 052 | | 053 | or |

| Cpd Code | Compound | Cpd Code | Compound |
|---|---|---|---|
| 054 | 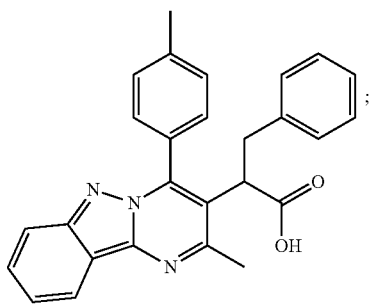 [SMILES: Cc1ccc(-c2c(C(Cc3ccccc3)C(=O)O)c(C)nc3c4ccccc4nn23)cc1] | | | or a pharmaceutically acceptable salt thereof.

11. A pharmaceutical composition comprising a compound according to claim 1 as an active ingredient in admixture with at least one pharmaceutically acceptable carrier.

12. A pharmaceutical composition according to claim 11, further comprising one or more additional compounds with antiviral, in particular anti-HIV, activity.

13. A method of treatment of an HIV infection in an animal or mammal, comprising administering to the animal or mammal in need of such treatment a therapeutically effective amount of a compound according to claim 1.

* * * * *